(12) United States Patent
McElroy et al.

(10) Patent No.: US 8,236,821 B2
(45) Date of Patent: Aug. 7, 2012

(54) SUBSTITUTED N-PHENYL-5-PHENYL-PYRAZOLIN-3-YL AMIDES AS CANNABINOID RECEPTOR ANTAGONISTS/INVERSE AGONISTS USEFUL FOR TREATING OBESITY

(75) Inventors: John F. McElroy, Wilmington, DE (US); Robert J. Chorvat, West Chester, PA (US)

(73) Assignee: Jenrin Discovery, Inc., Wilmington, DE (US)

( * ) Notice: Subject to any disclaimer, the term of this patent is extended or adjusted under 35 U.S.C. 154(b) by 412 days.

(21) Appl. No.: 12/468,119

(22) Filed: May 19, 2009

(65) Prior Publication Data

US 2009/0286758 A1    Nov. 19, 2009

Related U.S. Application Data

(60) Provisional application No. 61/054,182, filed on May 19, 2008.

(51) Int. Cl.
*A61K 31/454* (2006.01)
*A61K 31/4155* (2006.01)

(52) U.S. Cl. ...... 514/326; 514/403; 546/211; 548/364.1
(58) Field of Classification Search .................. None
See application file for complete search history.

(56) References Cited

U.S. PATENT DOCUMENTS

2005/0171179 A1*  8/2005  Lange et al. .................. 514/406
2007/0073056 A1   3/2007  Torrens et al.

FOREIGN PATENT DOCUMENTS

WO    WO 2007/009687    *   1/2007

* cited by examiner

*Primary Examiner* — Rebecca Anderson
*Assistant Examiner* — Alicia L Otton
(74) *Attorney, Agent, or Firm* — Vance Intellectual Property, PC

(57) ABSTRACT

The present invention provides novel pyrazolines that are useful as cannabinoid receptor antagonists/inverse agonists and pharmaceutical compositions thereof and methods of using the same for treating obesity, diabetes, dyslipidemias, cardiovascular disorders, hepatic disorders, and a combination thereof.

12 Claims, No Drawings

SUBSTITUTED N-PHENYL-5-PHENYL-PYRAZOLIN-3-YL AMIDES AS CANNABINOID RECEPTOR ANTAGONISTS/INVERSE AGONISTS USEFUL FOR TREATING OBESITY

CROSS-REFERENCE TO RELATED APPLICATIONS

The present application claims priority benefit under 35 U.S.C. §119(e) of U.S. Provisional Patent Application Ser. No. 61/054,182 filed 19 May 2008. The disclosure this application is incorporated herein by reference.

FIELD OF THE INVENTION

The present invention provides novel substituted N-phenyl-5-phenyl-pyrazolin-2-yl amides and derivatives thereof as cannabinoid receptor antagonists/inverse agonists and pharmaceutical compositions thereof and methods of using the same for treating obesity, diabetes, dyslipidemias, cardiovascular disorders, and/or hepatic disorders. More particularly, the present invention relates to a novel method for treating obesity, diabetes, dyslipidemias, cardiovascular disorders and/or hepatic disorders using a novel substituted N-phenyl-5-phenyl-pyrazolin-2-yl amides and derivatives thereof.

BACKGROUND OF THE INVENTION

Obesity is associated with an increase in the overall amount of adipose tissue (i.e., body fat), especially adipose tissue localized in the abdominal area. Obesity has reached epidemic proportions in the United States. The prevalence of obesity has steadily increased over the years among all racial and ethnic groups. The most recent data from the Centers for Disease Control and Prevention, and the National Center for Health Statistics report 66% of the adult population overweight (BMI, 25.0-29.9), 31% obese (BMI, 30-39.9), and 5% extremely obese (BMI, ≧40.0). Among children aged 6 through 19 years, 32% were overweight and 17% were obese. This translates to 124 million Americans medically overweight, and 44 million of these deemed obese. Obesity is responsible for more than 300,000 deaths annually, and will soon overtake tobacco usage as the primary cause of preventable death in the United States. Obesity is a chronic disease that contributes directly to numerous dangerous co-morbidities, including type 2 diabetes, cardiometabolic diseases, hepatic disorders, cardiovascular disease, inflammatory diseases, premature aging, and some forms of cancer. Type 2 diabetes, a serious and life-threatening disorder with growing prevalence in both adult and childhood populations, is currently the 7$^{th}$ leading cause of death in the United States. Since more than 80% of patients with type 2 diabetes are overweight, obesity is the greatest risk factor for developing type 2 diabetes. Increasing clinical evidence indicates that the best way to control type 2 diabetes is to reduce weight.

The most popular over-the counter drugs for the treatment of obesity, phenylpropanolamine and ephedrine, and the most popular prescription drug, fenfluramine, were removed from the marketplace as a result of safety concerns. Drugs currently approved for the long-term treatment of obesity fall into two categories: (a) CNS appetite suppressants such as sibutramine and rimonabant, and (b) gut lipase inhibitors such as orlistat. CNS appetite suppressants reduce eating behavior through activation of the 'satiety center' in the brain and/or by inhibition of the 'hunger center' in the brain. Gut lipase inhibitors reduce the absorption of dietary fat from the gastrointestinal (GI) tract. Although appetite suppressants and gut lipase inhibitors work through very different mechanisms, they share in common the same overall goal of reducing body weight secondary to reducing the amount of calories that reach the systemic circulation. Unfortunately, these indirect therapies produce only a modest initial weight loss (approximately 5% compared to placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life.

The lack of therapeutic effectiveness, coupled with the spiraling obesity epidemic, positions the 'treatment of obesity' as one of the largest and most urgent unmet medical needs. There is, therefore, a real and continuing need for the development of improved medications that treat or prevent obesity.

The endocanabinoid system, comprised of the canabinoid receptors (CB1 and CB2) and their endogenous ligands (e.g., anandamide, 2-AG), plays a prominent role in the control of food intake and energy metabolism. CB1 receptors are widely expressed in the brain, including cortex, hippocampus, amygdala, pituitary and hypothalamus. CB1 receptors have also been identified in numerous peripheral organs and tissues, including thyroid gland, adrenal gland, reproductive organs, adipose tissue, liver, muscle, pancreas, and gastrointestinal tract. CB2 receptors are localized almost exclusively in immune and blood cells [*Endocrine Reviews* 2006, 27, 73].

The plant-derived cannabinoid agonist $\Delta^9$-tetrahydrocannabinol ($\Delta^9$-THC), the main psychoactive component of marijuana, binds to both CB1 and CB2 receptors. $\Delta^9$-THC is widely reported to increase appetite and food intake (hyperphagia) in humans and in animals. This hyperphagic effect is largely blocked by pretreatment with selective CB1 receptor blockers (i.e., CB1 blockers) (e.g., rimonabant (SR141716A, Acomplia®)), strongly supporting the belief that CB1 receptor activation mediates the hyperphagic effect of $\Delta^9$-THC, [*Endocrine Reviews* 2006, 27, 73].

In humans, rimonabant produces a clinically meaningful weight loss in obese patients. Obese patients also experience improvements in diabetic and cardiometabolic risk factors associated with obesity, including an increase in the level of high density lipoprotein cholesterol (HDL), and decreases in triglycerides, glucose, and hemoglobin A1c (HbA1c, a marker of cumulative exposure to glucose) levels. Rimonabant also produces greater reductions in abdominal fat deposits, which are a known risk factor for diabetes and heart disease [*Science* 2006, 311, 323]. Taken together, these improvements in adiposity and cardiometabolic risk factors produce an overall decrease in the prevalence of the metabolic syndrome [*Lancet* 2005, 365, 1389 and *NEJM* 2005, 353, 2121].

In patients with type 2 diabetes not currently treated with other anti-diabetic medications, rimonabant was shown to significantly improve blood sugar control and weight, as well as other risk factors such as HDL and triglycerides, when compared to placebo (International Diabetes Federation World Diabetes Congress, Cape Town, South Africa, 2006). After six months of treatment, HbA1c levels were significantly lowered by 0.8% from a baseline value of 7.9 as compared to a reduction of 0.3% in the placebo group. These results are consistent with preclinical studies that demonstrate improved glycemic and lipid control in diabetic and dyslipedemic mice, rats, and dogs (*Pharmacology Biochemistry & Behavior,* 2006, 84, 353; *American Journal of Physiology,* 2003, 284, R345; *American Diabetes Association Annual Meeting,* 2007; Abstract Number 0372-OR).

The beneficial effects of rimonabant on diabetic and cardiometabolic risk factors such as high blood pressure, insulin resistance, and elevated triglycerides cannot be explained by diet-related weight loss alone. For example, in patients receiving 20 mg of rimonabant, only approximately 50% of the beneficial effects on triglycerides, fasting insulin, and insulin resistance can be accounted for by weight loss secondary to reduced food intake. These results suggest a direct pharmacological effect of CB1 antagonists on glucose and lipid metabolism, in addition to indirect effects on metabolism secondary to hypophagia-mediated weight loss [*Science* 2006, 311, 323 and *JAMA* 2006, 311, 323]. Taken together, these results suggest that CB1 antagonists might be effective in the treatment of diabetes, dyslipidemias, cardiovascular disorders (e.g., atherosclerosis, hypertension), and hepatic disorders (e.g., cirrhosis, fatty liver diseases), even in patients that are not clinically overweight or obese.

The CB1 receptor is one of the most abundant and widely distributed G protein-coupled receptors in the mammalian brain. It is believed that the appetite-suppressant properties of CB1 antagonists are mediated through an interaction with CB1 receptors in the hypothalamus (regulation of food intake), and in the mesolimbic region (rewarding properties of food). However, CB1 receptors are far more broadly distributed in brain (e.g., neocortex, hippocampus, thalamus, cerebellum, and pituitary), and while interacting with targeted CB1 receptors in hypothalamus and mesolimbic regions to suppress appetite, CB1 antagonists have equal access to non-targeted CB1 receptors that have little if any role in appetite control. Binding to non-targeted receptors can often lead to unwanted side effects of CNS drugs [*Endocrine Reviews* 2006, 27: 73]. The CB1 blockers rimonabant and taranabant produce psychiatric and neurological side effects. These include depressed mood, anxiety, irritability, insomnia, dizziness, headache, seizures, and suicidality.

These side effects are dose-related and appear pronounced at the most efficacious weight-reducing doses of rimonabant and taranabant (*JAMA* 2006, 311, 323; *Cell Metabolism* 2008, 7, 68). The occurrence of therapeutic efficacy (appetite suppression) and side effects over the same dose range strongly suggest that both effects are mediated through concurrent antagonism of CB1 receptors in both 'targeted' and 'non-targeted' brain regions. Brain-penetrant CB1 blockers do not selectively target CB1 receptors in efficacy brain regions, while ignoring CB1 receptors in side effect brain regions.

The beneficial effects of the CB1 antagonist rimonabant on body weight, adiposity, and diabetic and cardiometabolic risk factors such as high blood pressure, insulin resistance and blood lipids cannot be explained by weight loss derived from CNS-mediated appetite suppression alone [*JAMA* 2006, 311, 323]. Approximately 50% of the benefit is likely derived from an interaction with CB1 receptors in peripheral tissues known to play an active role in metabolism. These include adipose tissue, liver, muscle, pancreas, and gastrointestinal tract.

Rosonabant and other brain penetrating compounds are described in US 2007/0073056. These compounds have the following formula:

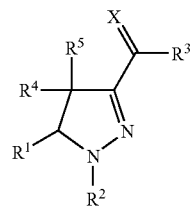

wherein $R^1$ and $R^2$ can be aryl groups and $C(=X)R^3$ can be an amide or thioamide group. The compounds of US 2007/0073056 are not considered to be part of the present invention.

In view of the above, it is highly desirable to find effective and highly selective CB1 receptor blockers with limited or no CNS adverse side effects, including mood disorders. Particularly, it is desirable to find compounds that preferentially target CB1 receptors in peripheral tissues (e.g., adipose tissue, liver, muscle, pancreas, and gastrointestinal tract), while sparing CB1 receptors in brain. In this way, peripherally-mediated beneficial effects of CB1 blockers should be maintained, whereas CNS side effects should be reduced or eliminated. This should provide a novel opportunity to develop safer alternatives to highly brain penetrant CB1 blockers for the prevention or treatment of obesity, diabetes, dyslipidemias, cardiovascular disorders, and/or hepatic disorders.

SUMMARY OF THE INVENTION

Accordingly, in an aspect, the present invention provides novel pyrazolines or pharmaceutically acceptable salts thereof that are CB1 receptor antagonists/inverse agonists.

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating obesity, diabetes (e.g., insulin resistance, inadequate glucose tolerance, Type I diabetes, and Type II diabetes), dyslipidemias (e.g., elevated triglycerides and LDL, and low HDL), cardiovascular disorders (e.g., atherosclerosis and hypertension), and/or hepatic disorders (e.g., nonalcoholic steatohepatitis (NASH), cirrhosis and fatty liver disease), comprising: administering to a mammal in need of such treatment a therapeutically effective amount of at least one of the compounds of the present invention or a pharmaceutically acceptable salt form thereof.

In another aspect, the present invention provides processes for preparing novel compounds.

In another aspect, the present invention provides novel compounds or pharmaceutically acceptable salts for use in therapy.

In another aspect, the present invention provides the use of novel compounds for the manufacture of a medicament for the treatment of obesity, diabetes, dyslipidemias, cardiovascular disorders, and/or hepatic disorders.

These and other objects, which will become apparent during the following detailed description, have been achieved by the inventors' discovery that the presently claimed compounds or pharmaceutically acceptable salt forms thereof are expected to be effective CB1 receptor blockers.

DETAILED DESCRIPTION OF THE INVENTION

All references cited herein are hereby incorporated in their entirety herein by reference.

A CB1 blocker is a neutral CB1 receptor antagonist and/or a CB1 receptor inverse agonist.

The present invention is based on the finding that a CB1 receptor blocker has beneficial effects on metabolic disorders including obesity, diabetes, dyslipidemias, and cardiovascular and hepatic diseases that cannot be explained by weight loss derived from CNS-mediated appetite suppression alone, and that this effect is mediated, at least in part, through interaction at peripheral CB1 receptors. To this end, the present invention provides compounds that are designed to preferentially target CB1 receptors in peripheral tissues (e.g., adipose tissue, liver, muscle, pancreas, and gastrointestinal tract), while sparing CB1 receptors in brain. With these types of compounds, peripherally-mediated beneficial effects of CB1 blockers should be maintained, whereas CNS side effects should be reduced or eliminated.

The compounds of the present invention have been designed to have reduced CNS exposure by virtue of their inability or limited ability to penetrate the blood-brain barrier (BBB), or by their participation in active transport systems, thus reducing centrally mediated side-effects, a potential problem with many anti-obesity agents. It is expected that the peripherally restricted compounds of the present invention will have no or very limited CNS effects, including mood disorders, seizures, and suicidality. Thus, their peripherally mediated CB1 blocking properties should provide therapeutic agents with greater safety.

Moreover, if the maximum dosage of a drug used in the treatment of obesity, diabetes, dyslipidemias, cardiovascular disorders, and/or hepatic disorders is limited as a result of CNS side effects (e.g., seizures, depression, anxiety, suicidality, movement disorders, and hyperactivity), incorporation of a peripherally restricting group in such a drug would lower the brain concentration of the drug relative to the concentration in the systemic circulation, thereby affording the opportunity to increase the dosage employed to treat the peripheral disorder (e.g., obesity, diabetes, dyslipidemias, cardiovascular disorders, and/or hepatic disorders). The increased dosage may provide greater therapeutic efficacy, as well as a more rapid onset of therapeutic action.

In an embodiment, the present invention provides novel compound AA or a stereoisomer or pharmaceutically acceptable salt thereof:

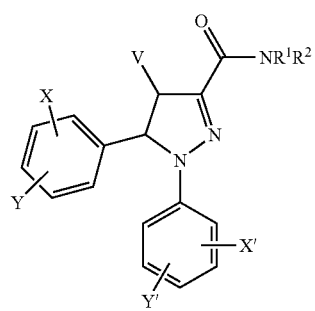

AA wherein:

X, Y, X', and Y' are independently selected from H, halogen, $CF_3$, $NO_2$, $C_{1-6}$ alkyl, $C_{1-6}$ alkoxy, and phenyl;

V is H or $C_{1-6}$ alkyl;

$R^2$ is selected from H, $C_{1-6}$ alkyl, $(CH_2)_{0-6}$ aryl, and $(CH_2)_{0-6}$ heteroaryl;

$R^1$ is selected from H, $C_{1-6}$ alkyl, and a 5-7 membered cyclic amine that is unsaturated, partially saturated, or fully saturated and is substituted with 0-4 groups selected from $CF_3$, $NO_2$, $C_{1-6}$ alkyl, benzyl, phenyl, OH, halogen, and $C_{1-6}$ alkoxy;

when $R^1$ is a cyclic amine, it is attached via its nitrogen atom to the amide nitrogen of formula AA; and at least one of X, Y, X', Y', V, $R^1$, or $R^2$ is suitably modified or replaced by a group capable of reducing or limiting the CNS (brain) levels of compound AA.

[1] In another embodiment, the present invention provides novel compounds of formula I or a stereoisomer or pharmaceutically acceptable salt thereof:

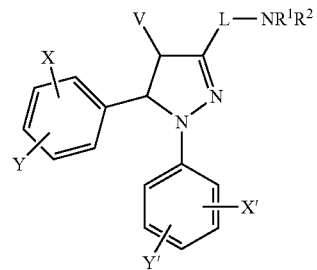

I wherein:

L is C(=O) or $SO_2$;

X, X', Y, and Y' are independently selected from H, halogen, $C_{1-6}$ alkyl, $NO_2$, $CF_3$, $NR_2$, OR, —CN, $(CH_2)_mCO_2R$, $O(CH_2)_nCO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^c_2$, $O(CH_2)_nC_6H_4(CH_2)_nCONR^c_2$, $O(CH_2)_nC_6H_4$-tetrazole, $CH_2O(CH_2)_nC_6H_4CONR^c_2$, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4CONR^c_2$, $CH_2NR^a(CH_2)_nC_6H_4CONR^c_2$, $CH_2NR^a(CH_2)_nC_6H_4$-tetrazole, $(CH_2)_mC(=NH)NH_2$, $(CH_2)_mNHC(=NH)NH_2$, $(CH_2)_mNHC(=CHNO_2)NH_2$, $(CH_2)_mNHC(=NCN)NH_2$, $CONR^c_2$, $(CH_2)_nCONR^c_2$, $NR^cCONR^c_2$, $NR^cCO_2R$, $O(CH_2)_nCONR^c_2$, $CH_2O(CH_2)_nCONR^c_2$, $NR^a(CH_2)_mCONHR^a$, $OCH_2CH=CHCONR^c_2$, $CH_2OCH_2CH=CHCONR^c_2$, $NR^aCH_2CH=CHCONR^c_2$, tetrazole, $O(CH_2CH_2O)_pR$, $NR^a(CH_2CH_2O)_pR$, $SONH_2$, $SO_2NR^aCH_3$, $CH_2N^+R^b{}_3V^1$, $O(CH_2)_n$-aryl, $NR(CH_2)_n$-aryl, $O(CH_2)_n$-5-12 membered heteroaryl consisting of carbon atoms and from 1-4 heteroatoms selected from N, O, and S, $NR(CH_2)_n$-5-12 membered heteroaryl consisting of carbon atoms and from 1-4 heteroatoms selected from N, O, and S, and

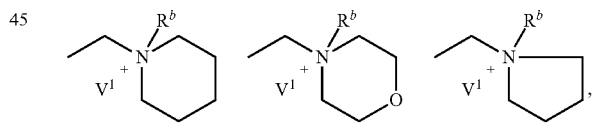

wherein the aryl and heteroaryl groups are independently substituted with 0-2 groups selected from OH, $OC_{1-4}$ alkyl, $OC_{2-4}$ alkenyl, $OC_{2-4}$ alkynyl, halogen, nitro, $N(R)_2$, $NRSO_2CH_3$, $SO_2NRCH_3$, $(CH_2)_rCO_2R^3$, $(CH_2)_rSO_3H$, $(CH_2)_rPO_3H_2$, $(CH_2)_rPO_3RH$, $O(CH_2)_rCO_2R^3$, $O(CH_2)_rSO_3H$, $O(CH_2)_rPO_3H_2$, $O(CH_2)_rPO_3RH$, $S(CH_2)_rCO_2R^3$, $S(CH_2)_rSO_3H$, $S(CH_2)_rPO_3H_2$, $NHR^3CONHR^3$, $NHCO_2R^3$, $S(CH_2)_rPO_3RH$, $(CH_2)_rCON(R^3)_2$, $S(CH_2)_nCON(R^3)_2$, $O(CH_2)_nCON(R^3)_2$, $(CH_2)_rNR^3SO_2R$, $(CH_2)_rC(=NR^3)N(R^3)_2$, $(CH_2)_rNR^3C(=NR^3)N(R^3)_2$, $(CH_2)_rNR^3(C=NR^3CN)N(R^3)_2$, $(CH_2)_rNR^3(C=CHNO_2)N(R^3)_2$, $(CH_2)_rNR^3C(=NR^5)NR^3R^{5a}$, $(CH_2)_r$tetrazol-5-yl, and $O(CH_2CH_2O)_qR^4$;

$R^1$ is selected from H, $C_{1-6}$ alkyl, CHRCHROH, $CR(CHROH)_2$, $C(CHROH)_3$, $CHRCH(aryl)OH$, $CH(aryl)CHROH$, $(CH)_mCH(A)(CH_2)_mC(=NH)NH_2$, $(CH)_mCH(A)(CH_2)_mCO_2R$, $(CH)_mCH(A)(CH_2)_mCONH(CH)_mCH(A)$ $(CH_2)_mCO_2R$, $(CH)_mCH(A)(CH_2)_mCONH(CH)_mCH(A)$ $(CH_2)_mCONH(CH)_mCH(A)(CH_2)_mCO_2R$, $(CH)_mCH(A)$ $(CH_2)_mCONR^c{}_2$, $(CH)_mCH(A)(CH_2)_mCONH(CH)_mCH(A)$ $(CH_2)_mCONR^c{}_2$, $(CH)_mCH(A)(CH_2)_mCONH(CH)_mCH(A)$ $(CH_2)_mCONH(CH)_mCH(A)(CH_2)_mCONR^c{}_2$, $(CH)_mCH(A)$ $(CH_2)_mCONH—CH(A)(CH_2)_m$-tetrazole, $(CH_2)_m$-phenyl-$(CH_2)_mCO_2R$, $(CH_2)_m$-phenyl-$(CH_2)_mCONR^c{}_2$, $(CH_2)_m$-pyridyl-$(CH_2)_mCONR^c{}_2$, $(CH_2)_m$-phenyl-$(CH_2)_mC(=NH)NH_2$, and $(CH_2)_m$-pyridyl-$(CH_2)_m(CN)NH_2$;

alternatively, $R^1$ is

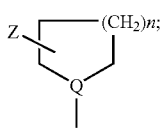

A is selected from H, $C_{1-6}$ alkyl, OH, $C_{1-6}$ alkylene-OH, $(CH_2)_mNR^c{}_2$, $(CH_2)_nCONR^c{}_2$, $(CH_2)_nNHCONR^c{}_2$, $(CH_2)_nNHCO_2R$, $(CH_2)_mC(=NH)NH_2$, $(CH_2)_m$—$C_{3-6}$-cycloalkyl, $(CH_2)_m$-heteroaryl, and $(CH_2)_m$-aryl, wherein each aryl and heteroaryl is substituted with 0-2 groups selected from $CF_3$, halogen, $C_{1-4}$ alkyl, —CN, $CONR^c{}_2$, $NO_2$, $NR_2$, OR, $NR^c$-$CONR^c{}_2$, $NR^cCO_2R$, $NHSO_2CH_3$, and SONHR;

$R^2$ is selected from H, $C_{1-6}$ alkyl, $(CH_2)_{0-6}$ aryl, and $(CH_2)_{0-6}$ heteroaryl, wherein the heteroaryl is attached via a carbon atom;

Z is selected from H, $C_{1-6}$ alkyl, aryl, $NR_2$, NRZ', OR, —CN, $CO_2R$, $(CH_2)_nCO_2R$, $CH_2O(CH_2)_nCO_2R$, $(CH_2)_mC(=NH)NH_2$, $(CH_2)_mNHC(=NH)NH_2$, $(CH_2)_mNHC(=CHNO_2)NH_2$, $(CH_2)_mNHC(=NCN)NH_2$, $NR^cCONR^c{}_2$, $NR^cCO_2R$, $OCH_2CH=CHCO_2R$, $CH_2OCH_2CH=CHCO_2R$, $O(CH_2)_nPO(OR)_2$, $CH_2O(CH_2)_nPO(OR)_2$, $CONR^c{}_2$, $(CH_2)_nCONR^c{}_2$, $O(CH_2)_nCONR^c{}_2$, $CH_2O(CH_2)_nCONR^c{}_2$, $OCH_2CH=CHCONR^c{}_2$, $CH_2OCH_2CH=CHCONR^c{}_2$, and $(CH_2)_mSO_3R$;

Z' is selected from $(CH)_mCH(A)(CH_2)_mCO_2R$, $(CH)_mCH(A)(CH_2)_mCONH(CH)_mCH(A)(CH_2)_mCO_2R$, $(CH)_mCH(A)(CH_2)_mCONH(CH)_mCH(A)(CH_2)_mCONH(CH)_mCH(A)$ $(CH_2)_mCO_2R$, $(CH)_mCH(A)(CH_2)_mCONR^c{}_2$, $(CH)_mCH(A)(CH_2)_mCONH(CH)_mCH(A)(CH_2)_mCONR^c{}_2$, $(CH)_mCH(A)(CH_2)_mCONH(CH)_mCH(A)(CH_2)_mCONH(CH)_mCH(A)$ $(CH_2)_mCONR^c{}_2$, $(CH_2)_m$-phenyl-$(CH_2)_mCO_2R$, $(CH_2)_m$-pyridyl-$(CH_2)_mCO_2R$, $(CH_2)_m$-phenyl-$(CH_2)_mCONR^c{}_2$, and $(CH_2)_m$-pyridyl-$(CH_2)_mCONR^c{}_2$;

Q is selected from N, CH, and CQ';

Q' is selected from H, $CO_2R$, $(CH_2)_nCO_2R$, $CH_2O(CH_2)_nCO_2R$, $CH_2OCH_2CH=CHCO_2R$, $CH_2O(CH_2)_nPO(OR)_2$, $CONR^c{}_2$, $(CH_2)_nCONR^c{}_2$, $CH_2O(CH_2)_nCONR^c{}_2$, $CH_2OCH_2CH=CHCONR^c{}_2$, and $(CH_2)_m$tetrazole;

V is selected from H, $C_{1-6}$ alkyl, $C_{2-6}$ alkenyl, $C_{2-6}$ alkynyl, $CF_3$, aryl, $CH_2OH$, $CH_2O(CH_2CH_2O)_pR$, $(CH_2)_mCN$, $(CH_2)_mC(=NH)NH_2$, $(CH_2)_nNHC(=NH)NH_2$, $(CH_2)_nNHC(=CHNO_2)NH_2$, $(CH_2)_nNHC(=NCN)NH_2$, $(CH_2)_mCONR^c{}_2$, $(CH_2)_mCONR^a(CH_2)_mCH(A)(CH_2)_mCO_2R$, $(CH_2)_mCONR^a(CH_2)_m$-phenyl-$(CH_2)_mCO_2R$, $(CH_2)_mCONR^a(CH_2)_m$-phenyl-$(CH_2)_m$-tetrazole, $CH_2O(CH_2)_nCONR^c{}_2$, $CH_2NR^a(CH_2)_nCONR^c{}_2$, $CH_2N^+R^b{}_3V^1$, tetrazole, and

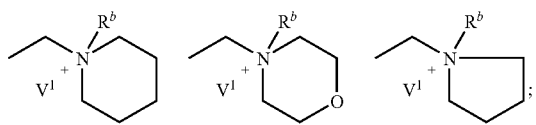

R is independently selected from H and $C_{1-6}$ alkyl;

$R^a$ is independently selected from H, $C_{1-6}$ alkyl, $C_{2-6}$ alkenyl, and $C_{2-6}$ alkynyl;

$R^b$ is independently selected from $O^-$, $C_{1-6}$ alkyl, $C_{3-6}$ alkenyl, and $C_{3-6}$ alkynyl;

$R^c$ is independently selected from H, OH, $C_{1-4}$ alkyl, $C_{3-6}$ alkenyl, CHRCHROH, $CR(CHROH)_2$, $C(CHROH)_3$, CHR-CH(aryl)OH, and CH(aryl)CHROH;

$V^1$ is a counter ion, provided that $V^1$ is absent when $R^b$ is $O^-$;

m is selected from 0, 1, 2, 3, and 4;

n is selected from 1, 2, 3, and 4; and, p is selected from 1, 2, 3, 4, 5, 6, 7, 8, 9, 10, 11, and 12;

In another embodiment, the present invention provides novel compounds of formula I or a stereoisomer or pharmaceutically acceptable salt thereof, provided that:

a. at least one of X, X', Y, or Y' is other than H, halogen, $C_{1-6}$ alkyl, $NO_2$, $CF_3$, $NR_2$, OR, —CN, or $(CH_2)_mCO_2R$;

b. $R^1$ is other than selected from H, $C_{1-6}$ alkyl, or

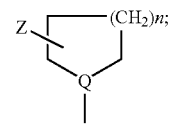

c. A is other than H, $C_{1-6}$ alkyl, and OH;

d. Z is other than H, $C_{1-6}$ alkyl, and OR;

e. Q' is selected from $CO_2R$, $(CH_2)_nCO_2R$, $CH_2O(CH_2)_nCO_2R$, $CH_2OCH_2CH=CHCO_2R$, $CH_2O(CH_2)_nPO(OR)_2$, $CONR^c{}_2$, $(CH_2)_nCONR^c{}_2$, $CH_2O(CH_2)_nCONR^c{}_2$, $CH_2OCH_2CH=CHCONR^c{}_2$, and $(CH_2)_m$tetrazole; and/or f. V is other than H, $C_{1-6}$ alkyl, $C_{2-6}$ alkenyl, $C_{2-6}$ alkynyl, $CF_3$, aryl, $CH_2OH$, or $(CH_2)_mCN$.

[2] In another embodiment, the present invention provides novel compounds of formula II or a stereoisomer or pharmaceutically acceptable salt thereof:

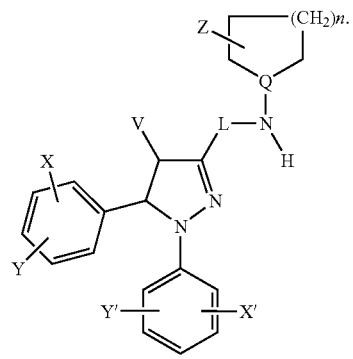

[3] In another embodiment, the present invention provides novel compounds of formula IIa or a stereoisomer or pharmaceutically acceptable salt thereof:

IIa

[4] In another embodiment, the present invention provides novel compounds of formula II, wherein:

X, X', Y, and Y' are independently selected from H, Cl, F, $C_{1-4}$ alkyl, $CF_3$, —CN, $NO_2$, $NR_2$, and OR;

Z is selected from $CO_2R$, $(CH_2)_nCO_2R$, $CH_2O(CH_2)_nCO_2R$, $(CH_2)_mC(=NH)NH_2$, $(CH_2)_mNHC(=NH)NH_2$, $NR^cCONR^c{}_2$, $NR^cCO_2R$, $(CH_2)_mNHC(=CHNO_2)NH_2$, $(CH_2)_mNHC(=NCN)NH_2$, $OCH_2CH=CHCO_2R$, $CH_2OCH_2CH=CHCO_2R$, $O(CH_2)_nPO(OR)_2$, $CH_2O(CH_2)_nPO(OR)_2$, $CONR^c{}_2$, $(CH_2)_nCONR^c{}_2$, $O(CH_2)_nCONR^c{}_2$, $CH_2O(CH_2)_nCONR^c{}_2$, $OCH_2CH=CHCONR^c{}_2$, and $CH_2OCH_2CH=CHCONR^c{}_2$;

Q is selected from N and CH;

V is selected from H, $C_{1-6}$ alkyl, $C_{2-6}$ alkenyl, $CF_3$, aryl, and $(CH_2)_mCN$;

R is selected from H, $C_{1-4}$ alkyl, and $C_{2-4}$ alkenyl; and, n is selected from 1 and 2.

[5] In another embodiment, the present invention provides novel compounds of formula II, wherein:

X and Y are independently selected from H, Cl, F, $C_{1-6}$ alkyl, $NO_2$, $CF_3$, $NR_2$, OR, —CN, $(CH_2)_mC(=NH)NH_2$, $(CH_2)_mCO_2R$, $O(CH_2)_nCO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^c{}_2$, $O(CH_2)_nC_6H_4(CH_2)_nCONR^c{}_2$, $O(CH_2)_nC_6H_4$-tetrazole, $CH_2O(CH_2)_nC_6H_4CONR^c{}_2$, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4CONR^c{}_2$, $CH_2NR^a(CH_2)_nC_6H_4CONR^c{}_2$, $NR^a(CH_2)_nC_6H_4$-tetrazole, $CH_2NR^a(CH_2)_nC_6H_4$-tetrazole, $CONR^c{}_2$, $(CH_2)_nCONR^c{}_2$, $NR^cCONR^c{}_2$, $NR^cCO_2R$, $O(CH_2)_nCONR^c{}_2$, $CH_2O(CH_2)_nCONR^c{}_2$, $NR^a(CH_2)_mCONHR^a$, $OCH_2CH=CHCONR^c{}_2$, $CH_2OCH_2CH=CHCONR^c{}_2$, $NR^aCH_2CH=CHCONR^c{}_2$, tetrazole, $O(CH_2CH_2O)_pR$, $NR^a(CH_2CH_2O)_pR$, $SONH_2$, and $SO_2NR^aCH_3$;

provided that at least one of X and Y is other than H, Cl, F, $C_{1-6}$ alkyl, —CN, $NO_2$, $CF_3$, and OR;

X' and Y' are independently selected from H, Cl, F, $C_{1-4}$ alkyl, —CN, $NO_2$, $NR_2$, and OR;

Z is selected from H, $C_{1-4}$ alkyl, and aryl;

Q is selected from N and CH;

V is selected from H, $C_{1-4}$ alkyl, aryl, $(CH_2)_mOH$, $(CH_2)_mCONH_2$, and $(CH_2)_mCN$;

R is selected from H, $C_{1-4}$ alkyl, and $C_{2-4}$ alkenyl; and, n is selected from 1 and 2.

[6] In another embodiment, the present invention provides novel compounds of formula II, wherein:

X and Y are independently selected from H, Cl, F, $C_{1-4}$ alkyl, —CN, $NO_2$, $NR_2$, and OR;

X' and Y' are independently selected from H, Cl, F, $C_{1-6}$ alkyl, —CN, $NO_2$, $CF_3$, $NR_2$, OR, $CO_2R$, $(CH_2)_nCO_2R$, $(CH_2)_mC(=NH)NH_2$, $O(CH_2)_nCO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_mCO_2R$, $NR^a(CH_2)_nPO(OR)_2$, $NR^aCH_2CH=CHCO_2R$, $NR^aSO_2CH_3$, $NR^aCO(CH_2)_nCO_2R$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^c{}_2$, $O(CH_2)_nC_6H_4(CH_2)_nCONR^c{}_2$, $O(CH_2)_nC_6H_4$-tetrazole, $CH_2O(CH_2)_nC_6H_4CONR^c{}_2$, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4CONR^c{}_2$, $CH_2NR^a(CH_2)_nC_6H_4CONR^c{}_2$, $NR^a(CH_2)_nC_6H_4$-tetrazole, $CH_2NR^a(CH_2)_nC_6H_4$-tetrazole, $CONR^c{}_2$, $(CH_2)_nCONR^c{}_2$, $NR^cCONR^c{}_2$, $NR^cCO_2R$, $O(CH_2)_nCONR^c{}_2$, $CH_2O(CH_2)_nCONR^c{}_2$, $NR^a(CH_2)_mCONHR^a$, $OCH_2CH=CHCONR^c{}_2$, $CH_2OCH_2CH=CHCONR^c{}_2$, $NR^aCH_2CH=CHCONR^c{}_2$, tetrazole, $O(CH_2CH_2O)_pR$, $NR^a(CH_2CH_2O)_pR$, $SONH_2$, and $SO_2NR^aCH_3$;

provided that at least one of X' and Y' is other than Cl, F, $C_{1-4}$ alkyl, —CN, $NO_2$, and OR;

Z is selected from H, $C_{1-4}$ alkyl, and aryl;

Q is selected from N and CH;

V is selected from H, $C_{1-4}$ alkyl, aryl, $(CH_2)_nOH$, $(CH_2)_mCONH_2$, and $(CH_2)_mCN$;

R is selected from H, $C_{1-4}$ alkyl, and $C_{2-4}$ alkenyl;

n is selected from 1 and 2; and, p is selected from 1, 2, 3, 4, 5, 6, 7, 8, 9, 10, 11 and 12.

[7] In another embodiment, the present invention provides novel compounds of formula II, wherein:

X, X', Y, and Y' are independently selected from H, $CF_3$, Cl, F, $C_{1-4}$ alkyl, —CN, $NO_2$, $NR_2$, and OR;

Z is selected from H, $C_{1-4}$ alkyl, and aryl;

Q is selected from N and CH;

V is selected from $CH_2OH$, $CH_2O(CH_2CH_2O)_pR$, $(CH_2)_mCN$, $(CH_2)_mCO_2R$, $(CH_2)_mCONR^c{}_2$, $(CH_2)_mC(=NH)NH_2$, $(CH_2)_nNHC(=NH)NH_2$, $(CH_2)_nNHC(=CHNO_2)NH_2$, $(CH_2)_nNHC(=NCN)NH_2$, $(CH_2)_mCONR^aCH(A)(CH_2)_mCO_2R$, $(CH_2)_mCONR^a(CH_2)_m$-phenyl-$(CH_2)_mCO_2R$, $(CH_2)_mCONR^a(CH_2)_m$-phenyl-$(CH_2)_m$-tetrazole, $CH_2O(CH_2)_nCONR^c{}_2$, $CH_2NR^a(CH_2)_nCONR^c{}_2$, $CH_2N^+R^b{}_3V^1$, tetrazole, and $V^1$ is selected from $Cl^-$ and $Br^-$, provided that $V^1$ is absent when $R^b$ is $O^-$;

$R^b$ is independently selected from $O^-$, $C_{1-4}$ alkyl, $C_{3-4}$ alkenyl, and $C_{3-4}$ alkynyl;

A is selected from H, $C_{1-4}$ alkyl, and $(CH_2)_m$-aryl, wherein each alkyl and aryl is optionally substituted with 0-1 groups selected from $CF_3$, Cl, F, $C_{1-4}$ alkyl, —CN, $CONR^c{}_2$, $NO_2$, $NR_2$, $NR^cCONR^c{}_2$, $NR^cCO_2R$ and OR;

R is selected from H, $C_{1-4}$ alkyl, and $C_{2-4}$ alkenyl;

m is selected from 0, 1, and 2;

n is selected from 1 and 2; and, p is selected from 1, 2, 3, 4, 5, 6, 7, 8, 9, 10, 11, and 12.

[8] In another embodiment, the present invention provides novel compounds of formula I, wherein:

X, X', Y, and Y' are independently selected from H, $CF_3$, Cl, F, $C_{1-4}$ alkyl, —CN, $NO_2$, $NR_2$, and OR;

$R^1$ is selected from $CR(CH_2OH)_2$, $C(CH_2OH)_3$, $CH(A)(CH_2)_mCONR^c{}_2$, $CH(A)(CH_2)_mC(=NH)NH_2$, $(CH)_mCH(A)(CH_2)_mCO_2R$, $(CH_2)_mCH(A)(CH_2)_mCONH(CH)_mCH(A)(CH_2)_mCO_2R$, $(CH_2)_mCH(A)(CH_2)_mCONH(CH)_mCH(A)(CH_2)_mCONH(CH)_mCH(A)(CH_2)_mCO_2R$, $(CH)_mCH(A)(CH_2)_mCONR^c{}_2$, $(CH_2)_mCH(A)(CH_2)_mCONH(CH)_mCH(A)(CH_2)_mCONR^c{}_2$, $(CH_2)_mCH(A)(CH_2)_mCONH(CH)_mCH(A)(CH_2)_mCONH(CH)_mCH(A)(CH_2)_mCONR^c{}_2$, $CH(A)(CH_2)_m$ CONH—$CH(A)(CH_2)_m$-tetrazole, $(CH_2)_m$-phenyl-$(CH_2)_mCO_2R$, $(CH_2)_m$-phenyl-$(CH_2)_mCONR^c{}_2$, $(CH_2)_m$-pyridyl-$(CH_2)_mCONR^c{}_2$, $(CH_2)_m$-phenyl-$(CH_2)_mC(=NH)NH_2$, and $(CH_2)_m$-pyridyl-$(CH_2)_m(CN)NH_2$;

A is selected from $C_{1-6}$ alkyl, $CH_2OH$, $CH(CH_3)OH$, $C(CH_3)_2OH$, $CH(OH)CH(CH_3)_2$, $CH_2C(OH)(CH_3)_2$, $(CH_2)_n$ $NHCONR^c{}_2$, $(CH_2)_nCONR^c{}_2$, $(CH_2)_m$—$C_{3-6}$-cycloalkyl, $(CH_2)_m$-phenyl, $(CH_2)_m$-aryl, and $(CH_2)_m$-heteroaryl, wherein each aryl, phenyl, and heteroaryl is optionally substituted with 0-1 groups selected from $CF_3$, Cl, F, $C_{1-4}$ alkyl, —CN, $CONR^c{}_2$, $NR^cCONR^c{}_2$, $NR^cCO_2R$, $NO_2$, $NR_2$, and OR;

V is selected from H, $C_{1-4}$ alkyl, aryl, $(CH_2)_nOH$, and $(CH_2)_m$ CN;

R is selected from H, $C_{1-4}$ alkyl; and, m is selected from 0, 1, and 2.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method of modulating the activity of CB1 receptors (e.g., peripheral CB1 receptors) in a patient, comprising: administering to a patient in need thereof a therapeutically effective amount of a compound of the present invention or a pharmaceutically acceptable salt form thereof.

In another embodiment, the present invention provides a novel method of treating a disease characterized by an inappropriate activation of peripheral CB1 receptors, comprising: administering to a patient in need thereof a therapeutically effective amount of a compound of the present invention or a pharmaceutically acceptable salt form thereof.

In another embodiment, the present invention provides a novel method for treating a disease mediated by the $CB_1$ receptor in a patient, comprising: administering to a patient in need thereof a therapeutically effective amount of a compound of the present invention or a pharmaceutically acceptable salt form thereof. In an example, the disease is mediated by peripheral $CB_1$ receptors. In another example, the $CB_1$ receptors that are blocked are peripheral $CB_1$ receptors.

In another embodiment, the present invention provides a novel method for treating a disease, comprising: administering to a patient in need thereof a therapeutically effective amount of a compound of the present invention or a pharmaceutically acceptable salt form thereof, wherein the disease is selected from obesity, diabetes, dyslipidemias, cardiovascular disorders, hepatic disorders, and a combination thereof.

In another embodiment, the diabetes disorder is selected from Type 1 diabetes, Type 2 diabetes, inadequate glucose tolerance, and insulin resistance.

In another embodiment, the hepatic disorder is selected from liver inflammation, liver fibrosis, NASH, fatty liver, enlarged liver, alcoholic liver disease, jaundice, cirrhosis, and hepatitis.

In another embodiment, the dyslipidemia disorder is selected from undesirable blood lipid levels, including low levels of high-density lipoprotein, high levels of low-density lipoprotein, high levels of triglycerides, and a combination thereof.

In another embodiment, the cardiovascular disorder is selected from atherosclerosis, hypertension, stroke and heart attack.

In another embodiment, the present invention provides a novel method for treating a co-morbidity of obesity, comprising: administering to a patient in need thereof a therapeutically effective amount of a compound of the present invention or a pharmaceutically acceptable salt form thereof.

In another embodiment, the co-morbidity is selected from diabetes, dyslipidemias, Metabolic Syndrome, dementia, cardiovascular disease, and hepatic disease.

In another embodiment, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the ovaries, cervix, uterus, breasts, prostrate, and gallbladder.

In another embodiment, the present invention also provides a method of preventing or reversing the deposition of adipose tissue in a mammal by the administration of a compound of the present invention. By preventing or reversing the deposition of adipose tissue, compound of the present invention are expected to reduce the incidence or severity of obesity, thereby reducing the incidence or severity of associated co-morbidities.

In another embodiment, the present invention provides a compound of the present invention for use in therapy.

In another embodiment, the present invention provides the use of the present invention for the manufacture of a medicament for the treatment of an indication recited herein (e.g., obesity, diabetes, dyslipidemias, cardiovascular disorders, hepatic disorders, and a combination thereof).

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperdine.

Halo" or "halogen" refers to fluoro, chloro, bromo, and iodo.

"Counterion" is used to represent a small, negatively charged species, such as chloride, bromide, hydroxide, acetate, and sulfate.

The group "$C_6H_4$" represents a phenylene.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heterocycle" refers to any stable 5, 6, or 7-membered monocyclic or bicyclic or 7, 8, 9, or 10-membered bicyclic heterocyclic ring that is saturated, partially unsaturated, or unsaturated (aromatic), and consisting of: carbon atoms and 1, 2, 3, or 4 ring heteroatoms independently selected from the group consisting of N, O and S and including any bicyclic group in which any of the above-defined heterocyclic rings is fused to a benzene ring. The N group may be N, NH, or N-substituent, depending on the chosen ring and if substituents are recited. The nitrogen and sulfur heteroatoms may optionally be oxidized (e.g., S, S(O), S(O)$_2$, and N—O). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Typically, the total number of S and O atoms in the heterocycle is not more than 1. Bridged rings are also included in the definition of heterocycle. A bridged ring occurs when one or more atoms (i.e., C, O, N, or S) link two non-adjacent carbon or nitrogen atoms. Examples of bridges include one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heterocycles, including heteroaryl, include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

"Mammal" and "patient" cover warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat obesity, diabetes, dyslipidemias, cardiovascular disorders, hepatic disorders, and a combination or comorbitity thereof, or another indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Overweight is defined as having a BMI$\geq$25. Obesity has reached epidemic proportions in the U.S., with 44 million obese Americans, and an additional eighty million deemed medically overweight.

Obesity is a disease characterized as a condition resulting from the excess accumulation of adipose tissue, especially adipose tissue localized in the abdominal area. It is desirable to treat overweight or obese patients by reducing their amount of adipose tissue, and thereby reducing their overall body weight to within the normal range for their sex and height. In this way, their risk for co-morbidities such as diabetes, dyllipidemias, and cardiovascular and hepatic diseases will be reduced. It is also desirable to prevent normal weight individuals from accumulating additional, excess adipose tissue, effectively maintaining their body weights at a BMI<25, and preventing the development of co-morbidities. It is also desirable to control obesity, effectively preventing overweight and obese individuals from accumulating additional, excess adipose tissue, reducing the risk of further exacerbating their co-morbidities.

Type 2 Diabetes or Diabetes mellitus type 2 or (formerly called non-insulin-dependent diabetes mellitus (NIDDM), or adult-onset diabetes) is a metabolic disorder that is primarily characterized by insulin resistance, relative insulin deficiency, and hyperglycemia. The World Health Organization definition of diabetes is for a single raised glucose reading with symptoms otherwise raised values on two occasions, of either fasting plasma glucose$\geq$7.0 mmol/l (126 mg/dl) or with a Glucose tolerance test: two hours after the oral dose a plasma glucose$\geq$11.1 mmol/l (200 mg/dl). Type 2 Diabetes is rapidly increasing in the developed world and there is some evidence that this pattern will be followed in much of the rest of the world in coming years. CDC has characterized the increase as an epidemic (Diabetes, Atlanta: Centres for Disease Control, Atlanta, Report no. 2007-05-24). In addition, whereas this disease used to be seen primarily in adults over age 40 (in contrast to Diabetes mellitus type 1), it is now increasingly seen in children and adolescents, an increase thought to be linked to rising rates of obesity in this age group.

Insulin resistance means that body cells do not respond appropriately when insulin is present. Unlike insulin-dependent diabetes mellitus (Type 1), the insulin resistance is generally "post-receptor", meaning it is a problem with the cells that respond to insulin rather than a problem with insulin production. Type 2 diabetes is presently of unknown etiology (i.e., origin). About 90-95% of all North American cases of diabetes are type 2, and about 20% of the population over the age of 65 has diabetes mellitus Type 2 (*Nature,* 2001, 414, 6865). Diabetes affects over 150 million people worldwide and this number is expected to double by 2025. About 55 percent of type 2 diabetics are obese-chronic obesity leads to increased insulin resistance that can develop into diabetes (*Morbidity and Mortality Weekly Report* 2008, 53, 1066). Type 2 diabetes is often associated with obesity, hypertension, elevated cholesterol (combined hyperlipidemia), and with the condition often termed Metabolic syndrome (it is also known as Syndrome X, Reavan's syndrome, or CHAOS). There are several drugs available for Type 2 diabetics, including metformin, thiazolidinediones, which increase tissue insulin sensitivity, $\alpha$-glucosidase inhibitors which interfere with absorption of some glucose containing nutrients, and peptide analogs that must be injected.

Dyslipidemia is the presence of abnormal levels of lipids and/or lipoproteins in the blood. Lipids (fatty molecules) are transported in a protein capsule, and the density of the lipids and type of protein determines the fate of the particle and its influence on metabolism. Lipid and lipoprotein abnormalities are extremely common in the general population, and are regarded as a highly modifiable risk factor for cardiovascular disease due to the influence of cholesterol, one of the most clinically relevant lipid substances, on atherosclerosis. In addition, some forms may predispose to acute pancreatitis.

In western societies, most dyslipidemias are hyperlipidemias; that is, an elevation of lipids in the blood, often due to diet and lifestyle. The prolonged elevation of insulin levels can also lead to dyslipidemia. The most prevalent hyperlipidemias include: hypercholesterolemia, characterized by elevated cholesterol (usually LDL), hypertriglyceridemia, characterized by elevated triglycerides (TGs); hyperlipoproteinemia, characterized by elevated lipoproteins; hyperchylomicronemia, characterized by elevated chylomicrons; and combined hyperlipidemia, characterized by elevated LDL and triglycerides. Abnormal decreases in the levels of lipids and/or lipoproteins in the blood also can occur. These include hypocholesterolemia, characterized by lowered cholesterol (usually high density lipoprotein, or HDL); and abetalipoproteinemia, characterized by lowered beta lipoproteins.

Dyslipidemia contributes to the development of atherosclerosis. Causes may be primary (genetic) or secondary. Diagnosis is by measuring plasma levels of total cholesterol, TGs, and individual lipoproteins. Treatment is dietary changes, exercise, and lipid-lowering drugs. A linear relation probably exists between lipid levels and cardiovascular risk, so many people with "normal" cholesterol levels benefit from achieving still lower levels. Normal and abnormal lipid levels have been defined in the Third Report of the Expert Panel on Detection, Evaluation, and Treatment of High Blood Cholesterol in Adults. National Institutes of Health, National Heart, Lung, and Blood Institute, 2001.

The treatment of choice for dyslipidemias is lifestyle change, including diet and exercise. Drugs are the next step when lifestyle changes are not effective. Lipid lowering drugs include statins, nicotinic acid, bile acid sequestrants, fibrates, cholesterol absorption inhibitors, and combination treatments (e.g., niacin and a statin). These agents are not without adverse effects, including flushing and impaired glucose tolerance (nicotinic acid), bloating, nausea, cramping, and constipation (bile acid sequestrants). Bile acid sequestrants may also increase TGs, so their use is contraindicated in patients with hypertriglyceridemia. Fibrates potentiate muscle toxicity when used with statins, and may increase LDL in patients with high TGs.

There are many kinds of hepatic (i.e., liver) diseases. Viruses cause some of them, like hepatitis A, hepatitis B and hepatitis C. Others can be the result of drugs, poisons or drinking too much alcohol. If the liver forms scar tissue because of an illness, it's called cirrhosis. Jaundice, or yellowing of the skin, can be one sign of hepatic disease. Cancer can affect the liver. Hepatic diseases such as hemochromatosis can be inherited. Additional liver diseases include nonalcohol steatohepatitis (NASH), alcoholic liver disease, cholangiocarcinoma, hepatic encephalopathy, hepatic failure, liver abscess, liver tumors, liver coagulopathy, glycogen storage diseases, portal hypertension, primary biliary cirrhosis, and primary sclerosing cholangitis.

There are few good treatment options for liver diseases. Options include lifestyle change (including diet and exercise), liver transplantation, and insertion of a transjugular intrahepatic portosystemic shunt that is placed in veins in the middle of the liver to improve blood flow to and from the organ. There are few effective drug treatment options for hepatic diseases. Interferon is an FDA-approved drug for the treatment of viral hepatitis. The chimeric protein Hyper-IL-6 dramatically enhances hepatocyte proliferation and is currently being evaluated as a pharmacological treatment for liver injury.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms (J. Clin. Invest. 1996, 97, 2517) are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport (J. Clin. Invest. 1996, 97, 2517). Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics. These include antihistamines (Drug Metab. Dispos. 2003, 31, 312), beta-adrenergic receptor antagonists (Eur. J. Clin. Pharmacol. 1985, 28, Suppl: 21; Br. J. Clin. Pharmacol., 1981, 11, 549), non-nucleoside reverse transcriptase inhibitors (NNRTIs, J. Pharm. Sci., 1999, 88, 950), and opioid antagonists. This latter group has been tested in relation to their activity in the gastrointestinal tract. These peripherally selective opioid antagonists are described in various US patents as being useful in the treatment of non-CNS pathologies in mammals, in particular those of the gastrointestinal tract [see U.S. Pat. No. 5,260,542; U.S. Pat. No. 5,434,171; U.S. Pat. No. 5,159,081; and U.S. Pat. No. 5,270,238].

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid-induced gastrointestinal side effects associated with opioid administration (J. Pharmacol. Exp. Ther. 2002, 300, 118).

The discovery that the anti-obesity activity of cannabinoid receptor blockers may in part be mediated by a non-CNS mechanism could make it beneficial for the compounds of the present invention to be peripherally restricted (i.e., have an inability or limited ability to cross the BBB, or be readily eliminated from the brain through active transport systems). It may be desirable for the compounds of the present invention to be peripherally restricted, which in turn will result in no or very limited CNS effects. Compounds that provide peripherally mediated efficacy in treating obesity, diabetes, dyslipidemias, cardiovascular disorders, hepatic disorders, a comorbitity thereof, or a combination or should result in therapeutic agents with greater safety. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects, or both.

Rosonabant (Compound IIa when X=H; Y, X', and Y'=Cl; V=H; Z=H; Q=N; L=CO, and n=2) is a drug that crosses the BBB and is indicated for the treatment of obesity. In compound AA, one of R, $R^1$, $R^2$, X, $X^1$, V and Z is a group capable of reducing or limiting the CNS activity of compound AA. This reduced or limited CNS activity occurs via at least one of R, $R^1$, $R^2$, X, $X^1$, V and Z being a group that either limits compound AA's ability to cross the BBB relative to that of rosonabant or enables it to be actively removed from the brain at a rate greater than that of rosonabant. Examples of the amount of compound AA present in the brain can include (a) from 50, 55, 60, 65, 70, 75, 80, 85, 90, 91, 92, 93, 94, 95, 96, 97, 98, 99, to 100% lower than rosonabant, (b) from 90, 91, 92, 93, 94, 95, 96, 97, 98, 99, to 100% lower than rimonabant, and (c) from 98, 99, to 100% lower than rimonabant, when administered at the same dosage.

The compounds of the present invention are expected to be cannabinoid receptor antagonists or inverse agonists (e.g., have activity at $\leq 10$ µM). Representative compounds have been tested and shown to be active (e.g., see Tables A, B, and C).

An inverse agonist is a compound that not only blocks the action of the endogenous agonist at the receptor, but also exhibits its own activity which is usually the opposite of that shown by the agonist. Inverse agonists are also effective against certain types of receptors (e.g. certain histamine receptors/GABA receptors) that have intrinsic activity without the interaction of a ligand upon them (also referred to as 'constitutive activity').

Most methods of treating obesity are dependent on a significant reduction in energy intake, either by a decrease in food intake (e.g., sibutramine) or by inhibition of fat absorption (e.g., orlistat). In the present invention, adipose tissue may be reduced in the absence of a significant reduction in food intake. The weight loss, as a result of the present invention, comes from the treatment with a compound of the present invention, largely independent of, though not totally dissociated from, appetite and food intake. It can be desirable that adipose tissue loss occurs while food intake is maintained, increased or (a) about 1, 2, 3, 4, 5, 6, 7, 8, 9, 10, 11, 12, 13, 14, 15, 16, 17, 18, 19, or 20% below the normal range of the subject prior to being treated in accordance with the present invention (i.e., its pre-administration level), (b) about 1, 2, 3, 4, 5, 6, 7, 8, 9, 10, 11, 12, 13, 14, or 15% below its pre-administration level, (c) about 1, 2, 3, 4, 5, 6, 7, 8, 9, or 10% below its pre-administration level, or (d) about 1, 2, 3, 4, or 5% below its pre-administration level.

In some cases, loss of adipose tissue can be accompanied by a concomitant loss of lean muscle mass. This is particularly evident in cancer patients who show a generalized wasting of body tissues, including adipose tissue and lean muscle mass. In the present invention, however, it can be desirable for body fat to be significantly reduced in the absence of a significant reduction in lean body mass. Adipose tissue loss comes from treatment with a compound of the present invention, independent of a significant change in lean body mass. Thus, adipose tissue loss can occur while lean body mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

In some cases, loss of adipose tissue can be accompanied by a concomitant loss of water mass. This is particularly evident with diet regimens that promote dehydration. In the present invention, it can be desirable for body fat to be significantly reduced in the absence of a significant reduction in water mass. In other words, adipose tissue loss comes from treatment with a compound of the present invention, independent of a significant change in water mass. It can be desirable that adipose tissue loss occurs while water mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

Sibutramine and orlistat are currently marketed for use in the treatment of obesity, albeit weight loss is achieved through entirely different mechanism of action. Sibutramine inhibits the neuronal reuptake of serotonin and noradrenaline, and orlistat inhibits gut lipase enzymes that are responsible for breaking down ingested fat.

Cannabinoid receptor blockers can promote weight loss through inhibition of peripheral cannabinoid receptors, a mechanism entirely different from appetite suppressants, gut lipase inhibitors, and other agents with similar indications (e.g., serotonin agonists, leptin, fatty acid synthase inhibitors, and monoamine oxidase (MAO) inhibitors). Co-administration of a cannabinoid receptor blocker together with one or more other agents that are useful for treating the indications described above (e.g., obesity, diabetes, dyslipidemias, cardiovascular disorders, hepatic disorders, and a combination thereof) is expected to be beneficial, by producing, for example, either additive or synergistic effects. Examples of additional agents include an appetite suppressant, a lipase inhibitor, and a MAO inhibitor (e.g., MAO-B and a combination of MAO-A/B). Therefore, the present invention provides a method of treating obesity, diabetes, dyslipidemias, cardiovascular disorders, and/or hepatic disorders, and a combination thereof, comprising administering a therapeutically effective amount of a compound of the present invention and a second component effective for treating the desired indication.

Examples of second components include anti-obesity agents, which include, but are not limited to: 1) growth hormone secretagogues; 2) growth hormone secretagogue receptor agonists/antagonists; 3) melanocortin agonists; 4) Mc4r (melanocortin 4 receptor) agonists; 5) .beta.-3 agonists; 7) 5HT2C (serotonin receptor 2C) agonists; 8) orexin antagonists; 9) melanin concentrating hormone antagonists; 10) melanin-concentrating hormone 1 receptor (MCH1R) antagonists; 11) melanin-concentrating hormone 2 receptor (MCH2R) agonist/antagonists; 12) galanin antagonists; 13) CCK agonists; 14) CCK-A (cholecystokinin-A) agonists; 16) corticotropin-releasing hormone agonists; 17) NPY 5 antagonists; 18) NPY 1 antagonists; 19) histamine receptor-3 (H3) modulators; 20) histamine receptor-3 (H3) blockers; 21)β-hydroxy steroid dehydrogenase-1 inhibitors (.beta.-HSD-1); 22) PDE (phosphodiesterase) inhibitors; 23) phosphodiesterase-3B (PDE3B) inhibitors; 24) NE (norepinephrine) transport inhibitors; 25) non-selective serotonin/norepinephrine transport inhibitors, such as sibutramine, phentermine, or fenfluramine; 26) ghrelin antagonists; 28) leptin derivatives; 29) BRS3 (bombesin receptor subtype 3) agonists; 30) CNTF (Ciliary neurotrophic factors); 31) CNTF derivatives, such as axokine (Regeneron); 32) monoamine reuptake inhibitors; 33) UCP-1 (uncoupling protein-1), 2, or 3 activators; 34) thyroid hormone .beta. agonists; 35) FAS (fatty acid synthase) inhibitors; 37) DGAT2 (diacylglycerol acyltransferase 2) inhibitors; 38) ACC2 (acetyl-CoA carboxylase-2) inhibitors; 39) glucocorticoid antagonists; 40) acyl-estrogens; 41) lipase inhibitors, such as orlistat (Xenical®); 42) fatty acid transporter inhibitors; 43) dicarboxylate transporter inhibitors; 44) glucose transporter inhibitors; 45) phosphate transporter inhibitors; 46) serotonin reuptake inhibitors; 47) Metformin (Glucophage®); 48) Topiramate (Topimax®); 49) opiate antagonists such as naltrexone, 50) the non-selective transport inhibitor bupropion, and/or 51) MAO inhibitors.

Examples of MAO inhibitors include Moclobemide; Brofaromine; BW A616U; Ro 41-1049; RS-2232; SR 95191; Harmaline; Harman; Amiflamine; BW 1370U87; FLA 688; FLA 788; Bifemelane; Clorgyline; LY 51641; MDL 72,394; 5-(4-Benzyloxyphenyl)-3-(2-cyanoethyl)-(3H)-1,3,4-oxadiazol-2-one; 5-(4-Arylmethoxyphenyl)-2-(2-cyanoethyl) tetrazoles; Lazabemide; Ro 16-6491; Almoxatone; XB308; RS-1636; RS-1653; NW-1015; SL 340026; L-selegiline; Rasagiline; Pargyline; AGN 1135; MDL 72,974; MDL 72,145; MDL 72,638; LY 54761; MD 780236; MD 240931; Bifemelane; Toloxatone; Cimoxatone; Iproniazid; Phenelzine; Nialamide; Phenylhydrazine; 1-Phenylcyclopropylamine; Isocarboxazid; and, Tranylcypromine. Additional examples of MAO inhibitors can be found in USPA 2007/0004683; U.S. application Ser. No. 11/445,044; USPA 2007/0015734; and U.S. application Ser. No. 11/424,274.

Examples of diabetes disorders include treating Type 1 diabetes, Type 2 diabetes, inadequate glucose tolerance, and insulin resistance.

Examples of second components useful for treating diabetes include (a) insulin sensitizers including (i) PPAR-γ agonists such as the glitazones (e.g. troglitazone, pioglitazone, englitazone, MCC-555, rosiglitazone), and compounds disclosed in WO97/27857, 97/28115, 97/28137, and 97/27847; and (ii) biguanides such as metformin and phenformin; (b) insulin or insulin mimetics; (c) sulfonylureas such as tolbutamide and glipizide, or related materials; (d) α-glucosidase inhibitors (e.g., acarbose); (e) cholesterol lowering agents such as (i) HMG-CoA reductase inhibitors (lovastatin, simvastatin, pravastatin, fluvastatin, atorvastatin, rivastatin, and other statins), (ii) sequestrants (e.g., cholestyramine, colestipol, and dialkylaminoalkyl derivatives of a cross-linked dextran), (iii) nicotinyl alcohol, nicotinic acid or a salt thereof, (iv) PPAR-α agonists (e.g., fenofibric acid derivatives including gemfibrozil, clofibrate, fenofibrate, and bezafibrate), (v) inhibitors of cholesterol absorption (e.g., β-sitosterol) and acyl CoA:cholesterol acyltransferase inhibitors (e.g., melinamide), and (vi) probucol; (f) PPAR-α/γ agonists; (g) antiobesity compounds (described previously); (h) ileal bile acid transporter inhibitors; (i) insulin receptor activators, (j) dipeptidyl peptidase IV, or DPP-4 inhibitors (sitagliptin, vildagliptin and other DPP-4 inhibitors (k) exenatide, (l) pramLintide, (m) FBPase inhibitors, (n) glucagon receptor antagonists, (o) glucagon-like peptide-1, and (p) the glucagon-like peptide-1 analogues (liraglutide, and others).

The compounds of the present invention are expected to be CB1 receptor blockers and are expected to be useful for treating diseases mediated by the $CB_1$ receptor. The compounds of the present are expected to possess an affinity in vitro for the central and/or peripheral cannabinoid receptors under the experimental conditions described by Devane et al., *Molecular Pharmacology*, 1988, 34, 605-613. The compounds according to the invention are also expected to possess an affinity for the cannabinoid receptors present on preparations of electrically stimulated isolated organs. These tests can be performed on guinea-pig ileum and on mouse vas deferens according to Roselt et al., *Acta Physiologica Scandinavia* 1975, 94, 142-144, and according to Nicolau et al., *Arch. Int. Pharmacodyn*, 1978, 236, 131-136.

CB1 receptor affinities can be determined using membrane preparations of Chinese hamster ovary (CHO) cells in which the human cannabinoid CB1 receptor is stably transfected (*Biochem J.* 1991, 279, 129-134) in conjunction with [3H] CP-55,940 as radioligand. After incubation of a freshly prepared cell membrane preparation with the [3H]-radioligand, with or without addition of test compound, separation of bound and free ligand is performed by filtration over glass fiber filters. Radioactivity on the filter is measured by liquid scintillation counting. The $IC_{50}$ values can be determined from at least three independent measurements.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal); subdermal implants; and, buccal, sublingual, topical, rectal, vaginal, and intranasal administrations. Bioerodible, non-bioerodible, biodegradable, and non-biodegradable systems of administration may also be used. Examples of oral formulations include tablets, coated tablets, hard and soft gelatin capsules, solutions, emulsions, and suspensions.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example $\alpha$-, $\beta$-, or $\gamma$-cyclodextrin, 2-hydroxypropyl-$\beta$-cyclodextrin, and/or methyl-$\beta$-cyclodextrin.

The dose of the compound of the present invention administered daily will vary on an individual basis and to some extent may be determined by the severity of the disease being treated (e.g., obesity, diabetes, dyslipidemias, cardiovascular disorders, and hepatic disorders). The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Tablet |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Tablet |
| --- | --- |
| Active substance | 1.0 mg |
| 1N HCl | 20.0 µl |
| acetic acid | 0.5 mg |
| NaCl | 8.0 mg |
| Phenol | 10.0 mg |
| 1N NaOH | q.s. ad pH 5 |
| H$_2$O | q.s. ad 1 mL |

Synthesis

The compounds of the present invention can be prepared in numerous ways known to one skilled in the art of organic synthesis through construction of the pyrazoline carboxylic acid with various substituents on the heterocyclic nucleus. Methods for the construction of this variably substituted pyrazoline carboxylic acids are cited in various literature publications and published patent or patent applications (e.g., see EP 1743888, 1743889; *Synthetic Communications*, 26 2229 (1996); Tetrahedron, 81, 5235 (2005); Tetrahedron Asymmetry, 12, 1923 (2001); U.S. Pat. No. 6,028,084; US Patent Application No. 2007/0073056; and EP2006/006961). The respective descriptions are hereby incorporated by reference and form part of the disclosure. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

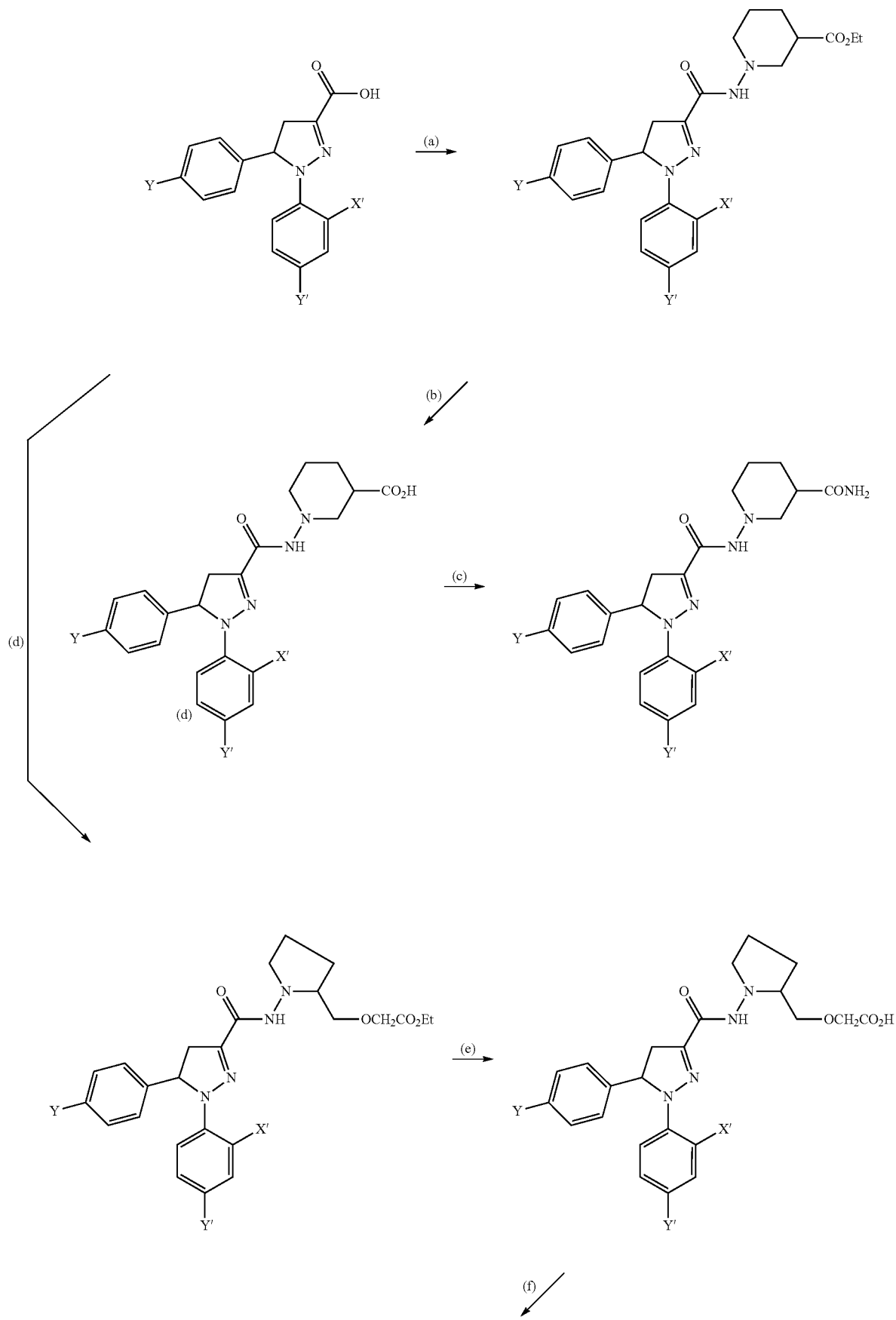

-continued

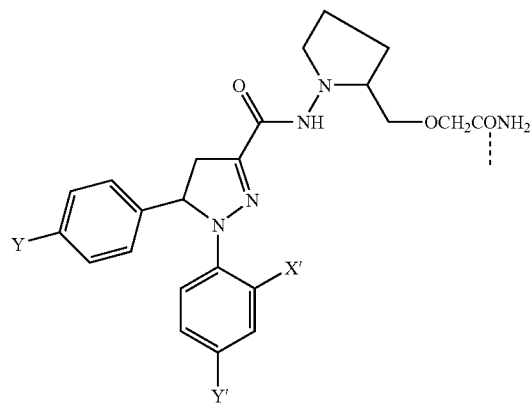

Scheme 1 shows how an appropriately substituted pyrazoline carboxylic acid, upon conversion to the acid chloride using thionyl chloride and subsequent treatment with ethyl N-aminonipecotate, should afford the hydrazide ester (step a). Hydrolysis of the ester with lithium hydroxide and acidification with dilute hydrochloric acid solution should yield the hydrazide carboxylic acid (step b). Treatment of this acid with thionyl chloride followed by ammonia should afford the carboxamide (step c).

Alternatively, the acid chloride generated from the product of step c can be treated with N-amino-2-pyrrolidine methanol O—CH$_2$CO$_2$Et derivative to produce the hydrazide ester (step d). Subsequent hydrolysis of this ester with aqueous base should afford the carboxylic acid (step e), and treatment as above with thionyl chloride and ammonia should produce the carboxamide (step f)

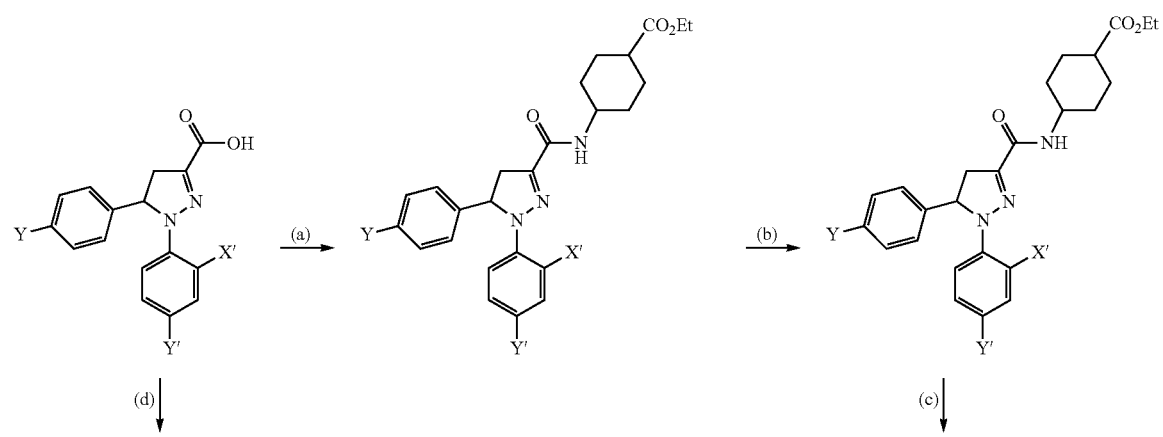

Scheme 2

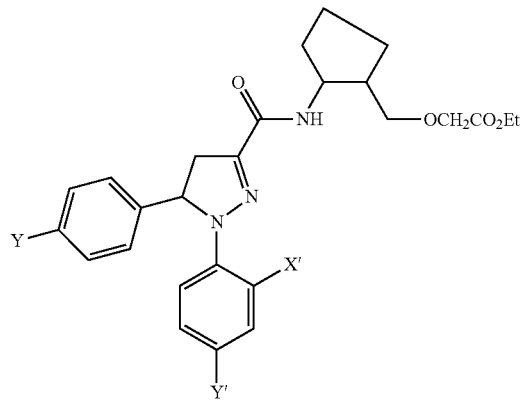
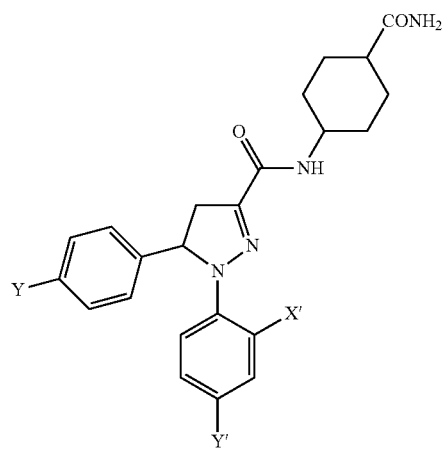

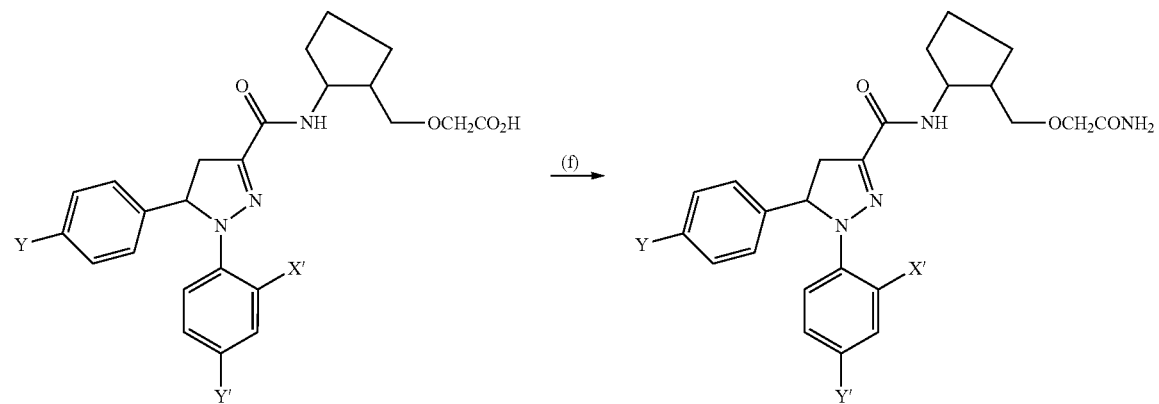

Scheme 2 describes how the conversion of a pyrazoline carboxylic acid to its acid chloride using thionyl chloride or oxalyl chloride in dichloroethane at elevated temperatures followed by treatment with ethyl 4-aminocyclohexane carboxylate in the presence of triethyl amine should afford the amide ester (step a). Hydrolysis of the ester with lithium hydroxide and acidification with dilute hydrochloric acid solution should yield the amide carboxylic acid (step b). When this acid is further treated with Boc anhydride (Boc$_2$O) in THF in the presence of pyridine, followed by a solution of ammonia in THF at 0° C. to ambient temperature, the carboxamido compound should be produced (step c).

Alternatively, a pyrazoline acid chloride can be treated with 2-amino-cyclopentylmethanol-OCH$_2$CO$_2$Et derivative to produce the amide ester (step d). Subsequent hydrolysis of this ester with aqueous base should afford the carboxylic acid (step e). Treatment as previously described should also afford the carboxamide (step f).

Scheme 3

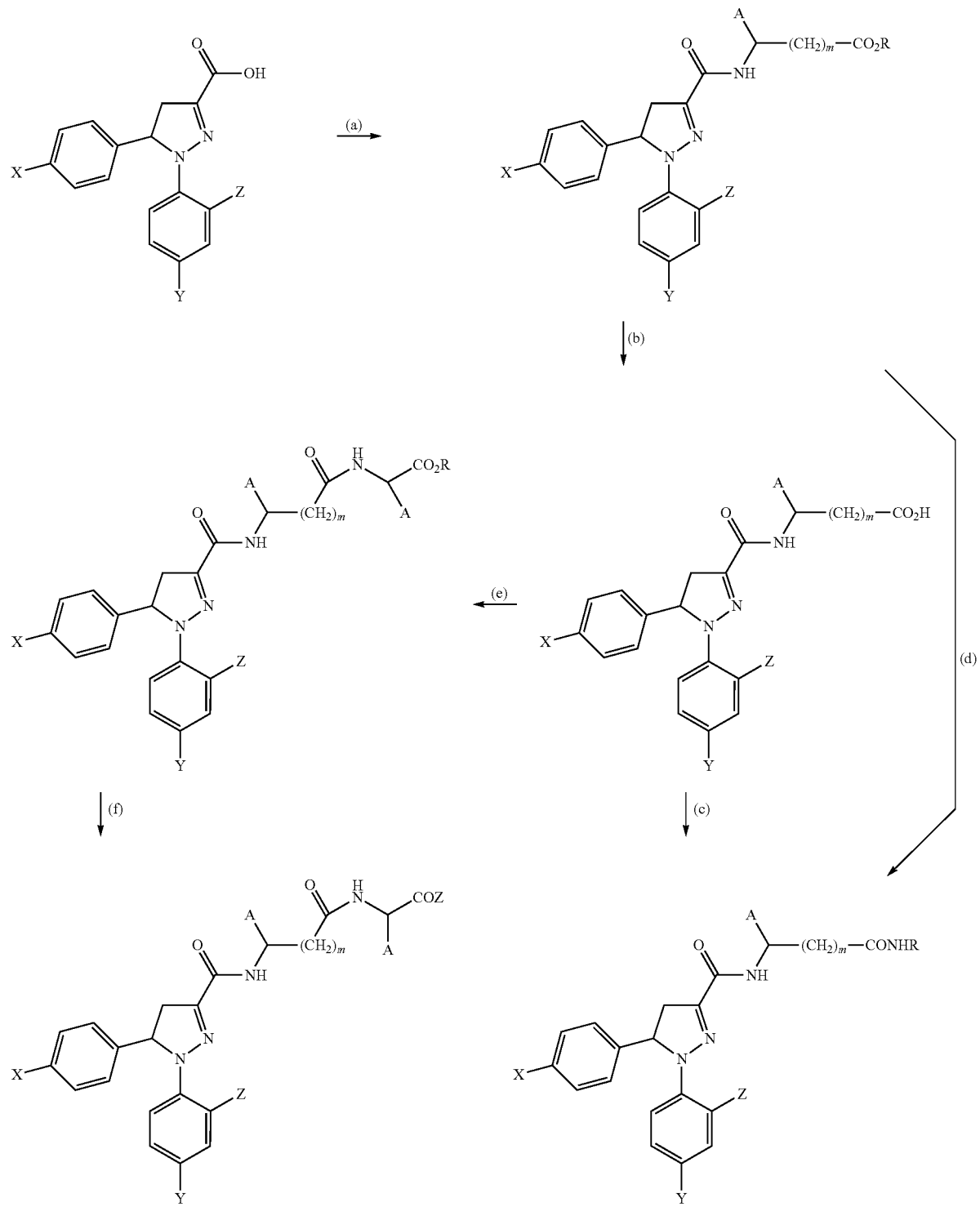

Scheme 3 depicts the conversion of a pyrazoline carboxylic acid to its acid chloride using thionyl chloride or oxalyl chloride in dichloroethane at ambient to elevated temperatures followed by treatment with an amine such as alanine ethyl ester (A=methyl, m=0) in the presence of an amine such as triethylamine or N-methylmorpholine to afford the amide ester (step a). Hydrolysis of the ester with lithium hydroxide in aqueous THF solution and acidification with dilute hydrochloric acid solution should yield the amide carboxylic acid (step b). This acid can be further treated with Boc anhydride (Boc$_2$O) in THF in the presence of pyridine, followed by a solution of ammonia in THF at 0° C. to ambient temperature to yield the carboxamido compound (step c, R=H). Treatment of the acid with isobutylchloroformate (IBCF) in dichloromethane in the presence of N-methylmorpholine (NMM) at 0 to −15° C. followed by hydroxylamine hydrochloride at low temperature to ambient temperature should afford the hydroxamic acid (step c, R=OH). Alternatively, the ester from step a can be directly converted to the amide by treatment with ammonia or other primary amines in THF or MeOH at ambient or elevated temperature (step d). Treatment of the acid with IBCF in dichloromethane in the presence of NMM followed by condensation with an amino ester such as ethyl glycine should also produce the dipeptide adduct (step e). Hydrolysis or amidolysis as described above should give the acid or amide, respectively (step f, Z=OH or NH$_2$). The carboxylic acid can also be treated, as described above, to produce the hydroxamic acid (step f, Z=NHOH).

Scheme 4

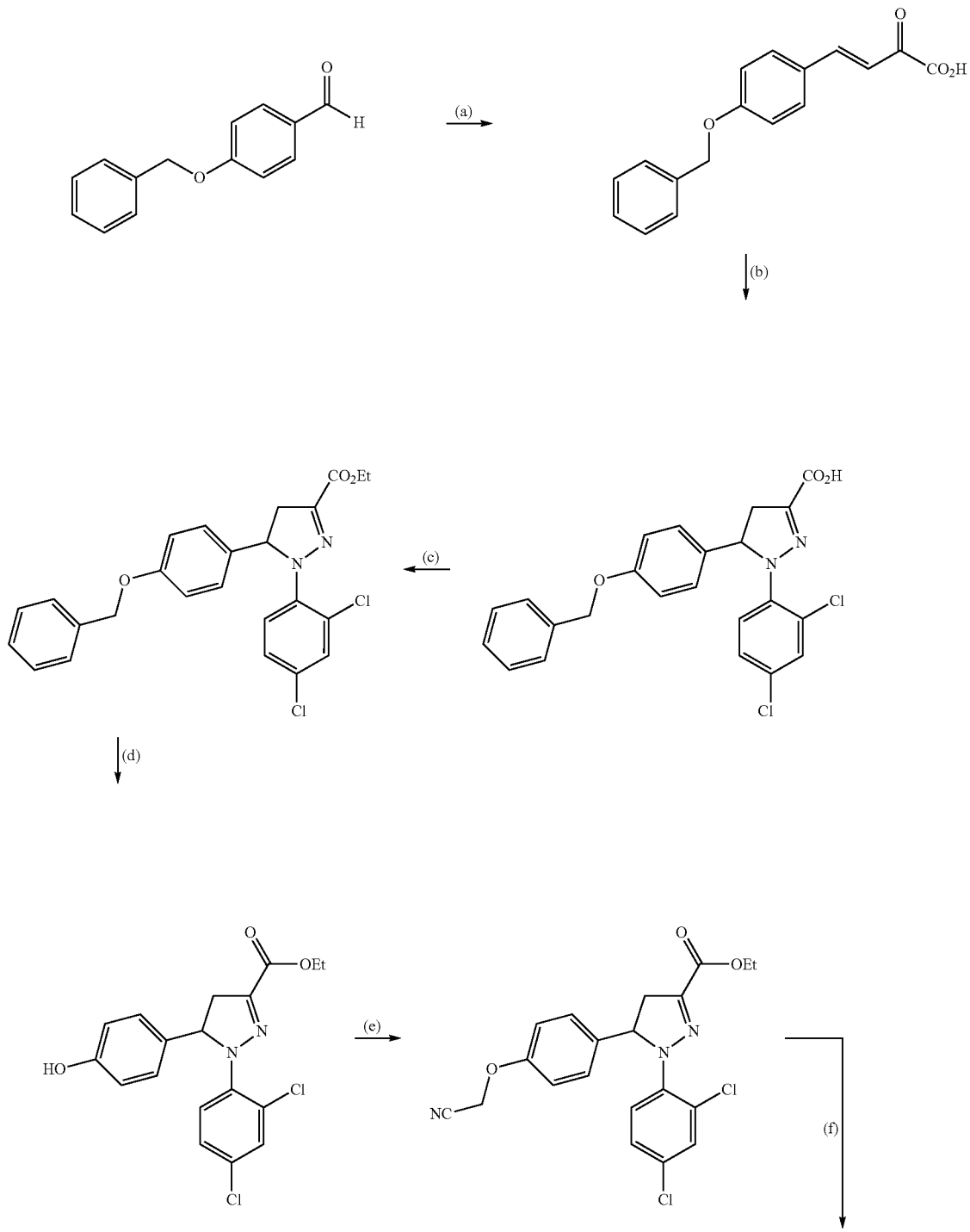

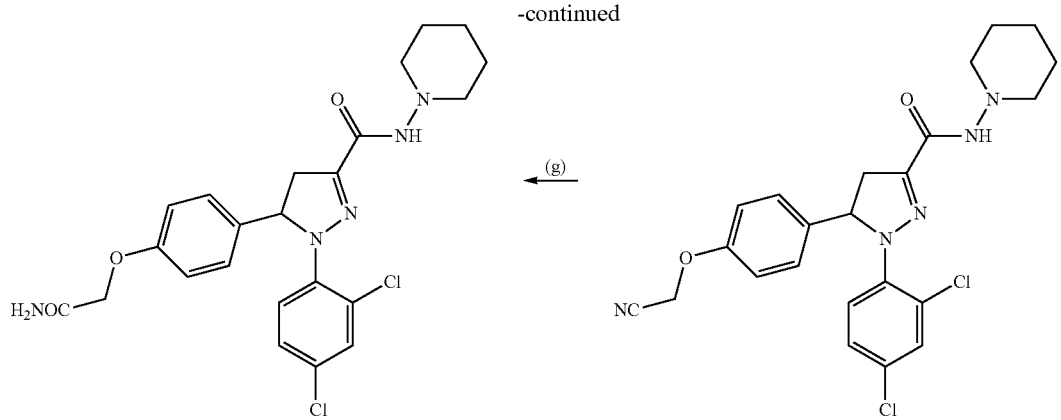

Scheme 4 illustrates how the treatment of 4-benzyloxybenzaldehyde with ethyl pyruvate in aqueous ethanol solution in the presence of sodium hydroxide at 0° to room temperature over a several hour period should afford, after acidification with hydrochloric acid solution, the oxobutenoic acid (step a). Treatment of the acid with 2,4-dichlorophenyl hydrazine in glacial acetic acid at elevated temperatures for several hours should produce the pyrazoline carboxylic acid (step b). The acid can be esterified with ethanol in the presence of an acid such as sulfuric acid (step c). Removal of the benzyl group via treatment with TFA (step d) and alkylation of the resulting phenol with bromoacetonitrile in the presence of a base, such as potassium carbonate, in a solvent such as DMF at elevated temperature should produce the ether (step e). Hydrolysis of the ester using lithium hydroxide and aqueous THF as described above and subsequent conversion of the carboxylic acid to the acid chloride using thionyl chloride followed by treatment with N-aminopiperidine should afford the hydazide (step f). The nitrile can be converted to the carboxamide using hydrogen peroxide in DMSO containing potassium carbonate (step g).

Scheme 5

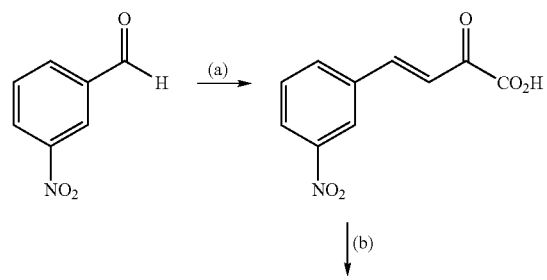

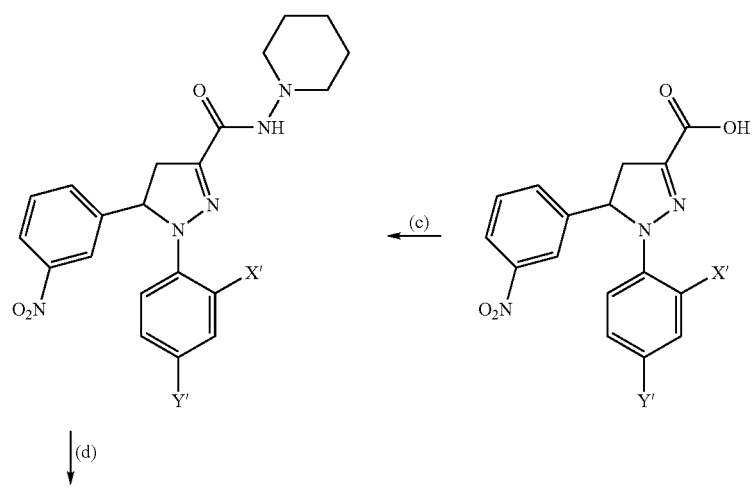

-continued

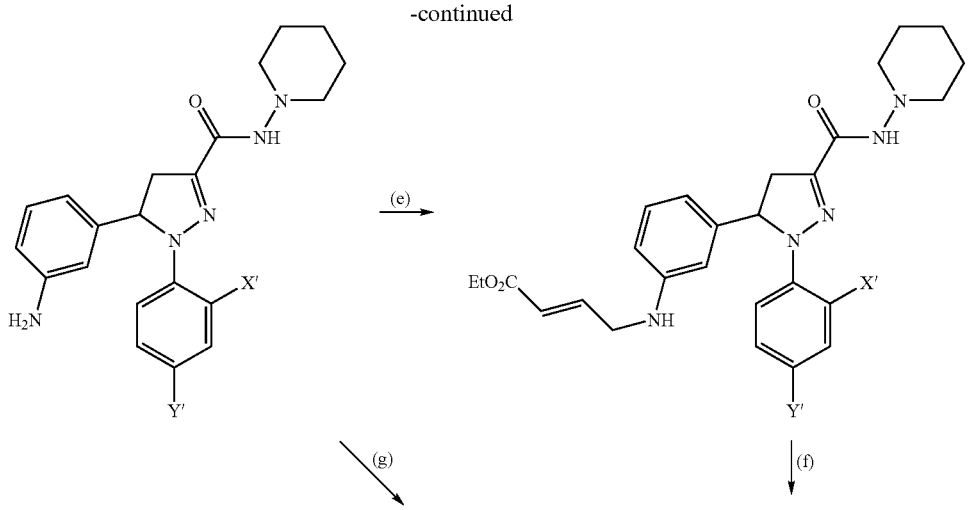

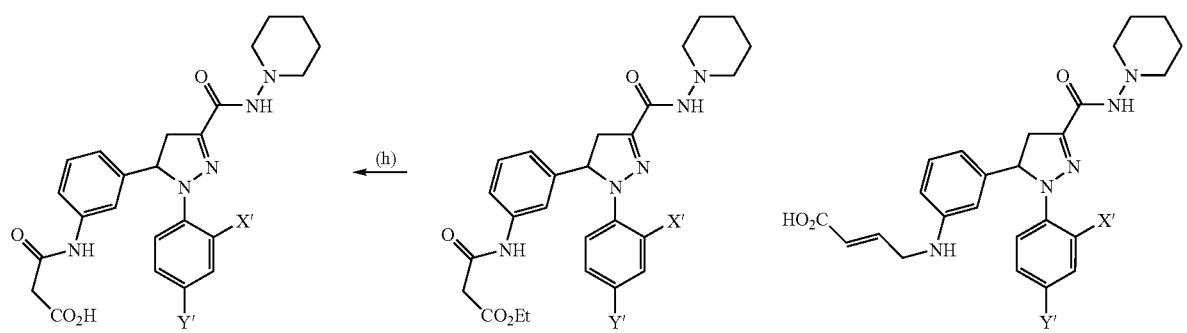

Scheme 5 shows how the treatment of 3-nitrobenzaldehyde with ethyl pyruvate in aqueous ethanol solution in the presence of sodium hydroxide at 0° to room temperature over a 2-4 hour period should afford, after acidification with hydrochloric acid solution, the oxobutenoic acid (step a). Treatment of the acid with 2,4-dichlorophenyl hydrazine in glacial acetic acid at elevated temperatures for several hours should produce the pyrazoline carboxylic acid (step b). Subsequent conversion of the carboxylic acid to the acid chloride using thionyl chloride followed by treatment with N-aminopiperidine should afford the hydazide (step c). The nitro compound can be reduced using sodium dithionite in aqueous dioxane containing concentrated ammonium hydroxide solution to give the aniline (step d). Reaction of the aniline with ethyl 4-bromocrotonate in acetone at reflux in the presence of potassium carbonate should afford the ester (step e). Hydrolysis of the ester with lithium hydroxide in aqueous THF solution, and acidification with dilute hydrochloric acid solution should yield the carboxylic acid (step f).

Alternatively, the aniline can be treated with ethyl malonyl chloride in the presence of base to yield the ester (step g). The ester can then be hydrolyzed with lithium hydroxide in aqueous THF solution, and after acidification with dilute hydrochloric acid solution should yield the hydrazide carboxylic acid (step h). In both cases, the carboxylic acid products can also be converted to carboxamides using thionyl chloride and ammonia as described above.

Scheme 6

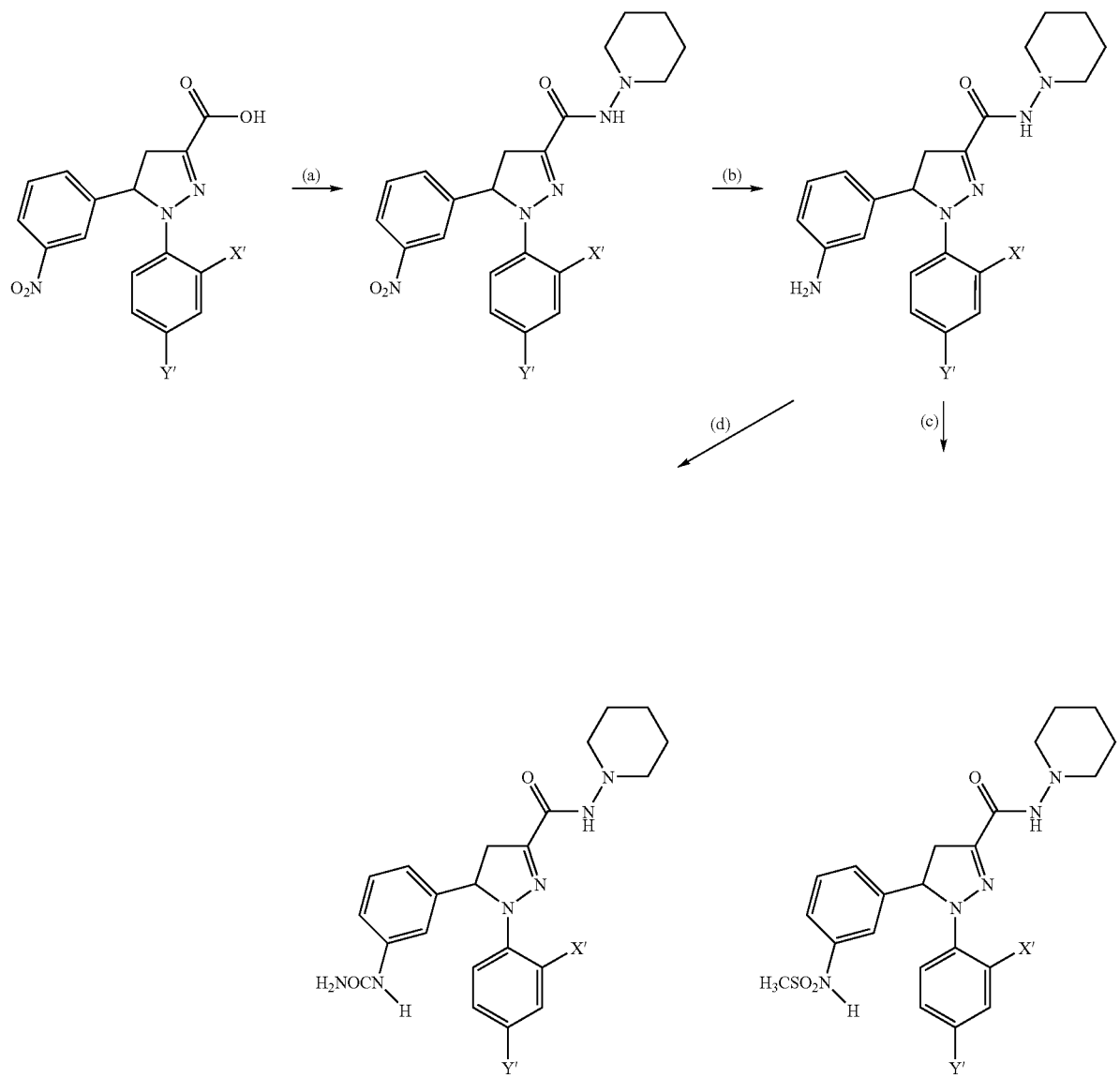

Scheme 6 describes how the conversion of the pyrazoline carboxylic acid of Scheme 5 to its acid chloride using thionyl chloride followed by treatment with N-aminopiperidine should afford the hydazide (step a). The nitro compound can be reduced to the aniline using sodium dithionite in aqueous dioxane containing concentrated ammonium hydroxide solution to give the aniline (step b). Reaction of the aniline with methanesulfonyl chloride in the presence of base should afford the sulfonamide (step c). Alternatively, treatment of the aniline with sodium cyanate in aqueous acetic acid solution at room or slightly elevated temperatures should produce the urea (step d).

Scheme 7

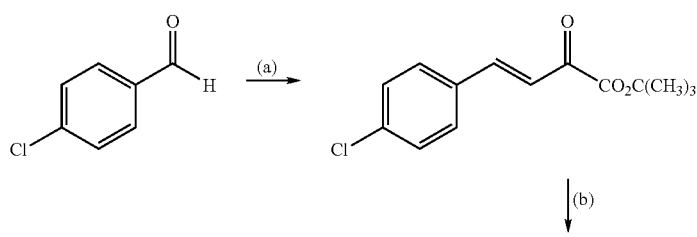

-continued

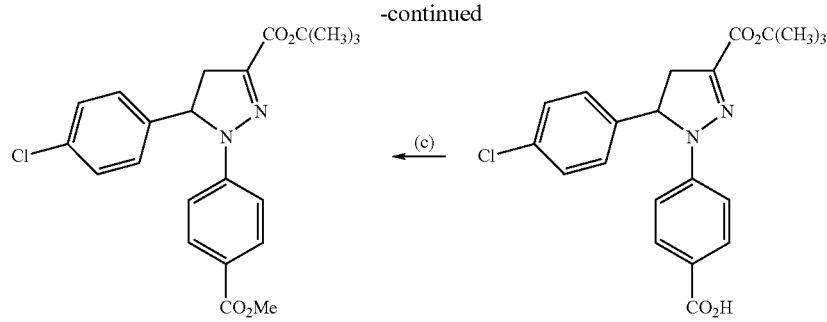

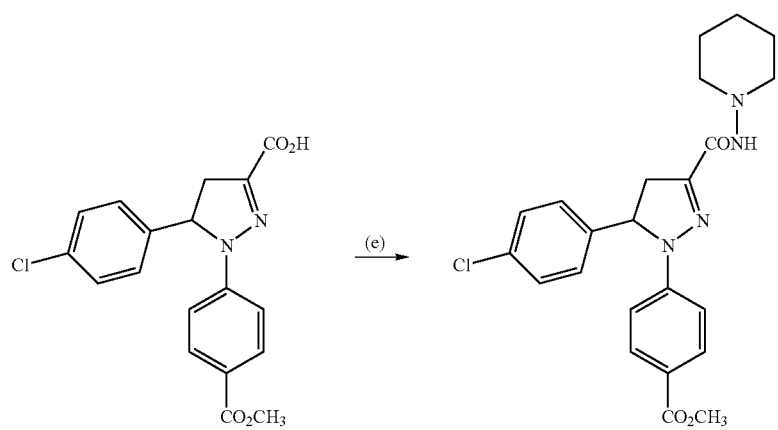

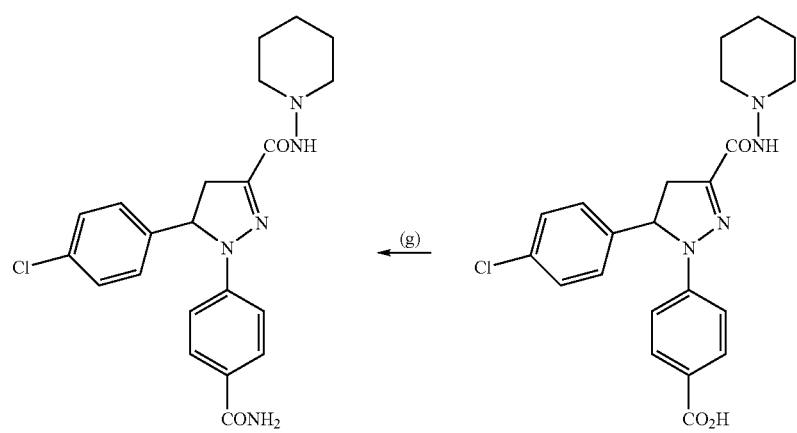

Scheme 7 depicts how the condensation of a benzaldehyde with ethyl-t-butyl oxalate in the presence of base, such as lithium hexamethydisilazide in a solvent such as ether or THF at 0° to room temperature, should afford, after acidification with hydrochloric acid solution, the keto-ester (step a). Heating this keto-ester with 4-hydrazinobenzoic acid in a solvent such as toluene or ethylene glycol diethyl ether containing glacial acetic acid at elevated temperatures for several hours should produce the pyrazoline ester (step b). Esterification of the benzoic acid with diazomethane in methanol solution should give the methyl ester (step c) which upon further treatment with trifluoroacetic acid in methylene chloride, should afford the pyrazoline carboxylic acid (step d). Subsequent conversion of the carboxylic acid to the acid chloride using thionyl chloride followed by treatment with N-aminopiperidine should afford the hydazide ester (step e). Hydrolysis of the remaining ester with lithium hydroxide in aqueous THF solution, and acidification with dilute hydrochloric acid solution should yield the hydrazide carboxylic acid (step f). The carboxylic acid can then be treated with thionyl chloride followed by ammonia to produce the carboxamido compound (step g).

Scheme 8

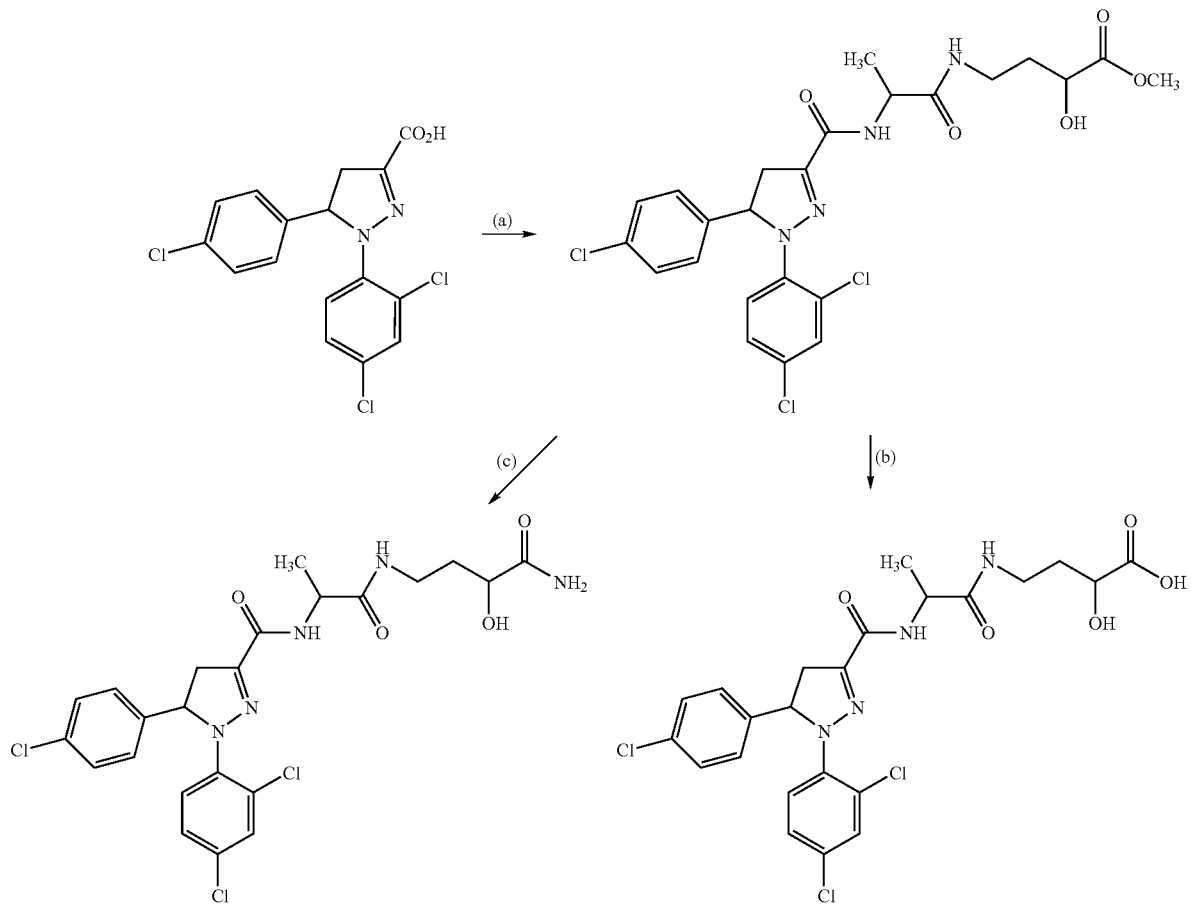

Scheme 8 illustrates an alternate method of converting a pyrazoline carboxylic acid to a di-amino acid adduct. Reacting a carbobenzyloxy (CBZ) protected amino acid such as alanine with an amino acid ester such as 4-amino-2-hydroxy-butyric acid methyl ester in methylene chloride in the presence isobutylchloroformate and N-methylmorpholine (NMM) at −15° C. to room temperature should give the diamino acid adduct. The CBZ-group can then be removed through hydrogenolysis over Pd/C in methanol. Treatment of this amino ester with a pyrazoline carboxylic acid chloride in dichloromethane in the presence of NMM at zero° C. to room temperature should afford the di-amino ester adduct (step a). Hydrolysis of the ester with lithium hydroxide in aqueous THF solution, and acidification with dilute hydrochloric acid solution should yield the hydroxy carboxylic acid (step b). Alternatively, the ester can be treated with ammonia in methanol to yield the carboxamide (step c).

Scheme 9

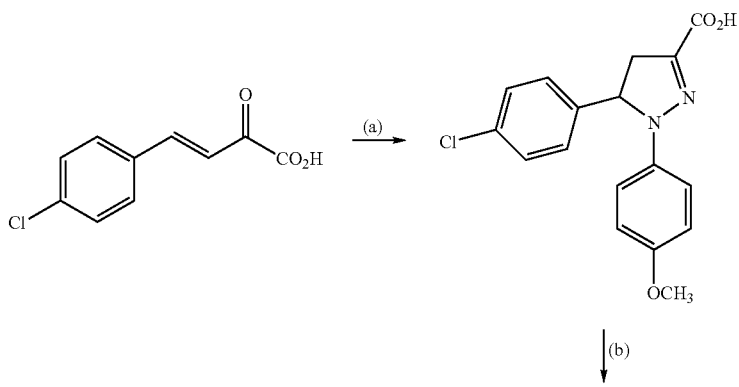

-continued

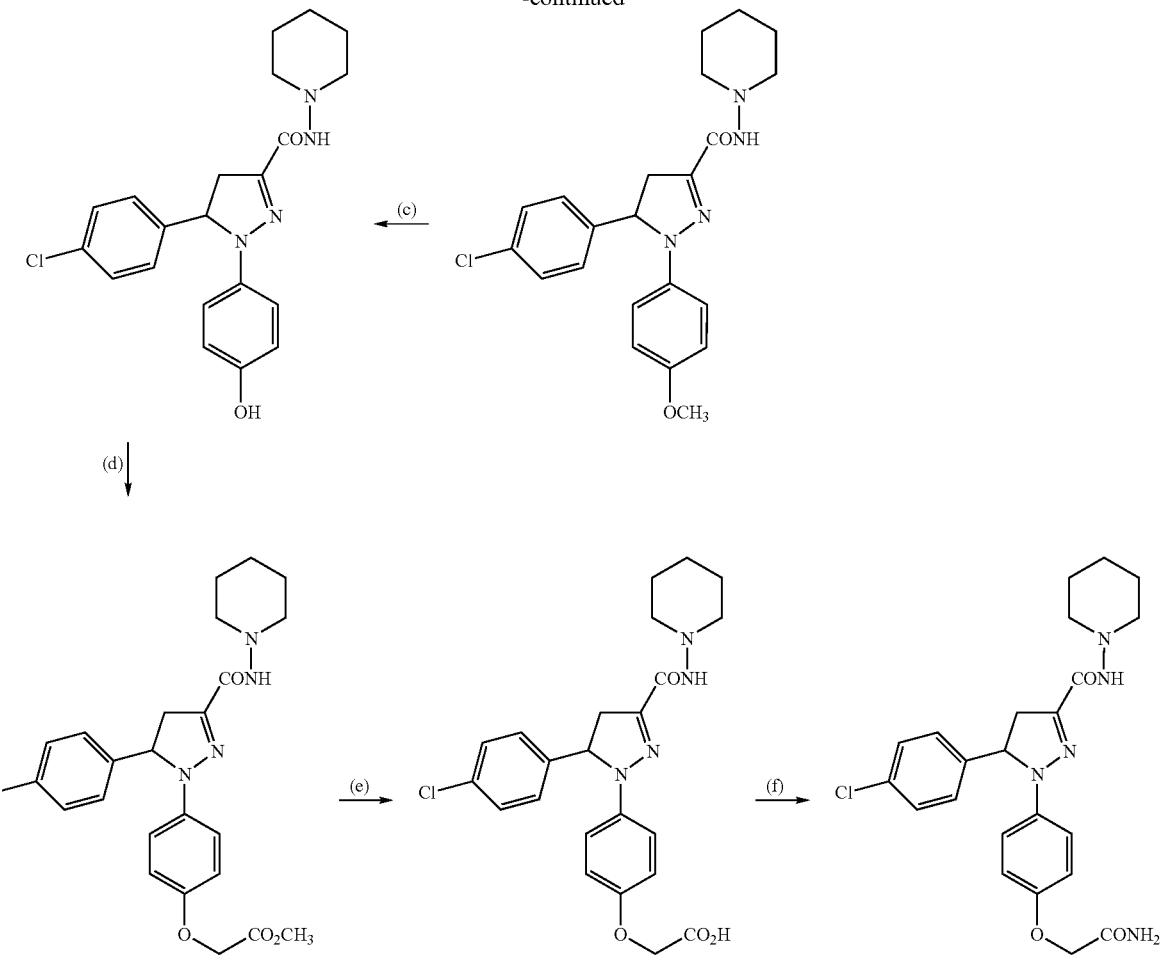

Scheme 9 shows how the treatment of a oxobutenoic acid, prepared as described in Scheme 4, with 4-methoxyphenyl-hydrazine in a solvent such as glacial acetic acid at elevated temperatures for several hours should produce the pyrazoline carboxylic acid (step a). The acid can be converted to the acid chloride using thionyl chloride followed by treatment with N-aminopiperidine to afford the hydrazide (step b). Demethylation of the ether can be achieved using $BBr_3$ or TMAH/$Al_2Cl_7$ (see European Journal Org Chem, 1681(2003)) in methylene chloride at reflux. (step c). Alkylation of the phenol using ethyl bromoacetate in acetone in the presence of potassium carbonate at room temperature to reflux should afford the ester (step d). Hydrolysis of the ester with lithium hydroxide in aqueous THF solution, and acidification with dilute hydrochloric acid solution should yield the carboxylic acid (step e). The carboxylic acid can then be treated with isobutylchloroformate followed by ammonia to produce the aryloxyacetamide (step f).

Scheme 10

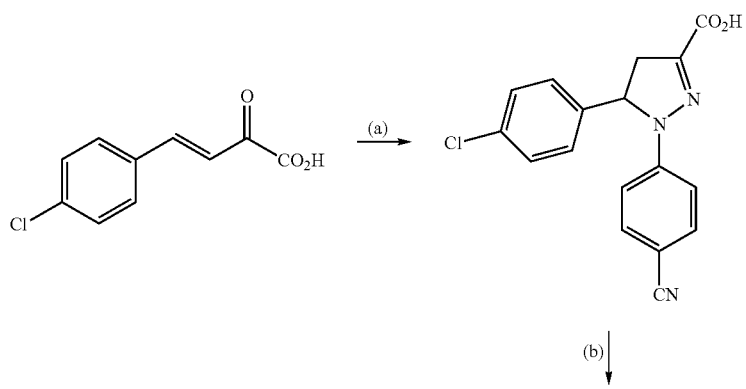

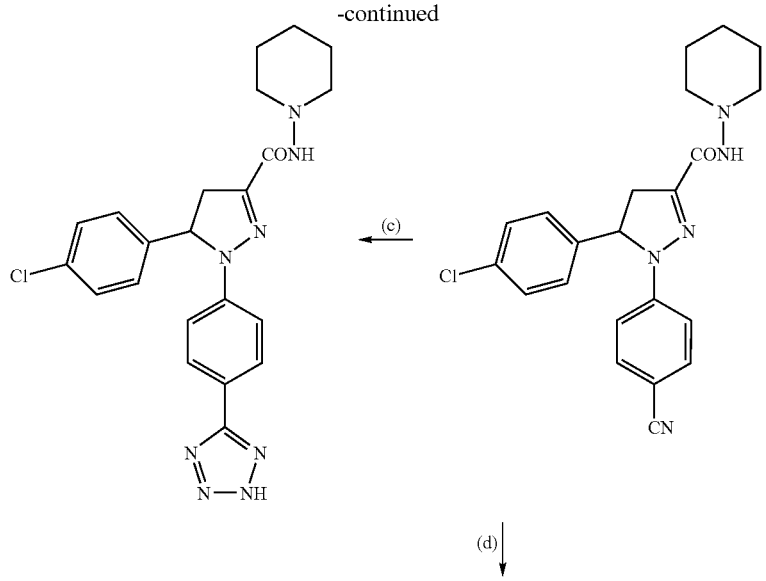

(d)

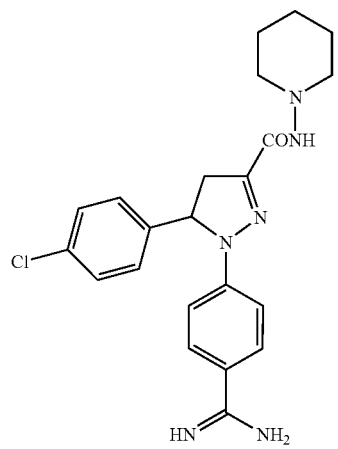

45

Scheme 10 describes how the treatment of a oxobutenoic acid when treated with 5-cyanophenylhydrazine, prepared as described in Scheme 4, with 4-methoxyphenylhydrazine in a solvent such as glacial acetic acid at elevated temperatures for several hours should produce the pyrazoline carboxylic acid (step a). Conversion of the carboxylic acid to the acid chloride using thionyl chloride followed by treatment with N-aminopiperidine should afford the hydazide ester (step b). Heating a mixture of the arylnitrile with sodium azide and zinc chloride or zinc bromide in water with vigorous stirring should produce the aryl-tetrazole after acidification with dilute hydrochloric acid solution (step c). Alternatively, the nitrile can be treated with HCl gas in a solution of chloroform and methanol at about −15 to 0° C. to form the imidate ester that can immediately be converted to the carboxamidine by subsequent treatment with ammonium carbonate in methanol (step d).

Scheme 11

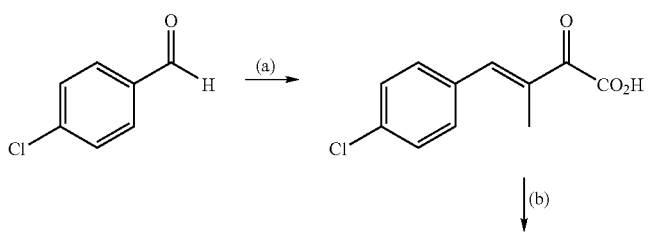

(b)

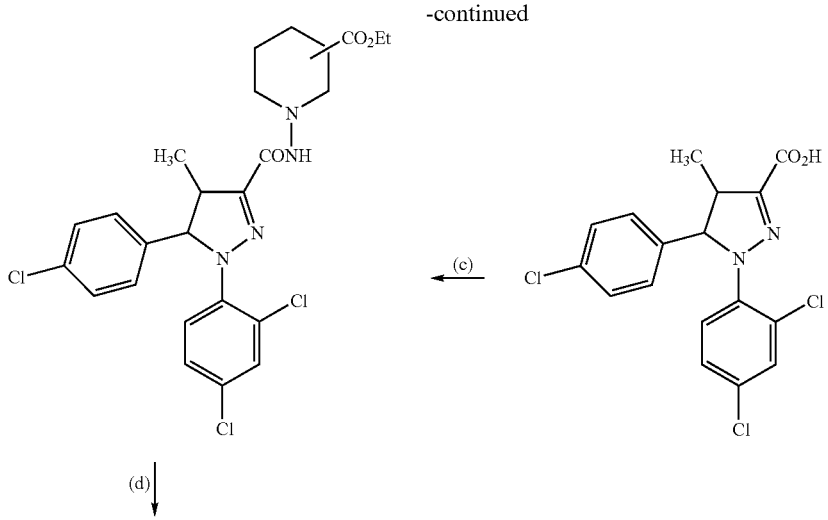

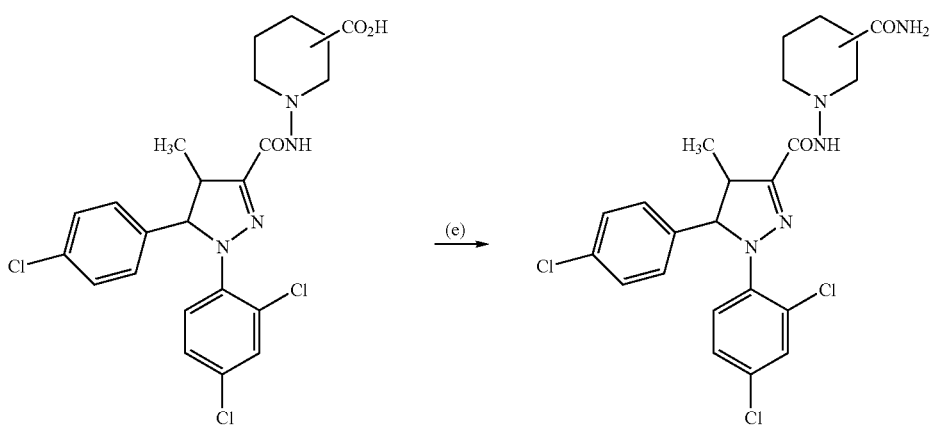

Scheme 11 depicts how the reaction of 4-chlorobenzaldehyde with 2-ketobutyric acid in methanol in the presence of potassium hydroxide at room temperature to about 45° C. should afford, after acidificatioin with HCl solution, the unsaturated acid (step a). Heating this keto-acid with an aryl hydrazine in a solvent such as glacial acetic acid under a nitrogen atmosphere for 2-4 hours should produce the pyrazoline carboxylic acid (step b) as a mixture of diastereomers. The pyrazoline carboxylic acid can be treated with thionyl chloride in toluene in the presence of a few drops of DMF catalyst at elevated temperatures to produce the acid chloride, which upon treatment with ethyl 1-aminonipecotate or ethyl 1-amino-isonipecotate in the presence of diisopropylethylamine at 0° C. to room temperature should afford the hydrazide esters (step c). Hydrolysis of the ester with lithium hydroxide in aqueous THF solution and acidification with dilute hydrochloric acid solution should yield the hydrazide carboxylic acid (step d). The carboxylic acid can then be treated with thionyl chloride followed by ammonia, or with Boc anhydride in THF in the presence of pyridine, followed by a solution of ammonia in THF at 0° C. to ambient temperature to produce the carboxamido hydrazide (step e).

One stereoisomer of a compound of the present invention may be a more potent cannabinoid receptor antagonist than its counterpart(s). Thus, stereoisomers are included in the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

Tables 1a-6b show representative examples of the compounds of the present invention. Each example in the tables represents an individual species of the present invention.

TABLE 1a

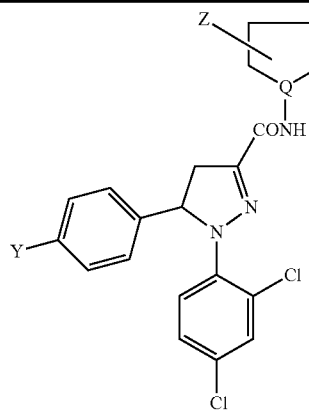

| Ex. # | Y | Z (position on ring) | Q | n |
|---|---|---|---|---|
| 1 | Cl | 2-CO₂Et | N | 1 |
| 2 | Cl | 2-CO₂H | N | 1 |
| 3 | Cl | 2-CH₂CO₂Et | N | 1 |
| 4 | Cl | 2-CH₂CO₂H | N | 1 |
| 5 | CH₃ | 2-CO₂Et | N | 1 |
| 6 | CH₃ | 2-CO₂H | N | 1 |
| 7 | CH₃ | 2-CH₂CO₂Et | N | 1 |
| 8 | CH₃ | 2-CH₂CO₂H | N | 1 |
| 9 | OCH₃ | 2-CO₂Et | N | 1 |
| 10 | OCH₃ | 2-CO₂H | N | 1 |
| 11 | OCH₃ | 2-CH₂CO₂Et | N | 1 |
| 12 | OCH₃ | 2-CH₂CO₂H | N | 1 |
| 13 | CH(CH₃)₂ | 2-CO₂Et | N | 1 |
| 14 | CH(CH₃)₂ | 2-CO₂H | N | 1 |
| 15 | CH(CH₃)₂ | 2-CH₂CO₂Et | N | 1 |
| 16 | CH(CH₃)₂ | 2-CH₂CO₂H | N | 1 |
| 17 | Cl | 2-CO₂Et | N | 2 |
| 18 | Cl | 2-CO₂H | N | 2 |
| 19 | Cl | 2-CH₂CO₂Et | N | 2 |
| 20 | Cl | 2-CH₂CO₂H | N | 2 |
| 21 | CH₃ | 2-CO₂Et | N | 2 |
| 22 | CH₃ | 2-CO₂H | N | 2 |
| 23 | CH₃ | 2-CH₂CO₂Et | N | 2 |
| 24 | CH₃ | 2-CH₂CO₂H | N | 2 |
| 25 | OCH₃ | 2-CO₂Et | N | 2 |
| 26 | OCH₃ | 2-CO₂H | N | 2 |
| 27 | OCH₃ | 2-CH₂CO₂Et | N | 2 |
| 28 | OCH₃ | 2-CH₂CO₂H | N | 2 |
| 29 | CH(CH₃)₂ | 2-CO₂Et | N | 2 |
| 30 | CH(CH₃)₂ | 2-CO₂H | N | 2 |
| 31 | CH(CH₃)₂ | 2-CH₂CO₂Et | N | 2 |
| 32 | CH(CH₃)₂ | 2-CH₂CO₂H | N | 2 |
| 33 | Cl | 3-CO₂Et | N | 1 |
| 34 | Cl | 3-CO₂H | N | 1 |
| 35 | Cl | 3-CH₂CO₂Et | N | 1 |
| 36 | Cl | 3-CH₂CO₂H | N | 1 |
| 37 | CH₃ | 3-CO₂Et | N | 1 |
| 38 | CH₃ | 3-CO₂H | N | 1 |
| 39 | CH₃ | 3-CH₂CO₂Et | N | 1 |
| 40 | CH₃ | 3-CH₂CO₂H | N | 1 |
| 41 | OCH₃ | 3-CO₂Et | N | 1 |
| 42 | OCH₃ | 3-CO₂H | N | 1 |
| 43 | OCH₃ | 3-CH₂CO₂Et | N | 1 |
| 44 | OCH₃ | 3-CH₂CO₂H | N | 1 |
| 45 | CH(CH₃)₂ | 3-CO₂Et | N | 1 |
| 46 | CH(CH₃)₂ | 3-CO₂H | N | 1 |
| 47 | CH(CH₃)₂ | 3-CH₂CO₂Et | N | 1 |
| 48 | CH(CH₃)₂ | 3-CH₂CO₂H | N | 1 |
| 49 | Cl | 3-CO₂Et | N | 2 |
| 50 | Cl | 3-CO₂H | N | 2 |
| 51 | Cl | 3-CH₂CO₂Et | N | 2 |
| 52 | Cl | 3-CH₂CO₂H | N | 2 |
| 53 | CH₃ | 3-CO₂Et | N | 2 |
| 54 | CH₃ | 3-CO₂H | N | 2 |
| 55 | CH₃ | 3-CH₂CO₂Et | N | 2 |
| 56 | CH₃ | 3-CH₂CO₂H | N | 2 |
| 57 | OCH₃ | 3-CO₂Et | N | 2 |

TABLE 1a-continued

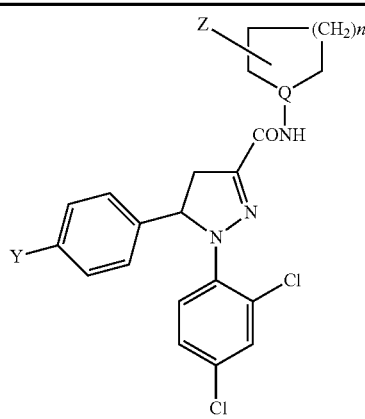

| Ex. # | Y | Z (position on ring) | Q | n |
|---|---|---|---|---|
| 58 | OCH₃ | 3-CO₂H | N | 2 |
| 59 | OCH₃ | 3-CH₂CO₂Et | N | 2 |
| 60 | OCH₃ | 3-CH₂CO₂H | N | 2 |
| 61 | CH(CH₃)₂ | 3-CO₂Et | N | 2 |
| 62 | CH(CH₃)₂ | 3-CO₂H | N | 2 |
| 63 | CH(CH₃)₂ | 3-CH₂CO₂Et | N | 2 |
| 64 | CH(CH₃)₂ | 3-CH₂CO₂H | N | 2 |
| 65 | Cl | 4-CO₂Et | N | 2 |
| 66 | Cl | 4-CO₂H | N | 2 |
| 67 | Cl | 4-CH₂CO₂Et | N | 2 |
| 68 | Cl | 4-CH₂CO₂H | N | 2 |
| 69 | CH₃ | 4-CO₂Et | N | 2 |
| 70 | CH₃ | 4-CO₂H | N | 2 |
| 71 | CH₃ | 4-CH₂CO₂Et | N | 2 |
| 72 | CH₃ | 4-CH₂CO₂H | N | 2 |
| 73 | OCH₃ | 4-CO₂Et | N | 2 |
| 74 | OCH₃ | 4-CO₂H | N | 2 |
| 75 | OCH₃ | 4-CH₂CO₂Et | N | 2 |
| 76 | OCH₃ | 4-CH₂CO₂H | N | 2 |
| 77 | CH(CH₃)₂ | 4-CO₂Et | N | 2 |
| 78 | CH(CH₃)₂ | 4-CO₂H | N | 2 |
| 79 | CH(CH₃)₂ | 4-CH₂CO₂Et | N | 2 |
| 80 | CH(CH₃)₂ | 4-CH₂CO₂H | N | 2 |
| 81 | Cl | 1-CO₂Et | C | 1 |
| 82 | Cl | 1-CO₂H | C | 1 |
| 83 | Cl | 1-CH₂CO₂Et | C | 1 |
| 84 | Cl | 1-CH₂CO₂H | C | 1 |
| 85 | CH₃ | 1-CO₂Et | C | 1 |
| 86 | CH₃ | 1-CO₂H | C | 1 |
| 87 | CH₃ | 1-CH₂CO₂Et | C | 1 |
| 88 | CH₃ | 1-CH₂CO₂H | C | 1 |
| 89 | OCH₃ | 1-CO₂Et | C | 1 |
| 90 | OCH₃ | 1-CO₂H | C | 1 |
| 91 | OCH₃ | 1-CH₂CO₂Et | C | 1 |
| 92 | OCH₃ | 1-CH₂CO₂H | C | 1 |
| 93 | CH(CH₃)₂ | 1-CO₂Et | C | 1 |
| 94 | CH(CH₃)₂ | 1-CO₂H | C | 1 |
| 95 | CH(CH₃)₂ | 1-CH₂CO₂Et | C | 1 |
| 96 | CH(CH₃)₂ | 1-CH₂CO₂H | C | 1 |
| 97 | Cl | 1-CO₂Et | C | 2 |
| 98 | Cl | 1-CO₂H | C | 2 |
| 99 | Cl | 1-CH₂CO₂Et | C | 2 |
| 100 | Cl | 1-CH₂CO₂H | C | 2 |
| 101 | CH₃ | 1-CO₂Et | C | 2 |
| 102 | CH₃ | 1-CO₂H | C | 2 |
| 103 | CH₃ | 1-CH₂CO₂Et | C | 2 |
| 104 | CH₃ | 2-CH₂CO₂H | C | 2 |
| 105 | OCH₃ | 2-CO₂Et | C | 2 |
| 105 | OCH₃ | 1-CO₂H | C | 2 |
| 107 | OCH₃ | 1-CH₂CO₂Et | C | 2 |

TABLE 1a-continued

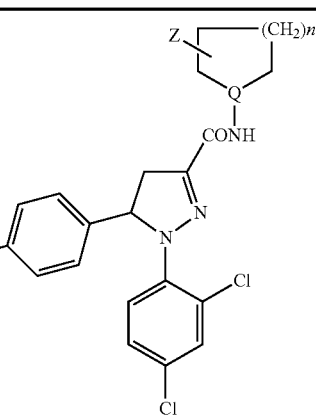

| Ex. # | Y | Z (position on ring) | Q | n |
|---|---|---|---|---|
| 108 | OCH$_3$ | 1-CH$_2$CO$_2$H | C | 2 |
| 109 | CH(CH$_3$)$_2$ | 1-CO$_2$Et | C | 2 |
| 110 | CH(CH$_3$)$_2$ | 1-CO$_2$H | C | 2 |
| 111 | CH(CH$_3$)$_2$ | 1-CH$_2$CO$_2$Et | C | 2 |
| 112 | CH(CH$_3$)$_2$ | 1-CH$_2$CO$_2$H | C | 2 |
| 113 | Cl | 2-CO$_2$Et | CH | 1 |
| 114 | Cl | 2-CO$_2$H | CH | 1 |
| 115 | Cl | 2-CH$_2$CO$_2$Et | CH | 1 |
| 116 | Cl | 2-CH$_2$CO$_2$H | CH | 1 |
| 117 | CH$_3$ | 2-CO$_2$Et | CH | 1 |
| 118 | CH$_3$ | 2-CO$_2$H | CH | 1 |
| 119 | CH$_3$ | 2-CH$_2$CO$_2$Et | CH | 1 |
| 120 | CH$_3$ | 2-CH$_2$CO$_2$H | CH | 1 |
| 121 | OCH$_3$ | 2-CO$_2$Et | CH | 1 |
| 122 | OCH$_3$ | 2-CO$_2$H | CH | 1 |
| 123 | OCH$_3$ | 2-CH$_2$CO$_2$Et | CH | 1 |
| 124 | OCH$_3$ | 2-CH$_2$CO$_2$H | CH | 1 |
| 125 | CH(CH$_3$)$_2$ | 2-CO$_2$Et | CH | 1 |
| 126 | CH(CH$_3$)$_2$ | 2-CO$_2$H | CH | 1 |
| 127 | CH(CH$_3$)$_2$ | 2-CH$_2$CO$_2$Et | CH | 1 |
| 128 | CH(CH$_3$)$_2$ | 2-CH$_2$CO$_2$H | CH | 1 |
| 129 | Cl | 2-CO$_2$Et | CH | 2 |
| 130 | Cl | 2-CO$_2$H | CH | 2 |
| 131 | Cl | 2-CH$_2$CO$_2$Et | CH | 2 |
| 132 | Cl | 2-CH$_2$CO$_2$H | CH | 2 |
| 133 | CH$_3$ | 2-CO$_2$Et | CH | 2 |
| 134 | CH$_3$ | 2-CO$_2$H | CH | 2 |
| 135 | CH$_3$ | 2-CH$_2$CO$_2$Et | CH | 2 |
| 136 | CH$_3$ | 2-CH$_2$CO$_2$H | CH | 2 |
| 137 | OCH$_3$ | 2-CO$_2$Et | CH | 2 |
| 138 | OCH$_3$ | 2-CO$_2$H | CH | 2 |
| 139 | OCH$_3$ | 2-CH$_2$CO$_2$Et | CH | 2 |
| 140 | OCH$_3$ | 2-CH$_2$CO$_2$H | CH | 2 |
| 141 | CH(CH$_3$)$_2$ | 2-CO$_2$Et | CH | 2 |
| 142 | CH(CH$_3$)$_2$ | 2-CO$_2$H | CH | 2 |
| 143 | CH(CH$_3$)$_2$ | 2-CH$_2$CO$_2$Et | CH | 2 |
| 144 | CH(CH$_3$)$_2$ | 2-CH$_2$CO$_2$H | CH | 2 |

TABLE 1b

| Ex. # | Y | Z (position on ring) | Q | n |
|---|---|---|---|---|
| 1 | Cl | 2-CH$_2$OCH$_2$CO$_2$Et | N | 1 |
| 2 | Cl | 2-CH$_2$OCH$_2$CO$_2$H | N | 1 |
| 3 | Cl | 2-CH$_2$O(CH$_2$)$_3$PO(OEt)$_2$ | N | 1 |
| 4 | Cl | 2-CH$_2$O(CH$_2$)$_3$PO(OH)$_2$ | N | 1 |
| 5 | CH$_3$ | 2-CH$_2$OCH$_2$CO$_2$Et | N | 1 |
| 6 | CH$_3$ | 2-CH$_2$OCH$_2$CO$_2$H | N | 1 |
| 7 | CH$_3$ | 2-CH$_2$O(CH$_2$)$_3$PO(OEt)$_2$ | N | 1 |
| 8 | CH$_3$ | 2-CH$_2$O(CH$_2$)$_3$PO(OH)$_2$ | N | 1 |
| 9 | OCH$_3$ | 2-CH$_2$OCH$_2$CO$_2$Et | N | 1 |
| 10 | OCH$_3$ | 2-CH$_2$OCH$_2$CO$_2$H | N | 1 |
| 11 | OCH$_3$ | 2-CH$_2$O(CH$_2$)$_3$PO(OEt)$_2$ | N | 1 |
| 12 | OCH$_3$ | 2-CH$_2$O(CH$_2$)$_3$PO(OH)$_2$ | N | 1 |
| 13 | CH(CH$_3$)$_2$ | 2-CH$_2$OCH$_2$CO$_2$Et | N | 1 |
| 14 | CH(CH$_3$)$_2$ | 2-CH$_2$OCH$_2$CO$_2$H | N | 1 |
| 15 | CH(CH$_3$)$_2$ | 2-CH$_2$O(CH$_2$)$_3$PO(OEt)$_2$ | N | 1 |
| 16 | CH(CH$_3$)$_2$ | 2-CH$_2$O(CH$_2$)$_3$PO(OH)$_2$ | N | 1 |
| 17 | Cl | 2-CH$_2$OCH$_2$CO$_2$Et | N | 2 |
| 18 | Cl | 2-CH$_2$OCH$_2$CO$_2$H | N | 2 |
| 19 | Cl | 2-CH$_2$O(CH$_2$)$_3$PO(OEt)$_2$ | N | 2 |
| 20 | Cl | 2-CH$_2$O(CH$_2$)$_3$PO(OH)$_2$ | N | 2 |
| 21 | CH$_3$ | 2-CH$_2$OCH$_2$CO$_2$Et | N | 2 |
| 22 | CH$_3$ | 2-CH$_2$OCH$_2$CO$_2$H | N | 2 |
| 23 | CH$_3$ | 2-CH$_2$O(CH$_2$)$_3$PO(OEt)$_2$ | N | 2 |
| 24 | CH$_3$ | 2-CH$_2$O(CH$_2$)$_3$PO(OH)$_2$ | N | 2 |
| 25 | OCH$_3$ | 2-CH$_2$OCH$_2$CO$_2$Et | N | 2 |
| 26 | OCH$_3$ | 2-CH$_2$OCH$_2$CO$_2$H | N | 2 |
| 27 | OCH$_3$ | 2-CH$_2$O(CH$_2$)$_3$PO(OEt)$_2$ | N | 2 |
| 28 | OCH$_3$ | 2-CH$_2$O(CH$_2$)$_3$PO(OH)$_2$ | N | 2 |
| 29 | CH(CH$_3$)$_2$ | 2-CH$_2$OCH$_2$CO$_2$Et | N | 2 |
| 30 | CH(CH$_3$)$_2$ | 2-CH$_2$OCH$_2$CO$_2$H | N | 2 |
| 31 | CH(CH$_3$)$_2$ | 2-CH$_2$O(CH$_2$)$_3$PO(OEt)$_2$ | N | 2 |
| 32 | CH(CH$_3$)$_2$ | 2-CH$_2$O(CH$_2$)$_3$PO(OH)$_2$ | N | 2 |
| 33 | Cl | 3-CH$_2$OCH$_2$CO$_2$Et | N | 1 |
| 34 | Cl | 3-CH$_2$OCH$_2$CO$_2$H | N | 1 |
| 35 | Cl | 3-CH$_2$O(CH$_2$)$_3$PO(OEt)$_2$ | N | 1 |
| 36 | Cl | 3-CH$_2$O(CH$_2$)$_3$PO(OH)$_2$ | N | 1 |
| 37 | CH$_3$ | 3-CH$_2$OCH$_2$CO$_2$Et | N | 1 |
| 38 | CH$_3$ | 3-CH$_2$OCH$_2$CO$_2$H | N | 1 |
| 39 | CH$_3$ | 3-CH$_2$O(CH$_2$)$_3$PO(OEt)$_2$ | N | 1 |
| 40 | CH$_3$ | 3-CH$_2$O(CH$_2$)$_3$PO(OH)$_2$ | N | 1 |
| 41 | OCH$_3$ | 3-CH$_2$OCH$_2$CO$_2$Et | N | 1 |
| 42 | OCH$_3$ | 3-CH$_2$OCH$_2$CO$_2$H | N | 1 |
| 43 | OCH$_3$ | 3-CH$_2$O(CH$_2$)$_3$PO(OEt)$_2$ | N | 1 |
| 44 | OCH$_3$ | 3-CH$_2$O(CH$_2$)$_3$PO(OH)$_2$ | N | 1 |
| 45 | CH(CH$_3$)$_2$ | 3-CH$_2$OCH$_2$CO$_2$Et | N | 1 |
| 46 | CH(CH$_3$)$_2$ | 3-CH$_2$OCH$_2$CO$_2$H | N | 1 |
| 47 | CH(CH$_3$)$_2$ | 3-CH$_2$O(CH$_2$)$_3$PO(OEt)$_2$ | N | 1 |
| 48 | CH(CH$_3$)$_2$ | 3-CH$_2$O(CH$_2$)$_3$PO(OH)$_2$ | N | 1 |
| 49 | Cl | 3-CH$_2$OCH$_2$CO$_2$Et | N | 2 |
| 50 | Cl | 3-CH$_2$OCH$_2$CO$_2$H | N | 2 |
| 51 | Cl | 3-CH$_2$O(CH$_2$)$_3$PO(OEt)$_2$ | N | 2 |
| 52 | Cl | 3-CH$_2$O(CH$_2$)$_3$PO(OH)$_2$ | N | 2 |
| 53 | CH$_3$ | 3-CH$_2$OCH$_2$CO$_2$Et | N | 2 |
| 54 | CH$_3$ | 3-CH$_2$OCH$_2$CO$_2$H | N | 2 |
| 55 | CH$_3$ | 3-CH$_2$O(CH$_2$)$_3$PO(OEt)$_2$ | N | 2 |
| 56 | CH$_3$ | 3-CH$_2$O(CH$_2$)$_3$PO(OH)$_2$ | N | 2 |
| 57 | OCH$_3$ | 3-CH$_2$OCH$_2$CO$_2$Et | N | 2 |

TABLE 1b-continued

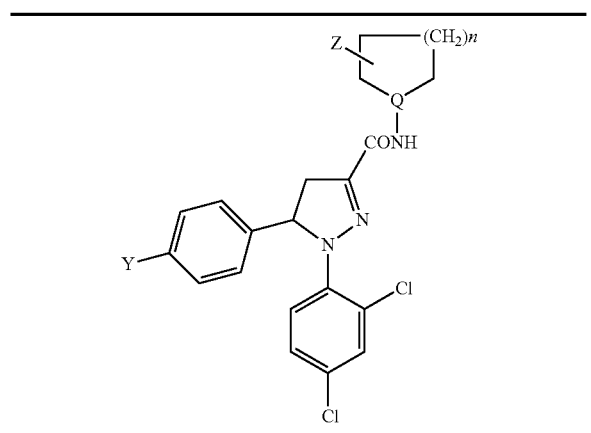

| Ex. # | Y | Z (position on ring) | Q | n |
|---|---|---|---|---|
| 58 | OCH₃ | 3-CH₂OCH₂CO₂H | N | 2 |
| 59 | OCH₃ | 3-CH₂O(CH₂)₃PO(OEt)₂ | N | 2 |
| 60 | OCH₃ | 3-CH₂O(CH₂)₃PO(OH)₂ | N | 2 |
| 61 | CH(CH₃)₂ | 3-CH₂OCH₂CO₂Et | N | 2 |
| 62 | CH(CH₃)₂ | 3-CH₂OCH₂CO₂H | N | 2 |
| 63 | CH(CH₃)₂ | 3-CH₂O(CH₂)₃PO(OEt)₂ | N | 2 |
| 64 | CH(CH₃)₂ | 3-CH₂O(CH₂)₃PO(OH)₂ | N | 2 |
| 65 | Cl | 4-CH₂OCH₂CO₂Et | N | 2 |
| 66 | Cl | 4-CH₂OCH₂CO₂H | N | 2 |
| 67 | Cl | 4-CH₂O(CH₂)₃PO(OEt)₂ | N | 2 |
| 68 | Cl | 4-CH₂O(CH₂)₃PO(OH)₂ | N | 2 |
| 69 | CH₃ | 4-CH₂OCH₂CO₂Et | N | 2 |
| 70 | CH₃ | 4-CH₂OCH₂CO₂H | N | 2 |
| 71 | CH₃ | 4-CH₂O(CH₂)₃PO(OEt)₂ | N | 2 |
| 72 | CH₃ | 4-CH₂O(CH₂)₃PO(OH)₂ | N | 2 |
| 73 | OCH₃ | 4-CH₂OCH₂CO₂Et | N | 2 |
| 74 | OCH₃ | 4-CH₂OCH₂CO₂H | N | 2 |
| 75 | OCH₃ | 4-CH₂O(CH₂)₃PO(OEt)₂ | N | 2 |
| 76 | OCH₃ | 4-CH₂O(CH₂)₃PO(OH)₂ | N | 2 |
| 77 | CH(CH₃)₂ | 4-CH₂OCH₂CO₂Et | N | 2 |
| 78 | CH(CH₃)₂ | 4-CH₂OCH₂CO₂H | N | 2 |
| 79 | CH(CH₃)₂ | 4-CH₂O(CH₂)₃PO(OEt)₂ | N | 2 |
| 80 | CH(CH₃)₂ | 4-CH₂O(CH₂)₃PO(OH)₂ | N | 2 |
| 81 | Cl | 2-CH₂OCH₂CO₂Et | CH | 1 |
| 82 | Cl | 2-CH₂OCH₂CO₂H | CH | 1 |
| 83 | Cl | 2-CH₂O(CH₂)₃PO(OEt)₂ | CH | 1 |
| 84 | Cl | 2-CH₂O(CH₂)₃PO(OH)₂ | CH | 1 |
| 85 | CH₃ | 2-CH₂OCH₂CO₂Et | CH | 1 |
| 86 | CH₃ | 2-CH₂OCH₂CO₂H | CH | 1 |
| 87 | CH₃ | 2-CH₂O(CH₂)₃PO(OEt)₂ | CH | 1 |
| 88 | CH₃ | 2-CH₂O(CH₂)₃PO(OH)₂ | CH | 1 |
| 89 | OCH₃ | 2-CH₂OCH₂CO₂Et | CH | 1 |
| 90 | OCH₃ | 2-CH₂OCH₂CO₂H | CH | 1 |
| 91 | OCH₃ | 2-CH₂O(CH₂)₃PO(OEt)₂ | CH | 1 |
| 92 | OCH₃ | 2-CH₂O(CH₂)₃PO(OH)₂ | CH | 1 |
| 93 | CH(CH₃)₂ | 2-CH₂OCH₂CO₂Et | CH | 1 |
| 94 | CH(CH₃)₂ | 2-CH₂OCH₂CO₂H | CH | 1 |
| 95 | CH(CH₃)₂ | 2-CH₂O(CH₂)₃PO(OEt)₂ | CH | 1 |
| 96 | CH(CH₃)₂ | 2-CH₂O(CH₂)₃PO(OH)₂ | CH | 1 |
| 97 | Cl | 2-CH₂OCH₂CO₂Et | CH | 2 |
| 98 | Cl | 2-CH₂OCH₂CO₂H | CH | 2 |
| 99 | Cl | 2-CH₂O(CH₂)₃PO(OEt)₂ | CH | 2 |
| 100 | Cl | 2-CH₂O(CH₂)₃PO(OH)₂ | CH | 2 |
| 101 | CH₃ | 2-CH₂OCH₂CO₂Et | CH | 2 |
| 102 | CH₃ | 2-CH₂OCH₂CO₂H | CH | 2 |
| 103 | CH₃ | 2-CH₂O(CH₂)₃PO(OEt)₂ | CH | 2 |
| 104 | CH₃ | 2-CH₂O(CH₂)₃PO(OH)₂ | CH | 2 |
| 105 | OCH₃ | 2-CH₂OCH₂CO₂Et | CH | 2 |
| 105 | OCH₃ | 2-CH₂OCH₂CO₂H | CH | 2 |
| 107 | OCH₃ | 2-CH₂O(CH₂)₃PO(OEt)₂ | CH | 2 |

TABLE 1b-continued

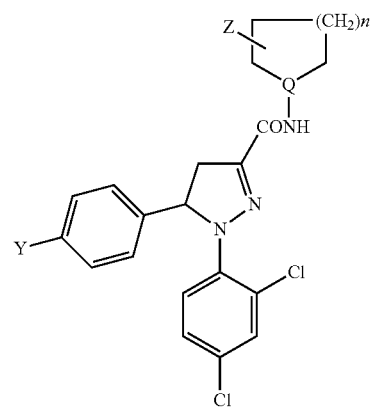

| Ex. # | Y | Z (position on ring) | Q | n |
|---|---|---|---|---|
| 108 | OCH₃ | 2-CH₂O(CH₂)₃PO(OH)₂ | CH | 2 |
| 109 | CH(CH₃)₂ | 2-CH₂OCH₂CO₂Et | CH | 2 |
| 110 | CH(CH₃)₂ | 2-CH₂OCH₂CO₂H | CH | 2 |
| 111 | CH(CH₃)₂ | 2-CH₂O(CH₂)₃PO(OEt)₂ | CH | 2 |
| 112 | CH(CH₃)₂ | 2-CH₂O(CH₂)₃PO(OH)₂ | CH | 2 |
| 113 | Cl | 1-CH₂OCH₂CO₂Et | C | 1 |
| 114 | Cl | 1-CH₂OCH₂CO₂H | C | 1 |
| 115 | Cl | 1-CH₂O(CH₂)₃PO(OEt)₂ | C | 1 |
| 116 | Cl | 1-CH₂O(CH₂)₃PO(OH)₂ | C | 1 |
| 117 | CH₃ | 1-CH₂OCH₂CO₂Et | C | 1 |
| 118 | CH₃ | 1-CH₂OCH₂CO₂H | C | 1 |
| 119 | CH₃ | 1-CH₂O(CH₂)₃PO(OEt)₂ | C | 1 |
| 120 | CH₃ | 1-CH₂O(CH₂)₃PO(OH)₂ | C | 1 |
| 121 | OCH₃ | 1-CH₂OCH₂CO₂Et | C | 1 |
| 122 | OCH₃ | 1-CH₂OCH₂CO₂H | C | 1 |
| 123 | OCH₃ | 1-CH₂O(CH₂)₃PO(OEt)₂ | C | 1 |
| 124 | OCH₃ | 1-CH₂O(CH₂)₃PO(OH)₂ | C | 1 |
| 125 | CH(CH₃)₂ | 1-CH₂OCH₂CO₂Et | C | 1 |
| 126 | CH(CH₃)₂ | 1-CH₂OCH₂CO₂H | C | 1 |
| 127 | CH(CH₃)₂ | 1-CH₂O(CH₂)₃PO(OEt)₂ | C | 1 |
| 128 | CH(CH₃)₂ | 1-CH₂O(CH₂)₃PO(OH)₂ | C | 1 |
| 129 | Cl | 3-CH₂OCH₂CO₂Et | CH | 2 |
| 130 | Cl | 3-CH₂OCH₂CO₂H | CH | 2 |
| 131 | Cl | 3-CH₂O(CH₂)₃PO(OEt)₂ | CH | 2 |
| 132 | Cl | 3-CH₂O(CH₂)₃PO(OH)₂ | CH | 2 |
| 133 | CH₃ | 3-CH₂OCH₂CO₂Et | CH | 2 |
| 134 | CH₃ | 3-CH₂OCH₂CO₂H | CH | 2 |
| 135 | CH₃ | 3-CH₂O(CH₂)₃PO(OEt)₂ | CH | 2 |
| 136 | CH₃ | 3-CH₂O(CH₂)₃PO(OH)₂ | CH | 2 |
| 137 | OCH₃ | 3-CH₂OCH₂CO₂Et | CH | 2 |
| 138 | OCH₃ | 3-CH₂OCH₂CO₂H | CH | 2 |
| 139 | OCH₃ | 3-CH₂O(CH₂)₃PO(OEt)₂ | CH | 2 |
| 140 | OCH₃ | 3-CH₂O(CH₂)₃PO(OH)₂ | CH | 2 |
| 141 | CH(CH₃)₂ | 3-CH₂OCH₂CO₂Et | CH | 2 |
| 142 | CH(CH₃)₂ | 3-CH₂OCH₂CO₂H | CH | 2 |
| 143 | CH(CH₃)₂ | 3-CH₂O(CH₂)₃PO(OEt)₂ | CH | 2 |
| 144 | CH(CH₃)₂ | 2-CH₂O(CH₂)₃PO(OH)₂ | CH | 2 |

TABLE 1c

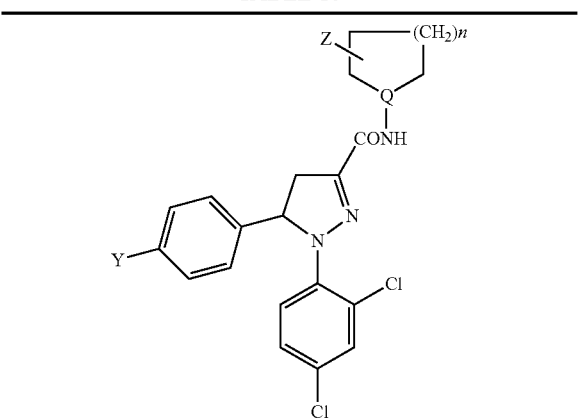

| Ex. # | Y | Z (position on ring) | Q | n |
|---|---|---|---|---|
| 1 | Cl | 2-CONH$_2$ | N | 1 |
| 2 | Cl | 2-CH$_2$OCH$_2$CONH$_2$ | N | 1 |
| 3 | Cl | 2-CH$_2$CONH$_2$ | N | 1 |
| 4 | Cl | 2-CH$_2$OCH$_2$CH=CHCONH$_2$ | N | 1 |
| 5 | CH$_3$ | 2-CONH$_2$ | N | 1 |
| 6 | CH$_3$ | 2-CH$_2$OCH$_2$CONH$_2$ | N | 1 |
| 7 | CH$_3$ | 2-CH$_2$CONH$_2$ | N | 1 |
| 8 | CH$_3$ | 2-CH$_2$OCH$_2$CH=CHCONH$_2$ | N | 1 |
| 9 | OCH$_3$ | 2-CONH$_2$ | N | 1 |
| 10 | OCH$_3$ | 2-CH$_2$OCH$_2$CONH$_2$ | N | 1 |
| 11 | OCH$_3$ | 2-CH$_2$CONH$_2$ | N | 1 |
| 12 | OCH$_3$ | 2-CH$_2$OCH$_2$CH=CHCONH$_2$ | N | 1 |
| 13 | CH(CH$_3$)$_2$ | 2-CONH$_2$ | N | 1 |
| 14 | CH(CH$_3$)$_2$ | 2-CH$_2$OCH$_2$CONH$_2$ | N | 1 |
| 15 | CH(CH$_3$)$_2$ | 2-CH$_2$CONH$_2$ | N | 1 |
| 16 | CH(CH$_3$)$_2$ | 2-CH$_2$OCH$_2$CH=CHCONH$_2$ | N | 1 |
| 17 | Cl | 2-CONH$_2$ | N | 2 |
| 18 | Cl | 2-CH$_2$OCH$_2$CONH$_2$ | N | 2 |
| 19 | Cl | 2-CH$_2$CONH$_2$ | N | 2 |
| 20 | Cl | 2-CH$_2$OCH$_2$CH=CHCONH$_2$ | N | 2 |
| 21 | CH$_3$ | 2-CONH$_2$ | N | 2 |
| 22 | CH$_3$ | 2-CH$_2$OCH$_2$CONH$_2$ | N | 2 |
| 23 | CH$_3$ | 2-CH$_2$CONH$_2$ | N | 2 |
| 24 | CH$_3$ | 2-CH$_2$OCH$_2$CH=CHCONH$_2$ | N | 2 |
| 25 | OCH$_3$ | 2-CONH$_2$ | N | 2 |
| 26 | OCH$_3$ | 2-CH$_2$OCH$_2$CONH$_2$ | N | 2 |
| 27 | OCH$_3$ | 2-CH$_2$CONH$_2$ | N | 2 |
| 28 | OCH$_3$ | 2-CH$_2$OCH$_2$CH=CHCONH$_2$ | N | 2 |
| 29 | CH(CH$_3$)$_2$ | 2-CONH$_2$ | N | 2 |
| 30 | CH(CH$_3$)$_2$ | 2-CH$_2$OCH$_2$CONH$_2$ | N | 2 |
| 31 | CH(CH$_3$)$_2$ | 2-CH$_2$CONH$_2$ | N | 2 |
| 32 | CH(CH$_3$)$_2$ | 2-CH$_2$OCH$_2$CH=CHCONH$_2$ | N | 2 |
| 33 | Cl | 3-CONH$_2$ | N | 1 |
| 34 | Cl | 3-CH$_2$OCH$_2$CONH$_2$ | N | 1 |
| 35 | Cl | 3-CH$_2$CONH$_2$ | N | 1 |
| 36 | Cl | 3-CH$_2$OCH$_2$CH=CHCONH$_2$ | N | 1 |
| 37 | CH$_3$ | 3-CONH$_2$ | N | 1 |
| 38 | CH$_3$ | 3-CH$_2$OCH$_2$CONH$_2$ | N | 1 |
| 39 | CH$_3$ | 3-CH$_2$CONH$_2$ | N | 1 |
| 40 | CH$_3$ | 3-CH$_2$OCH$_2$CH=CHCONH$_2$ | N | 1 |
| 41 | OCH$_3$ | 3-CONH$_2$ | N | 1 |
| 42 | OCH$_3$ | 3-CH$_2$OCH$_2$CONH$_2$ | N | 1 |
| 43 | OCH$_3$ | 3-CH$_2$CONH$_2$ | N | 1 |
| 44 | OCH$_3$ | 3-CH$_2$OCH$_2$CH=CHCONH$_2$ | N | 1 |
| 45 | CH(CH$_3$)$_2$ | 3-CONH$_2$ | N | 1 |
| 4 | CH(CH$_3$)$_2$ | 3-CH$_2$OCH$_2$CONH$_2$ | N | 1 |
| 47 | CH(CH$_3$)$_2$ | 3-CH$_2$CONH$_2$ | N | 1 |
| 48 | CH(CH$_3$)$_2$ | 3-CH$_2$OCH$_2$CH=CHCONH$_2$ | N | 1 |
| 49 | Cl | 3-CONH$_2$ | N | 2 |
| 50 | Cl | 3-CH$_2$OCH$_2$CONH$_2$ | N | 2 |
| 51 | Cl | 3-CH$_2$CONH$_2$ | N | 2 |
| 52 | Cl | 3-CH$_2$OCH$_2$CH=CHCONH$_2$ | N | 2 |
| 53 | CH$_3$ | 3-CONH$_2$ | N | 2 |
| 54 | CH$_3$ | 3-CH$_2$OCH$_2$CONH$_2$ | N | 2 |
| 55 | CH$_3$ | 3-CH$_2$CONH$_2$ | N | 2 |
| 56 | CH$_3$ | 3-CH$_2$OCH$_2$CH=CHCONH$_2$ | N | 2 |
| 57 | OCH$_3$ | 3-CONH$_2$ | N | 2 |
| 58 | OCH$_3$ | 3-CH$_2$OCH$_2$CONH$_2$ | N | 2 |
| 59 | OCH$_3$ | 3-CH$_2$CONH$_2$ | N | 2 |
| 60 | OCH$_3$ | 3-CH$_2$OCH$_2$CH=CHCONH$_2$ | N | 2 |
| 61 | CH(CH$_3$)$_2$ | 3-CONH$_2$ | N | 2 |
| 62 | CH(CH$_3$)$_2$ | 3-CH$_2$OCH$_2$CONH$_2$ | N | 2 |
| 63 | CH(CH$_3$)$_2$ | 3-CH$_2$CONH$_2$ | N | 2 |
| 64 | CH(CH$_3$)$_2$ | 3-CH$_2$OCH$_2$CH=CHCONH$_2$ | N | 2 |
| 65 | Cl | 4-CONH$_2$ | N | 2 |
| 66 | Cl | 4-CH$_2$OCH$_2$CONH$_2$ | N | 2 |
| 67 | Cl | 4-CH$_2$CONH$_2$ | N | 2 |
| 68 | Cl | 4-CH$_2$OCH$_2$CH=CHCONH$_2$ | N | 2 |
| 69 | CH$_3$ | 4-CONH$_2$ | N | 2 |
| 70 | CH$_3$ | 4-CH$_2$OCH$_2$CONH$_2$ | N | 2 |
| 71 | CH$_3$ | 4-CH$_2$CONH$_2$ | N | 2 |
| 72 | CH$_3$ | 4-CH$_2$OCH$_2$CH=CHCONH$_2$ | N | 2 |
| 73 | OCH$_3$ | 4-CONH$_2$ | N | 2 |
| 74 | OCH$_3$ | 4-CH$_2$OCH$_2$CONH$_2$ | N | 2 |
| 75 | OCH$_3$ | 4-CH$_2$CONH$_2$ | N | 2 |
| 76 | OCH$_3$ | 4-CH$_2$OCH$_2$CH=CHCONH$_2$ | N | 2 |
| 77 | CH(CH$_3$)$_2$ | 4-CONH$_2$ | N | 2 |
| 78 | CH(CH$_3$)$_2$ | 4-CH$_2$OCH$_2$CONH$_2$ | N | 2 |
| 79 | CH(CH$_3$)$_2$ | 4-CH$_2$CONH$_2$ | N | 2 |
| 80 | CH(CH$_3$)$_2$ | 4-CH$_2$OCH$_2$CH=CHCONH$_2$ | N | 2 |
| 81 | Cl | 1-CONH$_2$ | C | 1 |
| 82 | Cl | 1-CH$_2$OCH$_2$CONH$_2$ | C | 1 |
| 83 | Cl | 1-CH$_2$CONH$_2$ | C | 1 |
| 84 | CH$_3$ | 1-CONH$_2$ | C | 1 |
| 85 | CH$_3$ | 1-CH$_2$OCH$_2$CONH$_2$ | C | 1 |
| 86 | CH$_3$ | 1-CH$_2$CONH$_2$ | C | 1 |
| 87 | OCH$_3$ | 1-CONH$_2$ | C | 1 |
| 88 | OCH$_3$ | 1-CH$_2$OCH$_2$CONH$_2$ | C | 1 |
| 89 | OCH$_3$ | 1-CH$_2$CONH$_2$ | C | 1 |
| 90 | CH(CH$_3$)$_2$ | 1-CONH$_2$ | C | 1 |
| 91 | CH(CH$_3$)$_2$ | 1-CH$_2$OCH$_2$CONH$_2$ | C | 1 |
| 92 | CH(CH$_3$)$_2$ | 1-CH$_2$CONH$_2$ | C | 1 |
| 93 | Cl | 1-CONH$_2$ | C | 2 |
| 94 | Cl | 1-CH$_2$OCH$_2$CONH$_2$ | C | 2 |
| 95 | Cl | 1-CH$_2$CONH$_2$ | C | 2 |
| 96 | CH$_3$ | 1-CONH$_2$ | C | 2 |
| 97 | CH$_3$ | 1-CH$_2$OCH$_2$CONH$_2$ | C | 2 |
| 98 | CH$_3$ | 1-CH$_2$CONH$_2$ | C | 2 |
| 99 | OCH$_3$ | 1-CONH$_2$ | C | 2 |
| 100 | OCH$_3$ | 1-CH$_2$OCH$_2$CONH$_2$ | C | 2 |
| 101 | OCH$_3$ | 1-CH$_2$CONH$_2$ | C | 2 |
| 102 | CH(CH$_3$)$_2$ | 1-CONH$_2$ | C | 2 |
| 103 | CH(CH$_3$)$_2$ | 1-CH$_2$OCH$_2$CONH$_2$ | C | 2 |
| 104 | CH(CH$_3$)$_2$ | 1-CH$_2$CONH$_2$ | C | 2 |
| 105 | Cl | 2-CONH$_2$ | CH | 1 |
| 105 | Cl | 2-CH$_2$OCH$_2$CONH$_2$ | CH | 1 |
| 107 | Cl | 2-CH$_2$CONH$_2$ | CH | 1 |
| 108 | Cl | 2-CH$_2$OCH$_2$CH=CHCONH$_2$ | CH | 1 |
| 109 | CH$_3$ | 2-CONH$_2$ | CH | 1 |
| 110 | CH$_3$ | 2-CH$_2$OCH$_2$CONH$_2$ | CH | 1 |
| 111 | CH$_3$ | 2-CH$_2$CONH$_2$ | CH | 1 |
| 112 | CH$_3$ | 2-CH$_2$OCH$_2$CH=CHCONH$_2$ | CH | 1 |
| 113 | OCH$_3$ | 2-CONH$_2$ | CH | 1 |
| 114 | OCH$_3$ | 2-CH$_2$OCH$_2$CONH$_2$ | CH | 1 |

TABLE 1c-continued

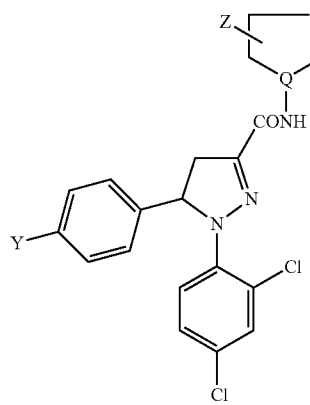

| Ex. # | Y | Z (position on ring) | Q | n |
|---|---|---|---|---|
| 115 | $OCH_3$ | 2-$CH_2CONH_2$ | CH | 1 |
| 116 | $OCH_3$ | 2-$CH_2OCH_2CH=CHCONH_2$ | CH | 1 |
| 117 | $CH(CH_3)_2$ | 2-$CONH_2$ | CH | 1 |
| 118 | $CH(CH_3)_2$ | 2-$CH_2OCH_2CONH_2$ | CH | 1 |
| 119 | $CH(CH_3)_2$ | 2-$CH_2CONH_2$ | CH | 1 |
| 120 | $CH(CH_3)_2$ | 2-$CH_2OCH_2CH=CHCONH_2$ | CH | 1 |
| 121 | Cl | 2-$CONH_2$ | CH | 2 |
| 122 | Cl | 2-$CH_2OCH_2CONH_2$ | CH | 2 |
| 123 | Cl | 2-$CH_2CONH_2$ | CH | 2 |
| 124 | Cl | 2-$CH_2OCH_2CH=CHCONH_2$ | CH | 2 |
| 125 | $CH_3$ | 2-$CONH_2$ | CH | 2 |
| 126 | $CH_3$ | 2-$CH_2OCH_2CONH_2$ | CH | 2 |
| 127 | $CH_3$ | 2-$CH_2CONH_2$ | CH | 2 |
| 128 | $CH_3$ | 2-$CH_2OCH_2CH=CHCONH_2$ | CH | 2 |
| 129 | $OCH_3$ | 2-$CONH_2$ | CH | 2 |
| 130 | $OCH_3$ | 2-$CH_2OCH_2CONH_2$ | CH | 2 |
| 131 | $OCH_3$ | 2-$CH_2CONH_2$ | CH | 2 |
| 132 | $OCH_3$ | 2-$CH_2OCH_2CH=CHCONH_2$ | CH | 2 |
| 133 | $CH(CH_3)_2$ | 2-$CONH_2$ | CH | 2 |
| 134 | $CH(CH_3)_2$ | 2-$CH_2OCH_2CONH_2$ | CH | 2 |
| 135 | $CH(CH_3)_2$ | 2-$CH_2CONH_2$ | CH | 2 |
| 136 | $CH(CH_3)_2$ | 2-$CH_2OCH_2CH=CHCONH_2$ | CH | 2 |
| 137 | Cl | 3-$CONH_2$ | CH | 1 |
| 138 | Cl | 3-$CH_2OCH_2CONH_2$ | CH | 1 |
| 139 | Cl | 3-$CH_2CONH_2$ | CH | 1 |
| 140 | Cl | 3-$CH_2OCH_2CH=CHCONH_2$ | CH | 1 |
| 141 | $CH_3$ | 3-$CONH_2$ | CH | 1 |
| 142 | $CH_3$ | 3-$CH_2OCH_2CONH_2$ | CH | 1 |
| 143 | $CH_3$ | 3-$CH_2CONH_2$ | CH | 1 |
| 144 | $CH_3$ | 3-$CH_2OCH_2CH=CHCONH_2$ | CH | 1 |
| 145 | $OCH_3$ | 3-$CONH_2$ | CH | 1 |
| 146 | $OCH_3$ | 3-$CH_2OCH_2CONH_2$ | CH | 1 |
| 147 | $OCH_3$ | 3-$CH_2CONH_2$ | CH | 1 |
| 148 | $OCH_3$ | 3-$CH_2OCH_2CH=CHCONH_2$ | CH | 1 |
| 149 | $CH(CH_3)_2$ | 3-$CONH_2$ | CH | 1 |
| 150 | $CH(CH_3)_2$ | 3-$CH_2OCH_2CONH_2$ | CH | 1 |
| 151 | $CH(CH_3)_2$ | 3-$CH_2CONH_2$ | CH | 1 |
| 153 | $CH(CH_3)_2$ | 3-$CH_2OCH_2CH=CHCONH_2$ | CH | 1 |
| 154 | Cl | 4-$CONH_2$ | CH | 2 |
| 155 | Cl | 4-$CH_2OCH_2CONH_2$ | CH | 2 |
| 156 | Cl | 4-$CH_2CONH_2$ | CH | 2 |
| 157 | Cl | 4-$CH_2OCH_2CH=CHCONH_2$ | CH | 2 |
| 158 | $CH_3$ | 4-$CONH_2$ | CH | 2 |
| 159 | $CH_3$ | 4-$CH_2OCH_2CONH_2$ | CH | 2 |
| 160 | $CH_3$ | 4-$CH_2CONH_2$ | CH | 2 |
| 161 | $CH_3$ | 4-$CH_2OCH_2CH=CHCONH_2$ | CH | 2 |
| 162 | $OCH_3$ | 4-$CONH_2$ | CH | 2 |
| 163 | $OCH_3$ | 4-$CH_2OCH_2CONH_2$ | CH | 2 |
| 164 | $OCH_3$ | 4-$CH_2CONH_2$ | CH | 2 |
| 165 | $OCH_3$ | 4-$CH_2OCH_2CH=CHCONH_2$ | CH | 2 |
| 166 | $CH(CH_3)_2$ | 4-$CONH_2$ | CH | 2 |
| 176 | $CH(CH_3)_2$ | 4-$CH_2OCH_2CONH_2$ | CH | 2 |
| 168 | $CH(CH_3)_2$ | 4-$CH_2CONH_2$ | CH | 2 |
| 169 | $CH(CH_3)_2$ | 4-$CH_2OCH_2CH=CHCONH_2$ | CH | 2 |
| 170 | Cl | 4-C(NH)$NH_2$ | N | 2 |
| 171 | Cl | 3-C(NH)$NH_2$ | N | 2 |
| 172 | Cl | 2-C(NH)$NH_2$ | N | 1 |

TABLE 1c-continued

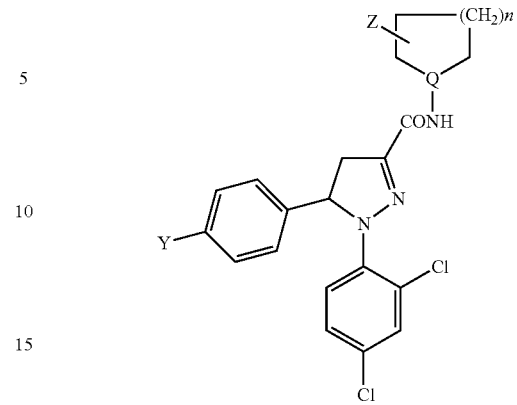

| Ex. # | Y | Z (position on ring) | Q | n |
|---|---|---|---|---|
| 173 | Cl | 3-C(NH)$NH_2$ | N | 1 |
| 174 | $OCH_3$ | 4-C(NH)$NH_2$ | N | 2 |
| 175 | $OCH_3$ | 3-C(NH)$NH_2$ | N | 2 |
| 176 | $OCH_3$ | 2-C(NH)$NH_2$ | N | 1 |
| 177 | $OCH_3$ | 3-C(NH)$NH_2$ | N | 1 |
| 178 | $CH_3$ | 4-C(NH)$NH_2$ | N | 2 |
| 179 | $CH_3$ | 3-C(NH)$NH_2$ | N | 2 |
| 180 | $CH_3$ | 2-C(NH)$NH_2$ | N | 1 |
| 181 | $CH_3$ | 3-C(NH)$NH_2$ | N | 1 |
| 182 | $CH(CH_3)_2$ | 4-C(NH)$NH_2$ | N | 2 |
| 183 | $CH(CH_3)_2$ | 3-C(NH)$NH_2$ | N | 2 |
| 184 | $CH(CH_3)_2$ | 2-C(NH)$NH_2$ | N | 1 |
| 185 | $CH(CH_3)_2$ | 3-C(NH)$NH_2$ | N | 1 |

TABLE 2a

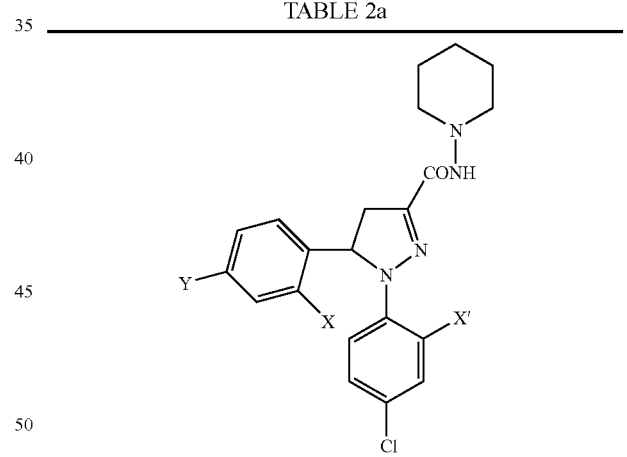

| Ex. # | X | Y | X' |
|---|---|---|---|
| 1 | $CO_2Et$ | H | H |
| 2 | $CO_2H$ | H | H |
| 3 | $CH_2CO_2Et$ | H | H |
| 4 | $CH_2CO_2H$ | H | H |
| 5 | $OCH_2CO_2Et$ | H | H |
| 6 | $OCH_2CO_2H$ | H | H |
| 7 | $OCH_2CH_2CH_2PO(OEt)_2$ | H | H |
| 8 | $OCH_2CH_2CH_2PO(OH)_2$ | H | H |
| 9 | $OCH_2C_6H_4CO_2Et$ | H | H |
| 10 | $OCH_2C_6H_4CO_2H$ | H | H |
| 11 | $NHCH_2CO_2Et$ | H | H |
| 12 | $NHCH_2CO_2H$ | H | H |
| 13 | $NHCH_2CH_2CH_2PO(OEt)_2$ | H | H |
| 14 | $NHCH_2CH_2CH_2PO(OH)_2$ | H | H |
| 15 | $NHCH_2C_6H_4CO_2Et$ | H | H |
| 16 | $NHCH_2C_6H_4CO_2H$ | H | H |

TABLE 2a-continued

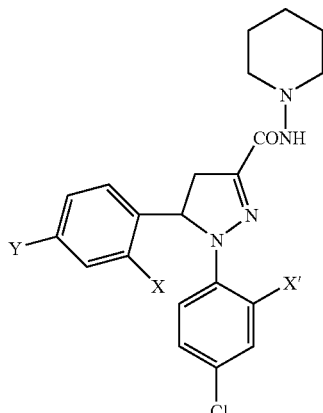

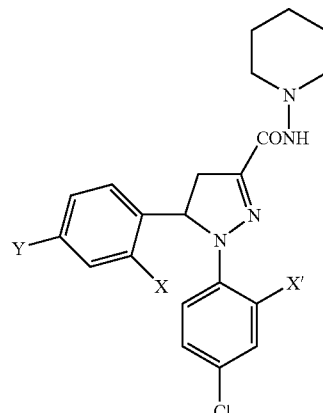

| Ex. # | X | Y | X' |
|---|---|---|---|
| 17 | NHCOCH$_2$CH$_2$CO$_2$Et | H | H |
| 18 | NHCOCH$_2$CH$_2$CO$_2$H | H | H |
| 19 | NHSO$_2$CH$_3$ | H | H |
| 20 | NHCH$_2$CH=CHCO$_2$Et | H | H |
| 21 | NHCH$_2$CH=CHCO$_2$H | H | H |
| 22 | CONH$_2$ | H | H |
| 23 | CH$_2$CONH$_2$ | H | H |
| 24 | OCH$_2$CONH$_2$ | H | H |
| 25 | CN$_4$H | H | H |
| 26 | H | CO$_2$Et | H |
| 27 | H | CO$_2$H | H |
| 28 | H | CH$_2$CO$_2$Et | H |
| 29 | H | CH$_2$CO$_2$H | H |
| 30 | H | OCH$_2$CO$_2$Et | H |
| 31 | H | OCH$_2$CO$_2$H | H |
| 32 | H | OCH$_2$CH$_2$CH$_2$PO(OEt)$_2$ | H |
| 33 | H | OCH$_2$CH$_2$CH$_2$PO(OH)$_2$ | H |
| 34 | H | OCH$_2$C$_6$H$_4$CO$_2$Et | H |
| 35 | H | OCH$_2$C$_6$H$_4$CO$_2$H | H |
| 36 | H | NHCH$_2$CO$_2$Et | H |
| 37 | H | NHCH$_2$CO$_2$H | H |
| 38 | H | NHCH$_2$CH$_2$CH$_2$PO(OEt)$_2$ | H |
| 39 | H | NHCH$_2$CH$_2$CH$_2$PO(OH)$_2$ | H |
| 40 | H | NHCH$_2$C$_6$H$_4$CO$_2$Et | H |
| 41 | H | NHCH$_2$C$_6$H$_4$CO$_2$H | H |
| 42 | H | NHCOCH$_2$CH$_2$CO$_2$Et | H |
| 43 | H | NHCOCH$_2$CH$_2$CO$_2$H | H |
| 44 | H | NHSO$_2$CH$_3$ | H |
| 45 | H | NHCH$_2$CH=CHCO$_2$Et | H |
| 46 | H | NHCH$_2$CH=CHCO$_2$H | H |
| 47 | H | CONH$_2$ | H |
| 48 | H | CH$_2$CONH$_2$ | H |
| 49 | H | OCH$_2$CONH$_2$ | H |
| 50 | H | CN$_4$H | H |
| 51 | CO$_2$Et | H | Cl |
| 52 | CO$_2$H | H | Cl |
| 53 | CH$_2$CO$_2$Et | H | Cl |
| 54 | CH$_2$CO$_2$H | H | Cl |
| 55 | OCH$_2$CO$_2$Et | H | Cl |
| 56 | OCH$_2$CO$_2$H | H | Cl |
| 57 | OCH$_2$CH$_2$CH$_2$PO(OEt)$_2$ | H | Cl |
| 58 | OCH$_2$CH$_2$CH$_2$PO(OH)$_2$ | H | Cl |
| 59 | OCH$_2$C$_6$H$_4$CO$_2$Et | H | Cl |
| 60 | OCH$_2$C$_6$H$_4$CO$_2$H | H | Cl |
| 61 | NHCH$_2$CO$_2$Et | H | Cl |
| 62 | NHCH$_2$CO$_2$H | H | Cl |
| 63 | NHCH$_2$CH$_2$CH$_2$PO(OEt)$_2$ | H | Cl |
| 64 | NHCH$_2$CH$_2$CH$_2$PO(OH)$_2$ | H | Cl |
| 65 | NHCH$_2$C$_6$H$_4$CO$_2$Et | H | Cl |
| 66 | NHCH$_2$C$_6$H$_4$CO$_2$H | H | Cl |
| 67 | NHCOCH$_2$CH$_2$CO$_2$Et | H | Cl |
| 68 | NHCOCH$_2$CH$_2$CO$_2$H | H | Cl |
| 69 | NHSO$_2$CH$_3$ | H | Cl |
| 70 | NHCH$_2$CH=CHCO$_2$Et | H | Cl |
| 71 | NHCH$_2$CH=CHCO$_2$H | H | Cl |
| 72 | CONH$_2$ | H | Cl |
| 73 | CH$_2$CONH$_2$ | H | Cl |
| 74 | OCH$_2$CONH$_2$ | H | Cl |
| 75 | CN$_4$H | H | Cl |
| 76 | H | CO$_2$Et | Cl |
| 77 | H | CO$_2$H | Cl |
| 78 | H | CH$_2$CO$_2$Et | Cl |
| 79 | H | CH$_2$CO$_2$H | Cl |
| 80 | H | OCH$_2$CO$_2$Et | Cl |
| 81 | H | OCH$_2$CO$_2$H | Cl |
| 82 | H | OCH$_2$CH$_2$CH$_2$PO(OEt)$_2$ | Cl |
| 83 | H | OCH$_2$CH$_2$CH$_2$PO(OH)$_2$ | Cl |
| 84 | H | OCH$_2$C$_6$H$_4$CO$_2$Et | Cl |
| 85 | H | OCH$_2$C$_6$H$_4$CO$_2$H | Cl |
| 86 | H | NHCH$_2$CO$_2$Et | Cl |
| 87 | H | NHCH$_2$CO$_2$H | Cl |
| 88 | H | NHCH$_2$CH$_2$CH$_2$PO(OEt)$_2$ | Cl |
| 89 | H | NHCH$_2$CH$_2$CH$_2$PO(OH)$_2$ | Cl |
| 90 | H | NHCH$_2$C$_6$H$_4$CO$_2$Et | Cl |
| 91 | H | NHCH$_2$C$_6$H$_4$CO$_2$H | Cl |
| 92 | H | NHCOCH$_2$CH$_2$CO$_2$Et | Cl |
| 93 | H | NHCOCH$_2$CH$_2$CO$_2$H | Cl |
| 94 | H | NHSO$_2$CH$_3$ | Cl |
| 95 | H | NHCH$_2$CH=CHCO$_2$Et | Cl |
| 96 | H | NHCH$_2$CH=CHCO$_2$H | Cl |
| 97 | H | CONH$_2$ | Cl |
| 98 | H | CH$_2$CONH$_2$ | Cl |
| 99 | H | OCH$_2$CONH$_2$ | Cl |
| 100 | H | CN$_4$H | Cl |
| 101 | CO$_2$Et | H | OCH$_3$ |
| 102 | CO$_2$H | H | OCH$_3$ |
| 103 | CH$_2$CO$_2$Et | H | OCH$_3$ |
| 104 | CH$_2$CO$_2$H | H | OCH$_3$ |
| 105 | OCH$_2$CO$_2$Et | H | OCH$_3$ |
| 106 | OCH$_2$CO$_2$H | H | OCH$_3$ |
| 107 | OCH$_2$CH$_2$CH$_2$PO(OEt)$_2$ | H | OCH$_3$ |
| 108 | OCH$_2$CH$_2$CH$_2$PO(OH)$_2$ | H | OCH$_3$ |
| 109 | OCH$_2$C$_6$H$_4$CO$_2$Et | H | OCH$_3$ |
| 110 | OCH$_2$C$_6$H$_4$CO$_2$H | H | OCH$_3$ |
| 111 | NHCH$_2$CO$_2$Et | H | OCH$_3$ |
| 112 | NHCH$_2$CO$_2$H | H | OCH$_3$ |
| 113 | NHCH$_2$CH$_2$CH$_2$PO(OEt)$_2$ | H | OCH$_3$ |
| 114 | NHCH$_2$CH$_2$CH$_2$PO(OH)$_2$ | H | OCH$_3$ |
| 115 | NHCH$_2$C$_6$H$_4$CO$_2$Et | H | OCH$_3$ |
| 116 | NHCH$_2$C$_6$H$_4$CO$_2$H | H | OCH$_3$ |
| 117 | NHCOCH$_2$CH$_2$CO$_2$Et | H | OCH$_3$ |
| 118 | NHCOCH$_2$CH$_2$CO$_2$H | H | OCH$_3$ |
| 119 | NHSO$_2$CH$_3$ | H | OCH$_3$ |
| 120 | NHCH$_2$CH=CHCO$_2$Et | H | OCH$_3$ |
| 121 | NHCH$_2$CH=CHCO$_2$H | H | OCH$_3$ |
| 122 | CONH$_2$ | H | OCH$_3$ |
| 123 | CH$_2$CONH$_2$ | H | OCH$_3$ |
| 124 | OCH$_2$CONH$_2$ | H | OCH$_3$ |
| 125 | CN$_4$H | H | OCH$_3$ |
| 126 | H | CO$_2$Et | OCH$_3$ |
| 127 | H | CO$_2$H | OCH$_3$ |
| 128 | H | CH$_2$CO$_2$Et | OCH$_3$ |
| 129 | H | CH$_2$CO$_2$H | OCH$_3$ |
| 130 | H | OCH$_2$CO$_2$Et | OCH$_3$ |

TABLE 2a-continued

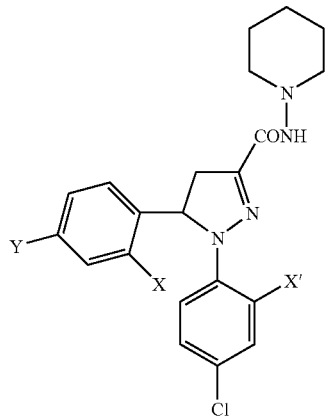
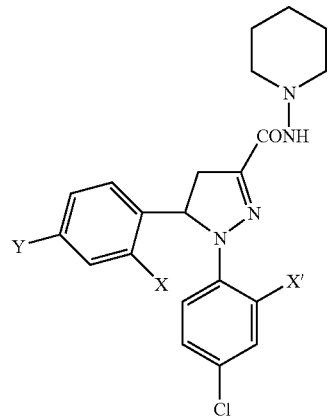

| Ex. # | X | Y | X' |
|---|---|---|---|
| 131 | H | OCH$_2$CO$_2$H | OCH$_3$ |
| 132 | H | OCH$_2$CH$_2$CH$_2$PO(OEt)$_2$ | OCH$_3$ |
| 133 | H | OCH$_2$CH$_2$CH$_2$PO(OH)$_2$ | OCH$_3$ |
| 134 | H | OCH$_2$C$_6$H$_4$CO$_2$Et | OCH$_3$ |
| 135 | H | OCH$_2$C$_6$H$_4$CO$_2$H | OCH$_3$ |
| 136 | H | NHCH$_2$CO$_2$Et | OCH$_3$ |
| 137 | H | NHCH$_2$CO$_2$H | OCH$_3$ |
| 138 | H | NHCH$_2$CH$_2$CH$_2$PO(OEt)$_2$ | OCH$_3$ |
| 139 | H | NHCH$_2$CH$_2$CH$_2$PO(OH)$_2$ | OCH$_3$ |
| 140 | H | NHCH$_2$C$_6$H$_4$CO$_2$Et | OCH$_3$ |
| 141 | H | NHCH$_2$C$_6$H$_4$CO$_2$H | OCH$_3$ |
| 142 | H | NHCOCH$_2$CH$_2$CO$_2$Et | OCH$_3$ |
| 143 | H | NHCOCH$_2$CH$_2$CO$_2$H | OCH$_3$ |
| 144 | H | NHSO$_2$CH$_3$ | OCH$_3$ |
| 145 | H | NHCH$_2$CH=CHCO$_2$Et | OCH$_3$ |
| 146 | H | NHCH$_2$CH=CHCO$_2$H | OCH$_3$ |
| 147 | H | CONH$_2$ | OCH$_3$ |
| 148 | H | CH$_2$CONH$_2$ | OCH$_3$ |
| 149 | H | OCH$_2$CONH$_2$ | OCH$_3$ |
| 150 | H | CN$_4$H | OCH$_3$ |
| 151 | CO$_2$Et | H | CH$_3$ |
| 152 | CO$_2$H | H | CH$_3$ |
| 153 | CH$_2$CO$_2$Et | H | CH$_3$ |
| 154 | CH$_2$CO$_2$H | H | CH$_3$ |
| 155 | OCH$_2$CO$_2$Et | H | CH$_3$ |
| 156 | OCH$_2$CO$_2$H | H | CH$_3$ |
| 157 | OCH$_2$CH$_2$CH$_2$PO(OEt)$_2$ | H | CH$_3$ |
| 158 | OCH$_2$CH$_2$CH$_2$PO(OH)$_2$ | H | CH$_3$ |
| 159 | OCH$_2$C$_6$H$_4$CO$_2$Et | H | CH$_3$ |
| 160 | OCH$_2$C$_6$H$_4$CO$_2$H | H | CH$_3$ |
| 161 | NHCH$_2$CO$_2$Et | H | CH$_3$ |
| 162 | NHCH$_2$CO$_2$H | H | CH$_3$ |
| 163 | NHCH$_2$CH$_2$CH$_2$PO(OEt)$_2$ | H | CH$_3$ |
| 164 | NHCH$_2$CH$_2$CH$_2$PO(OH)$_2$ | H | CH$_3$ |
| 165 | NHCH$_2$C$_6$H$_4$CO$_2$Et | H | CH$_3$ |
| 166 | NHCH$_2$C$_6$H$_4$CO$_2$H | H | CH$_3$ |
| 167 | NHCOCH$_2$CH$_2$CO$_2$Et | H | CH$_3$ |
| 168 | NHCOCH$_2$CH$_2$CO$_2$H | H | CH$_3$ |
| 69 | NHSO$_2$CH$_3$ | H | CH$_3$ |
| 170 | NHCH$_2$CH=CHCO$_2$Et | H | CH$_3$ |
| 171 | NHCH$_2$CH=CHCO$_2$H | H | CH$_3$ |
| 172 | CONH$_2$ | H | CH$_3$ |
| 173 | CH$_2$CONH$_2$ | H | CH$_3$ |
| 174 | OCH$_2$CONH$_2$ | H | CH$_3$ |
| 175 | CN$_4$H | H | CH$_3$ |
| 176 | H | CO$_2$Et | CH$_3$ |
| 177 | H | CO$_2$H | CH$_3$ |
| 178 | H | CH$_2$CO$_2$Et | CH$_3$ |
| 179 | H | CH$_2$CO$_2$H | CH$_3$ |
| 180 | H | OCH$_2$CO$_2$Et | CH$_3$ |
| 181 | H | OCH$_2$CO$_2$H | CH$_3$ |
| 182 | H | OCH$_2$CH$_2$CH$_2$PO(OEt)$_2$ | CH$_3$ |
| 183 | H | OCH$_2$CH$_2$CH$_2$PO(OH)$_2$ | CH$_3$ |
| 184 | H | OCH$_2$C$_6$H$_4$CO$_2$Et | CH$_3$ |
| 185 | H | OCH$_2$C$_6$H$_4$CO$_2$H | CH$_3$ |
| 186 | H | NHCH$_2$CO$_2$Et | CH$_3$ |
| 187 | H | NHCH$_2$CO$_2$H | CH$_3$ |
| 188 | H | NHCH$_2$CH$_2$CH$_2$PO(OEt)$_2$ | CH$_3$ |
| 189 | H | NHCH$_2$CH$_2$CH$_2$PO(OH)$_2$ | CH$_3$ |
| 190 | H | NHCH$_2$C$_6$H$_4$CO$_2$Et | CH$_3$ |
| 191 | H | NHCH$_2$C$_6$H$_4$CO$_2$H | CH$_3$ |
| 192 | H | NHCOCH$_2$CH$_2$CO$_2$Et | CH$_3$ |
| 193 | H | NHCOCH$_2$CH$_2$CO$_2$H | CH$_3$ |
| 194 | H | NHSO$_2$CH$_3$ | CH$_3$ |
| 195 | H | NHCH$_2$CH=CHCO$_2$Et | CH$_3$ |
| 196 | H | NHCH$_2$CH=CHCO$_2$H | CH$_3$ |
| 197 | H | CONH$_2$ | CH$_3$ |
| 198 | H | CH$_2$CONH$_2$ | CH$_3$ |
| 199 | H | OCH$_2$CONH$_2$ | CH$_3$ |
| 200 | H | CN$_4$H | CH$_3$ |
| 201 | CO$_2$Et | Cl | H |
| 202 | CO$_2$H | Cl | H |
| 203 | CH$_2$CO$_2$Et | Cl | H |
| 204 | CH$_2$CO$_2$H | Cl | H |
| 205 | OCH$_2$CO$_2$Et | Cl | H |
| 206 | OCH$_2$CO$_2$H | Cl | H |
| 207 | OCH$_2$CH$_2$CH$_2$PO(OEt)$_2$ | Cl | H |
| 208 | OCH$_2$CH$_2$CH$_2$PO(OH)$_2$ | Cl | H |
| 209 | OCH$_2$C$_6$H$_4$CO$_2$Et | Cl | H |
| 210 | OCH$_2$C$_6$H$_4$CO$_2$H | Cl | H |
| 211 | NHCH$_2$CO$_2$Et | Cl | H |
| 212 | NHCH$_2$CO$_2$H | Cl | H |
| 213 | NHCH$_2$CH$_2$CH$_2$PO(OEt)$_2$ | Cl | H |
| 214 | NHCH$_2$CH$_2$CH$_2$PO(OH)$_2$ | Cl | H |
| 215 | NHCH$_2$C$_6$H$_4$CO$_2$Et | Cl | H |
| 216 | NHCH$_2$C$_6$H$_4$CO$_2$H | Cl | H |
| 217 | NHCOCH$_2$CH$_2$CO$_2$Et | Cl | H |
| 218 | NHCOCH$_2$CH$_2$CO$_2$H | Cl | H |
| 219 | NHSO$_2$CH$_3$ | Cl | H |
| 220 | NHCH$_2$CH=CHCO$_2$Et | Cl | H |
| 221 | NHCH$_2$CH=CHCO$_2$H | Cl | H |
| 222 | CONH$_2$ | Cl | H |
| 223 | CH$_2$CONH$_2$ | Cl | H |
| 224 | OCH$_2$CONH$_2$ | Cl | H |
| 225 | CN$_4$H | Cl | H |
| 226 | Cl | CO$_2$Et | H |
| 227 | Cl | CO$_2$H | H |
| 228 | Cl | CH$_2$CO$_2$Et | H |
| 229 | Cl | CH$_2$CO$_2$H | H |
| 230 | Cl | OCH$_2$CO$_2$Et | H |
| 231 | Cl | OCH$_2$CO$_2$H | H |
| 232 | Cl | OCH$_2$CH$_2$CH$_2$PO(OEt)$_2$ | H |
| 233 | Cl | OCH$_2$CH$_2$CH$_2$PO(OH)$_2$ | H |
| 234 | Cl | OCH$_2$C$_6$H$_4$CO$_2$Et | H |
| 235 | Cl | OCH$_2$C$_6$H$_4$CO$_2$H | H |
| 236 | Cl | NHCH$_2$CO$_2$Et | H |
| 237 | Cl | NHCH$_2$CO$_2$H | H |
| 238 | Cl | NHCH$_2$CH$_2$CH$_2$PO(OEt)$_2$ | H |
| 239 | Cl | NHCH$_2$CH$_2$CH$_2$PO(OH)$_2$ | H |
| 240 | Cl | NHCH$_2$C$_6$H$_4$CO$_2$Et | H |
| 241 | Cl | NHCH$_2$C$_6$H$_4$CO$_2$H | H |
| 242 | Cl | NHCOCH$_2$CH$_2$CO$_2$Et | H |
| 243 | Cl | NHCOCH$_2$CH$_2$CO$_2$H | H |
| 244 | Cl | NHSO$_2$CH$_3$ | H |

TABLE 2a-continued

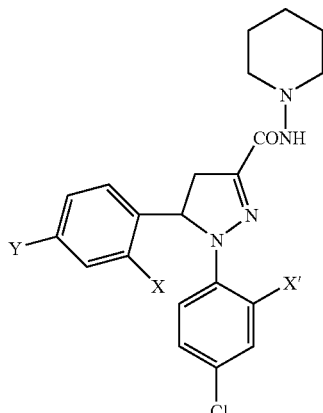

| Ex. # | X | Y | X' |
|---|---|---|---|
| 245 | Cl | NHCH$_2$CH=CHCO$_2$Et | H |
| 246 | Cl | NHCH$_2$CH=CHCO$_2$H | H |
| 247 | Cl | CONH$_2$ | H |
| 248 | Cl | CH$_2$CONH$_2$ | H |
| 249 | Cl | OCH$_2$CONH$_2$ | H |
| 250 | Cl | CN$_4$H | H |
| 251 | CO$_2$Et | Cl | Cl |
| 252 | CO$_2$H | Cl | Cl |
| 253 | CH$_2$CO$_2$Et | Cl | Cl |
| 254 | CH$_2$CO$_2$H | Cl | Cl |
| 255 | OCH$_2$CO$_2$Et | Cl | Cl |
| 256 | OCH$_2$CO$_2$H | Cl | Cl |
| 257 | OCH$_2$CH$_2$CH$_2$PO(OEt)$_2$ | Cl | Cl |
| 258 | OCH$_2$CH$_2$CH$_2$PO(OH)$_2$ | Cl | Cl |
| 259 | OCH$_2$C$_6$H$_4$CO$_2$Et | Cl | Cl |
| 260 | OCH$_2$C$_6$H$_4$CO$_2$H | Cl | Cl |
| 261 | NHCH$_2$CO$_2$Et | Cl | Cl |
| 262 | NHCH$_2$CO$_2$H | Cl | Cl |
| 263 | NHCH$_2$CH$_2$CH$_2$PO(OEt)$_2$ | Cl | Cl |
| 264 | NHCH$_2$CH$_2$CH$_2$PO(OH)$_2$ | Cl | Cl |
| 265 | NHCH$_2$C$_6$H$_4$CO$_2$Et | Cl | Cl |
| 266 | NHCH$_2$C$_6$H$_4$CO$_2$H | Cl | Cl |
| 267 | NHCOCH$_2$CH$_2$CO$_2$Et | Cl | Cl |
| 268 | NHCOCH$_2$CH$_2$CO$_2$H | Cl | Cl |
| 269 | NHSO$_2$CH$_3$ | Cl | Cl |
| 270 | NHCH$_2$CH=CHCO$_2$Et | Cl | Cl |
| 271 | NHCH$_2$CH=CHCO$_2$H | Cl | Cl |
| 272 | CONH$_2$ | Cl | Cl |
| 273 | CH$_2$CONH$_2$ | Cl | Cl |
| 274 | OCH$_2$CONH$_2$ | Cl | Cl |
| 275 | CN$_4$H | Cl | Cl |
| 276 | Cl | CO$_2$Et | Cl |
| 277 | Cl | CO$_2$H | Cl |
| 278 | Cl | CH$_2$CO$_2$Et | Cl |
| 279 | Cl | CH$_2$CO$_2$H | Cl |
| 280 | Cl | OCH$_2$CO$_2$Et | Cl |
| 281 | Cl | OCH$_2$CO$_2$H | Cl |
| 282 | Cl | OCH$_2$CH$_2$CH$_2$PO(OEt)$_2$ | Cl |
| 283 | Cl | OCH$_2$CH$_2$CH$_2$PO(OH)$_2$ | Cl |
| 284 | Cl | OCH$_2$C$_6$H$_4$CO$_2$Et | Cl |
| 285 | Cl | OCH$_2$C$_6$H$_4$CO$_2$H | Cl |
| 286 | Cl | NHCH$_2$CO$_2$Et | Cl |
| 287 | Cl | NHCH$_2$CO$_2$H | Cl |
| 288 | Cl | NHCH$_2$CH$_2$CH$_2$PO(OEt)$_2$ | Cl |
| 289 | Cl | NHCH$_2$CH$_2$CH$_2$PO(OH)$_2$ | Cl |
| 290 | Cl | NHCH$_2$C$_6$H$_4$CO$_2$Et | Cl |
| 291 | Cl | NHCH$_2$C$_6$H$_4$CO$_2$H | Cl |
| 292 | Cl | NHCOCH$_2$CH$_2$CO$_2$Et | Cl |
| 293 | Cl | NHCOCH$_2$CH$_2$CO$_2$H | Cl |
| 294 | Cl | NHSO$_2$CH$_3$ | Cl |
| 295 | Cl | NHCH$_2$CH=CHCO$_2$Et | Cl |
| 296 | Cl | NHCH$_2$CH=CHCO$_2$H | Cl |
| 297 | Cl | CONH$_2$ | Cl |
| 298 | Cl | CH$_2$CONH$_2$ | Cl |
| 299 | Cl | OCH$_2$CONH$_2$ | Cl |
| 300 | Cl | CN$_4$H | Cl |
| 301 | CO$_2$Et | Cl | OCH$_3$ |

TABLE 2a-continued

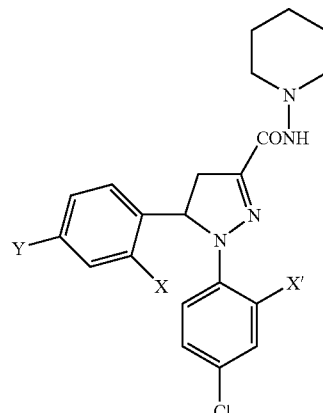

| Ex. # | X | Y | X' |
|---|---|---|---|
| 302 | CO$_2$H | Cl | OCH$_3$ |
| 303 | CH$_2$CO$_2$Et | Cl | OCH$_3$ |
| 304 | CH$_2$CO$_2$H | Cl | OCH$_3$ |
| 305 | OCH$_2$CO$_2$Et | Cl | OCH$_3$ |
| 306 | OCH$_2$CO$_2$H | Cl | OCH$_3$ |
| 307 | OCH$_2$CH$_2$CH$_2$PO(OEt)$_2$ | Cl | OCH$_3$ |
| 308 | OCH$_2$CH$_2$CH$_2$PO(OH)$_2$ | Cl | OCH$_3$ |
| 309 | OCH$_2$C$_6$H$_4$CO$_2$Et | Cl | OCH$_3$ |
| 310 | OCH$_2$C$_6$H$_4$CO$_2$H | Cl | OCH$_3$ |
| 311 | NHCH$_2$CO$_2$Et | Cl | OCH$_3$ |
| 312 | NHCH$_2$CO$_2$H | Cl | OCH$_3$ |
| 313 | NHCH$_2$CH$_2$CH$_2$PO(OEt)$_2$ | Cl | OCH$_3$ |
| 314 | NHCH$_2$CH$_2$CH$_2$PO(OH)$_2$ | Cl | OCH$_3$ |
| 315 | NHCH$_2$C$_6$H$_4$CO$_2$Et | Cl | OCH$_3$ |
| 316 | NHCH$_2$C$_6$H$_4$CO$_2$H | Cl | OCH$_3$ |
| 317 | NHCOCH$_2$CH$_2$CO$_2$Et | Cl | OCH$_3$ |
| 318 | NHCOCH$_2$CH$_2$CO$_2$H | Cl | OCH$_3$ |
| 319 | NHSO$_2$CH$_3$ | Cl | OCH$_3$ |
| 320 | NHCH$_2$CH=CHCO$_2$Et | Cl | OCH$_3$ |
| 321 | NHCH$_2$CH=CHCO$_2$H | Cl | OCH$_3$ |
| 322 | CONH$_2$ | Cl | OCH$_3$ |
| 323 | CH$_2$CONH$_2$ | Cl | OCH$_3$ |
| 324 | OCH$_2$CONH$_2$ | Cl | OCH$_3$ |
| 325 | CN$_4$H | Cl | OCH$_3$ |
| 326 | Cl | CO$_2$Et | OCH$_3$ |
| 327 | Cl | CO$_2$H | OCH$_3$ |
| 328 | Cl | CH$_2$CO$_2$Et | OCH$_3$ |
| 329 | Cl | CH$_2$CO$_2$H | OCH$_3$ |
| 330 | Cl | OCH$_2$CO$_2$Et | OCH$_3$ |
| 331 | Cl | OCH$_2$CO$_2$H | OCH$_3$ |
| 332 | Cl | OCH$_2$CH$_2$CH$_2$PO(OEt)$_2$ | OCH$_3$ |
| 333 | Cl | OCH$_2$CH$_2$CH$_2$PO(OH)$_2$ | OCH$_3$ |
| 334 | Cl | OCH$_2$C$_6$H$_4$CO$_2$Et | OCH$_3$ |
| 335 | Cl | OCH$_2$C$_6$H$_4$CO$_2$H | OCH$_3$ |
| 336 | Cl | NHCH$_2$CO$_2$Et | OCH$_3$ |
| 337 | Cl | NHCH$_2$CO$_2$H | OCH$_3$ |
| 338 | Cl | NHCH$_2$CH$_2$CH$_2$PO(OEt)$_2$ | OCH$_3$ |
| 339 | Cl | NHCH$_2$CH$_2$CH$_2$PO(OH)$_2$ | OCH$_3$ |
| 340 | Cl | NHCH$_2$C$_6$H$_4$CO$_2$Et | OCH$_3$ |
| 341 | Cl | NHCH$_2$C$_6$H$_4$CO$_2$H | OCH$_3$ |
| 342 | Cl | NHCOCH$_2$CH$_2$CO$_2$Et | OCH$_3$ |
| 343 | Cl | NHCOCH$_2$CH$_2$CO$_2$H | OCH$_3$ |
| 344 | Cl | NHSO$_2$CH$_3$ | OCH$_3$ |
| 345 | Cl | NHCH$_2$CH=CHCO$_2$Et | OCH$_3$ |
| 346 | Cl | NHCH$_2$CH=CHCO$_2$H | OCH$_3$ |
| 347 | Cl | CONH$_2$ | OCH$_3$ |
| 348 | Cl | CH$_2$CONH$_2$ | OCH$_3$ |
| 349 | Cl | OCH$_2$CONH$_2$ | OCH$_3$ |
| 350 | Cl | CN$_4$H | OCH$_3$ |
| 351 | CO$_2$Et | Cl | CH$_3$ |
| 352 | CO$_2$H | Cl | CH$_3$ |
| 353 | CH$_2$CO$_2$Et | Cl | CH$_3$ |
| 354 | CH$_2$CO$_2$H | Cl | CH$_3$ |
| 355 | OCH$_2$CO$_2$Et | Cl | CH$_3$ |
| 356 | OCH$_2$CO$_2$H | Cl | CH$_3$ |
| 357 | OCH$_2$CH$_2$CH$_2$PO(OEt)$_2$ | Cl | CH$_3$ |
| 358 | OCH$_2$CH$_2$CH$_2$PO(OH)$_2$ | Cl | CH$_3$ |

TABLE 2a-continued

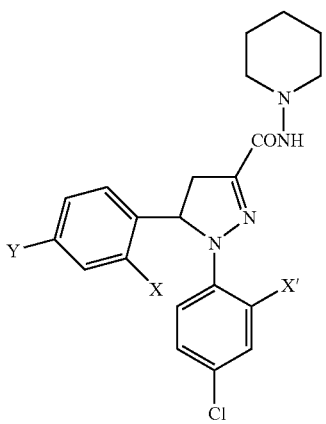

| Ex. # | X | Y | X' |
|---|---|---|---|
| 359 | OCH$_2$C$_6$H$_4$CO$_2$Et | Cl | CH$_3$ |
| 360 | OCH$_2$C$_6$H$_4$CO$_2$H | Cl | CH$_3$ |
| 361 | NHCH$_2$CO$_2$Et | Cl | CH$_3$ |
| 362 | NHCH$_2$CO$_2$H | Cl | CH$_3$ |
| 363 | NHCH$_2$CH$_2$CH$_2$PO(OEt)$_2$ | Cl | CH$_3$ |
| 364 | NHCH$_2$CH$_2$CH$_2$PO(OH)$_2$ | Cl | CH$_3$ |
| 365 | NHCH$_2$C$_6$H$_4$CO$_2$Et | Cl | CH$_3$ |
| 366 | NHCH$_2$C$_6$H$_4$CO$_2$H | Cl | CH$_3$ |
| 367 | NHCOCH$_2$CH$_2$CO$_2$Et | Cl | CH$_3$ |
| 368 | NHCOCH$_2$CH$_2$CO$_2$H | Cl | CH$_3$ |
| 369 | NHSO$_2$CH$_3$ | Cl | CH$_3$ |
| 370 | NHCH$_2$CH=CHCO$_2$Et | Cl | CH$_3$ |
| 371 | NHCH$_2$CH=CHCO$_2$H | Cl | CH$_3$ |
| 372 | CONH$_2$ | Cl | CH$_3$ |
| 373 | CH$_2$CONH$_2$ | Cl | CH$_3$ |
| 374 | OCH$_2$CONH$_2$ | Cl | CH$_3$ |
| 375 | CN$_4$H | Cl | CH$_3$ |
| 376 | Cl | CO$_2$Et | CH$_3$ |
| 377 | Cl | CO$_2$H | CH$_3$ |
| 378 | Cl | CH$_2$CO$_2$Et | CH$_3$ |
| 379 | Cl | CH$_2$CO$_2$H | CH$_3$ |
| 380 | Cl | OCH$_2$CO$_2$Et | CH$_3$ |
| 381 | Cl | OCH$_2$CO$_2$H | CH$_3$ |
| 382 | Cl | OCH$_2$CH$_2$CH$_2$PO(OEt)$_2$ | CH$_3$ |
| 383 | Cl | OCH$_2$CH$_2$CH$_2$PO(OH)$_2$ | CH$_3$ |
| 384 | Cl | OCH$_2$C$_6$H$_4$CO$_2$Et | CH$_3$ |
| 385 | Cl | OCH$_2$C$_6$H$_4$CO$_2$H | CH$_3$ |
| 386 | Cl | NHCH$_2$CO$_2$Et | CH$_3$ |
| 387 | Cl | NHCH$_2$CO$_2$H | CH$_3$ |
| 388 | Cl | NHCH$_2$CH$_2$CH$_2$PO(OEt)$_2$ | CH$_3$ |
| 389 | Cl | NHCH$_2$CH$_2$CH$_2$PO(OH)$_2$ | CH$_3$ |
| 390 | Cl | NHCH$_2$C$_6$H$_4$CO$_2$Et | CH$_3$ |
| 391 | Cl | NHCH$_2$C$_6$H$_4$CO$_2$H | CH$_3$ |
| 392 | Cl | NHCOCH$_2$CH$_2$CO$_2$Et | CH$_3$ |
| 393 | Cl | NHCOCH$_2$CH$_2$CO$_2$H | CH$_3$ |
| 394 | Cl | NHSO$_2$CH$_3$ | CH$_3$ |
| 395 | Cl | NHCH$_2$CH=CHCO$_2$Et | CH$_3$ |
| 396 | Cl | NHCH$_2$CH=CHCO$_2$H | CH$_3$ |
| 397 | Cl | CONH$_2$ | CH$_3$ |
| 398 | Cl | CH$_2$CONH$_2$ | CH$_3$ |
| 399 | Cl | OCH$_2$CONH$_2$ | CH$_3$ |
| 400 | Cl | CN$_4$H | CH$_3$ |

TABLE 2b

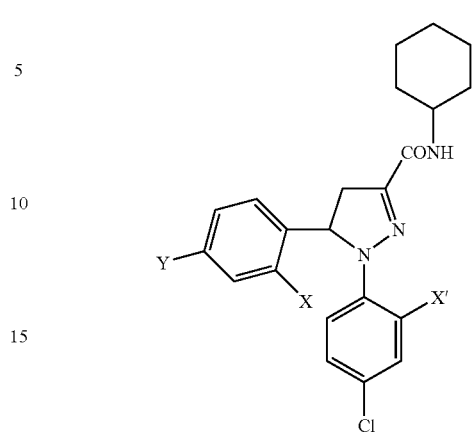

Examples 1-400 of Table 2b correspond to Examples 1-400 of Table 2a, except that they are based on formula B instead of formula A.

TABLE 3a

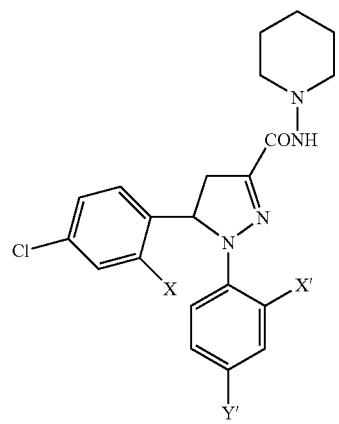

Examples 1-400 of Table 3a correspond to Examples 1-400 of Table 2a, except that they are based on formula C instead of formula A.

TABLE 3b

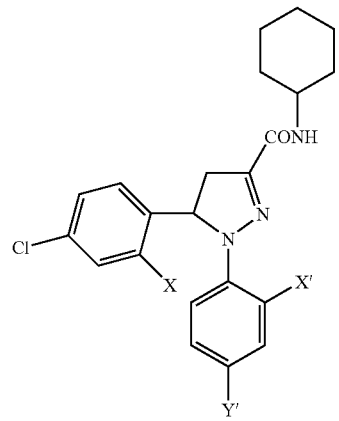

Examples 1-400 of Table 3b correspond to Examples 1-400 of Table 2a, except that they are based on formula D instead of formula A.

TABLE 4

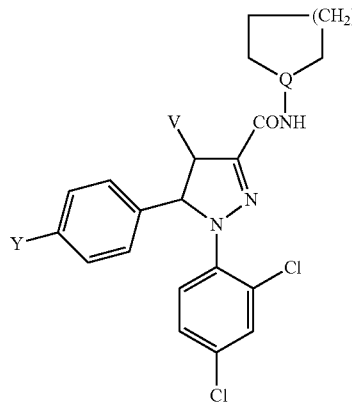

| Ex. # | Y | V | Q | n |
|---|---|---|---|---|
| 1 | Cl | CONH$_2$ | N | 1 |
| 2 | Cl | CN$_4$H | N | 1 |
| 3 | CH$_3$ | CONH$_2$ | N | 1 |
| 4 | CH$_3$ | CN$_4$H | N | 1 |
| 5 | OCH$_3$ | CONH$_2$ | N | 1 |
| 6 | OCH$_3$ | CN$_4$H | N | 1 |
| 7 | CH(CH$_3$)$_2$ | CONH$_2$ | N | 1 |
| 8 | CH(CH$_3$)$_2$ | CN$_4$H | N | 1 |
| 9 | Cl | CONH$_2$ | N | 2 |
| 10 | Cl | CN$_4$H | N | 2 |
| 11 | CH$_3$ | CONH$_2$ | N | 2 |
| 12 | CH$_3$ | CN$_4$H | N | 2 |
| 13 | OCH$_3$ | CONH$_2$ | N | 2 |
| 14 | OCH$_3$ | CN$_4$H | N | 2 |
| 15 | CH(CH$_3$)$_2$ | CONH$_2$ | N | 2 |
| 16 | CH(CH$_3$)$_2$ | CN$_4$H | N | 2 |
| 17 | Cl | CONH$_2$ | CH | 1 |
| 18 | Cl | CN$_4$H | CH | 1 |
| 19 | CH$_3$ | CONH$_2$ | CH | 1 |
| 20 | CH$_3$ | CN$_4$H | CH | 1 |
| 21 | OCH$_3$ | CONH$_2$ | CH | 1 |
| 22 | OCH$_3$ | CN$_4$H | CH | 1 |
| 23 | CH(CH$_3$)$_2$ | CONH$_2$ | CH | 1 |
| 24 | CH(CH$_3$)$_2$ | CN$_4$H | CH | 1 |
| 25 | Cl | CONH$_2$ | CH | 2 |
| 26 | Cl | CN$_4$H | CH | 2 |
| 27 | CH$_3$ | CONH$_2$ | CH | 2 |
| 28 | CH$_3$ | CN$_4$H | CH | 2 |
| 29 | OCH$_3$ | CONH$_2$ | CH | 2 |
| 30 | OCH$_3$ | CN$_4$H | CH | 2 |
| 31 | CH(CH$_3$)$_2$ | CONH$_2$ | CH | 2 |
| 32 | CH(CH$_3$)$_2$ | CN$_4$H | CH | 2 |

TABLE 5a

| Ex. # | Y | R | A | m |
|---|---|---|---|---|
| 1 | Cl | Et | H | 0 |
| 2 | Cl | H | H | 0 |
| 3 | Cl | Et | H | 1 |
| 4 | Cl | H | H | 1 |
| 5 | Cl | Et | H | 3 |
| 6 | Cl | H | H | 3 |
| 7 | Cl | Et | CH$_3$ | 0 |
| 8 | Cl | H | CH$_3$ | 0 |
| 9 | Cl | Et | CH$_3$ | 2 |
| 10 | Cl | H | CH$_3$ | 2 |
| 11 | Cl | Et | C$_6$H$_5$ | 0 |
| 12 | Cl | H | C$_6$H$_5$ | 0 |
| 13 | Cl | Et | CH$_2$C$_6$H$_5$ | 0 |
| 14 | Cl | H | CH$_2$C$_6$H$_5$ | 0 |
| 15 | CH$_3$ | Et | H | 0 |
| 16 | CH$_3$ | H | H | 0 |
| 17 | CH$_3$ | Et | H | 1 |
| 18 | CH$_3$ | H | H | 1 |
| 19 | CH$_3$ | Et | H | 3 |
| 20 | CH$_3$ | H | H | 3 |
| 21 | CH$_3$ | Et | CH$_3$ | 0 |
| 22 | CH$_3$ | H | CH$_3$ | 0 |
| 23 | CH$_3$ | Et | CH$_3$ | 2 |
| 24 | CH$_3$ | H | CH$_3$ | 2 |
| 25 | CH$_3$ | Et | C$_6$H$_5$ | 0 |
| 26 | CH$_3$ | H | C$_6$H$_5$ | 0 |
| 27 | CH$_3$ | Et | CH$_2$C$_6$H$_5$ | 0 |
| 28 | CH$_3$ | H | CH$_2$C$_6$H$_5$ | 0 |
| 29 | OCH$_3$ | Et | H | 0 |
| 30 | OCH$_3$ | H | H | 0 |
| 31 | OCH$_3$ | Et | H | 1 |
| 32 | OCH$_3$ | H | H | 1 |
| 33 | OCH$_3$ | Et | H | 3 |
| 34 | OCH$_3$ | H | H | 3 |
| 35 | OCH$_3$ | Et | CH$_3$ | 0 |
| 36 | OCH$_3$ | H | CH$_3$ | 0 |
| 37 | OCH$_3$ | Et | CH$_3$ | 2 |
| 38 | OCH$_3$ | H | CH$_3$ | 2 |
| 39 | OCH$_3$ | Et | C$_6$H$_5$ | 0 |
| 40 | OCH$_3$ | H | C$_6$H$_5$ | 0 |
| 41 | OCH$_3$ | Et | CH$_2$C$_6$H$_5$ | 0 |
| 42 | OCH$_3$ | H | CH$_2$C$_6$H$_5$ | 0 |
| 43 | CH(CH$_3$)$_2$ | Et | H | 0 |
| 44 | CH(CH$_3$)$_2$ | H | H | 0 |
| 45 | CH(CH$_3$)$_2$ | Et | H | 1 |
| 46 | CH(CH$_3$)$_2$ | H | H | 1 |
| 47 | CH(CH$_3$)$_2$ | Et | H | 3 |
| 48 | CH(CH$_3$)$_2$ | H | H | 3 |
| 49 | CH(CH$_3$)$_2$ | Et | CH$_3$ | 0 |
| 50 | CH(CH$_3$)$_2$ | H | CH$_3$ | 0 |
| 51 | CH(CH$_3$)$_2$ | Et | CH$_3$ | 2 |
| 52 | CH(CH$_3$)$_2$ | H | CH$_3$ | 2 |
| 53 | CH(CH$_3$)$_2$ | Et | C$_6$H$_5$ | 0 |
| 54 | CH(CH$_3$)$_2$ | H | C$_6$H$_5$ | 0 |
| 55 | CH(CH$_3$)$_2$ | Et | CH$_2$C$_6$H$_5$ | 0 |
| 56 | CH(CH$_3$)$_2$ | H | CH$_2$C$_6$H$_5$ | 0 |
| 57 | Cl | Et | C(CH$_3$)$_3$ | 0 |
| 58 | Cl | H | C(CH$_3$)$_3$ | 0 |
| 59 | Cl | Et | C(CH$_3$)$_3$ | 1 |

TABLE 5a-continued

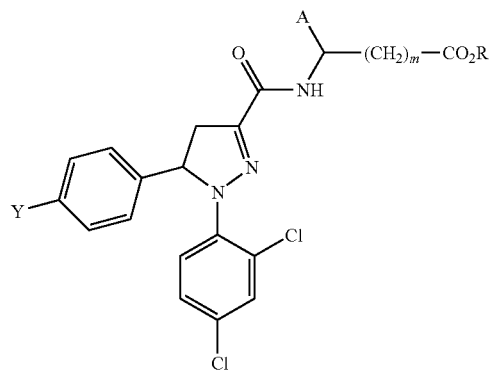

| Ex. # | Y  | R  | A         | m |
|-------|----|----|-----------|---|
| 60    | Cl | H  | C(CH$_3$)$_3$ | 1 |
| 61    | Cl | Et | C(CH$_3$)$_3$ | 2 |
| 62    | Cl | H  | C(CH$_3$)$_3$ | 2 |

TABLE 5b

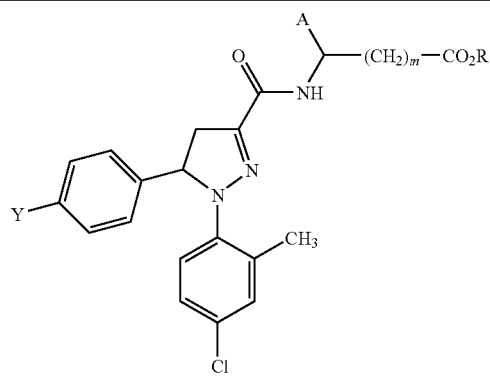

| Ex. # | Y       | R  | A             | m |
|-------|---------|----|---------------|---|
| 1     | Cl      | Et | H             | 0 |
| 2     | Cl      | H  | H             | 0 |
| 3     | Cl      | Et | H             | 1 |
| 4     | Cl      | H  | H             | 1 |
| 5     | Cl      | Et | H             | 3 |
| 6     | Cl      | H  | H             | 3 |
| 7     | Cl      | Et | C(CH$_3$)$_3$ | 0 |
| 8     | Cl      | H  | C(CH$_3$)$_3$ | 0 |
| 9     | Cl      | Et | C(CH$_3$)$_3$ | 2 |
| 10    | Cl      | H  | C(CH$_3$)$_3$ | 2 |
| 11    | Cl      | Et | C$_6$H$_5$    | 0 |
| 12    | Cl      | H  | C$_6$H$_5$    | 0 |
| 13    | Cl      | Et | CH$_2$C$_6$H$_5$ | 0 |
| 14    | Cl      | H  | CH$_2$C$_6$H$_5$ | 0 |
| 15    | CH$_3$  | Et | H             | 0 |
| 16    | CH$_3$  | H  | H             | 0 |
| 17    | CH$_3$  | Et | H             | 1 |
| 18    | CH$_3$  | H  | H             | 1 |
| 19    | CH$_3$  | Et | H             | 3 |
| 20    | CH$_3$  | H  | H             | 3 |
| 21    | CH$_3$  | Et | C(CH$_3$)$_3$ | 0 |
| 22    | CH$_3$  | H  | C(CH$_3$)$_3$ | 0 |
| 23    | CH$_3$  | Et | C(CH$_3$)$_3$ | 2 |
| 24    | CH$_3$  | H  | C(CH$_3$)$_3$ | 2 |
| 25    | CH$_3$  | Et | C$_6$H$_5$    | 0 |
| 26    | CH$_3$  | H  | C$_6$H$_5$    | 0 |
| 27    | CH$_3$  | Et | CH$_2$C$_6$H$_5$ | 0 |
| 28    | CH$_3$  | H  | CH$_2$C$_6$H$_5$ | 0 |
| 29    | OCH$_3$ | Et | H             | 0 |
| 30    | OCH$_3$ | H  | H             | 0 |
| 31    | OCH$_3$ | Et | H             | 1 |

TABLE 5b-continued

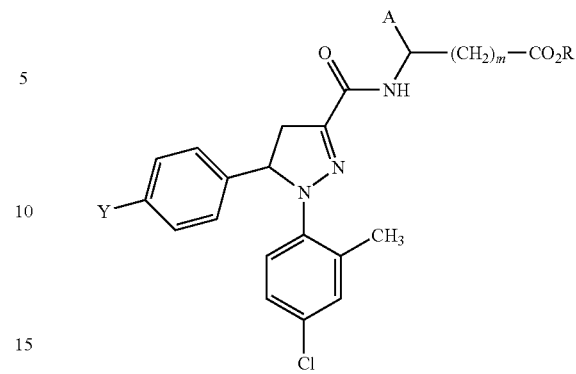

| Ex. # | Y           | R  | A             | m |
|-------|-------------|----|---------------|---|
| 32    | OCH$_3$     | H  | H             | 1 |
| 33    | OCH$_3$     | Et | H             | 3 |
| 34    | OCH$_3$     | H  | H             | 3 |
| 35    | OCH$_3$     | Et | C(CH$_3$)$_3$ | 0 |
| 36    | OCH$_3$     | H  | C(CH$_3$)$_3$ | 0 |
| 37    | OCH$_3$     | Et | C(CH$_3$)$_3$ | 2 |
| 38    | OCH$_3$     | H  | C(CH$_3$)$_3$ | 2 |
| 39    | OCH$_3$     | Et | C$_6$H$_5$    | 0 |
| 40    | OCH$_3$     | H  | C$_6$H$_5$    | 0 |
| 41    | OCH$_3$     | Et | CH$_2$C$_6$H$_5$ | 0 |
| 42    | OCH$_3$     | H  | CH$_2$C$_6$H$_5$ | 0 |
| 43    | CH(CH$_3$)$_2$ | Et | H          | 0 |
| 44    | CH(CH$_3$)$_2$ | H  | H          | 0 |
| 45    | CH(CH$_3$)$_2$ | Et | H          | 1 |
| 46    | CH(CH$_3$)$_2$ | H  | H          | 1 |
| 47    | CH(CH$_3$)$_2$ | Et | H          | 3 |
| 48    | CH(CH$_3$)$_2$ | H  | H          | 3 |
| 49    | CH(CH$_3$)$_2$ | Et | C(CH$_3$)$_3$ | 0 |
| 50    | CH(CH$_3$)$_2$ | H  | C(CH$_3$)$_3$ | 0 |
| 51    | CH(CH$_3$)$_2$ | Et | C(CH$_3$)$_3$ | 2 |
| 52    | CH(CH$_3$)$_2$ | H  | C(CH$_3$)$_3$ | 2 |
| 53    | CH(CH$_3$)$_2$ | Et | C$_6$H$_5$ | 0 |
| 54    | CH(CH$_3$)$_2$ | H  | C$_6$H$_5$ | 0 |
| 55    | CH(CH$_3$)$_2$ | Et | CH$_2$C$_6$H$_5$ | 0 |
| 56    | CH(CH$_3$)$_2$ | H  | CH$_2$C$_6$H$_5$ | 0 |

TABLE 5c

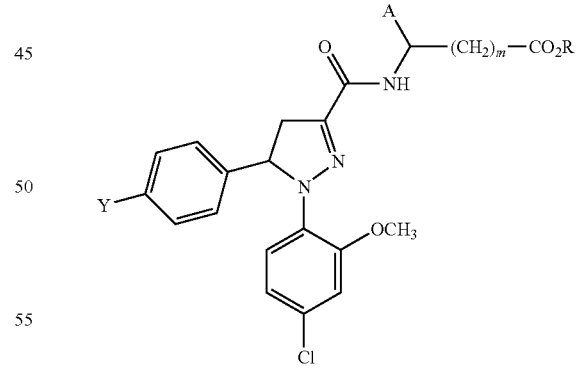

| Ex. # | Y  | R  | A             | m |
|-------|----|----|---------------|---|
| 1     | Cl | Et | H             | 0 |
| 2     | Cl | H  | H             | 0 |
| 3     | Cl | Et | H             | 1 |
| 4     | Cl | H  | H             | 1 |
| 5     | Cl | Et | H             | 3 |
| 6     | Cl | H  | H             | 3 |
| 7     | Cl | Et | C(CH$_3$)$_3$ | 0 |
| 8     | Cl | H  | C(CH$_3$)$_3$ | 0 |
| 9     | Cl | Et | C(CH$_3$)$_3$ | 2 |

TABLE 5c-continued

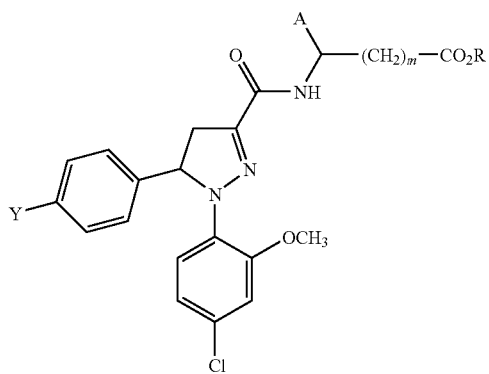

| Ex. # | Y | R | A | m |
|---|---|---|---|---|
| 10 | Cl | H | C(CH$_3$)$_3$ | 2 |
| 11 | Cl | Et | C$_6$H$_5$ | 0 |
| 12 | Cl | H | C$_6$H$_5$ | 0 |
| 13 | Cl | Et | CH$_2$C$_6$H$_5$ | 0 |
| 14 | Cl | H | CH$_2$C$_6$H$_5$ | 0 |
| 15 | CH$_3$ | Et | H | 0 |
| 16 | CH$_3$ | H | H | 0 |
| 17 | CH$_3$ | Et | H | 1 |
| 18 | CH$_3$ | H | H | 1 |
| 19 | CH$_3$ | Et | H | 3 |
| 20 | CH$_3$ | H | H | 3 |
| 21 | CH$_3$ | Et | C(CH$_3$)$_3$ | 0 |
| 22 | CH$_3$ | H | C(CH$_3$)$_3$ | 0 |
| 23 | CH$_3$ | Et | C(CH$_3$)$_3$ | 2 |
| 24 | CH$_3$ | H | C(CH$_3$)$_3$ | 2 |
| 25 | CH$_3$ | Et | C$_6$H$_5$ | 0 |
| 26 | CH$_3$ | H | C$_6$H$_5$ | 0 |
| 27 | CH$_3$ | Et | CH$_2$C$_6$H$_5$ | 0 |
| 28 | CH$_3$ | H | CH$_2$C$_6$H$_5$ | 0 |
| 29 | OCH$_3$ | Et | H | 0 |
| 30 | OCH$_3$ | H | H | 0 |
| 31 | OCH$_3$ | Et | H | 1 |
| 32 | OCH$_3$ | H | H | 1 |
| 33 | OCH$_3$ | Et | H | 3 |
| 34 | OCH$_3$ | H | H | 3 |
| 35 | OCH$_3$ | Et | C(CH$_3$)$_3$ | 0 |
| 36 | OCH$_3$ | H | C(CH$_3$)$_3$ | 0 |
| 37 | OCH$_3$ | Et | C(CH$_3$)$_3$ | 2 |
| 38 | OCH$_3$ | H | C(CH$_3$)$_3$ | 2 |
| 39 | OCH$_3$ | Et | C$_6$H$_5$ | 0 |
| 40 | OCH$_3$ | H | C$_6$H$_5$ | 0 |
| 41 | OCH$_3$ | Et | CH$_2$C$_6$H$_5$ | 0 |
| 42 | OCH$_3$ | H | CH$_2$C$_6$H$_5$ | 0 |
| 43 | CH(CH$_3$)$_2$ | Et | H | 0 |
| 44 | CH(CH$_3$)$_2$ | H | H | 0 |
| 45 | CH(CH$_3$)$_2$ | Et | H | 1 |
| 46 | CH(CH$_3$)$_2$ | H | H | 1 |
| 47 | CH(CH$_3$)$_2$ | Et | H | 3 |
| 48 | CH(CH$_3$)$_2$ | H | H | 3 |
| 49 | CH(CH$_3$)$_2$ | Et | C(CH$_3$)$_3$ | 0 |
| 50 | CH(CH$_3$)$_2$ | H | C(CH$_3$)$_3$ | 0 |
| 51 | CH(CH$_3$)$_2$ | Et | C(CH$_3$)$_3$ | 2 |
| 52 | CH(CH$_3$)$_2$ | H | C(CH$_3$)$_3$ | 2 |
| 53 | CH(CH$_3$)$_2$ | Et | C$_6$H$_5$ | 0 |
| 54 | CH(CH$_3$)$_2$ | H | C$_6$H$_5$ | 0 |
| 55 | CH(CH$_3$)$_2$ | Et | CH$_2$C$_6$H$_5$ | 0 |
| 56 | CH(CH$_3$)$_2$ | H | CH$_2$C$_6$H$_5$ | 0 |

TABLE 5d

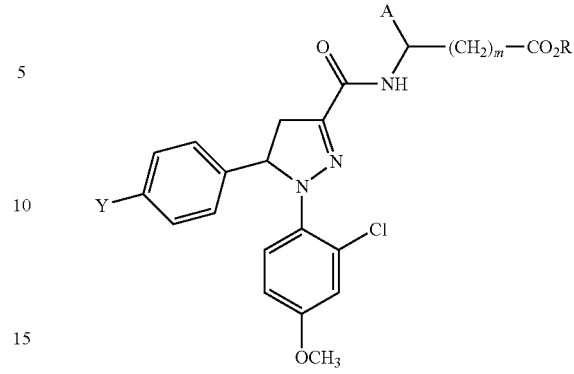

| Ex. # | Y | R | A | m |
|---|---|---|---|---|
| 1 | Cl | Et | H | 0 |
| 2 | Cl | H | H | 0 |
| 3 | Cl | Et | H | 1 |
| 4 | Cl | H | H | 1 |
| 5 | Cl | Et | H | 3 |
| 6 | Cl | H | H | 3 |
| 7 | Cl | Et | CH$_3$ | 0 |
| 8 | Cl | H | CH$_3$ | 0 |
| 9 | Cl | Et | CH$_3$ | 2 |
| 10 | Cl | H | CH$_3$ | 2 |
| 11 | Cl | Et | C$_6$H$_5$ | 0 |
| 12 | Cl | H | C$_6$H$_5$ | 0 |
| 13 | Cl | Et | CH$_2$C$_6$H$_5$ | 0 |
| 14 | Cl | H | CH$_2$C$_6$H$_5$ | 0 |
| 15 | CH$_3$ | Et | H | 0 |
| 16 | CH$_3$ | H | H | 0 |
| 17 | CH$_3$ | Et | H | 1 |
| 18 | CH$_3$ | H | H | 1 |
| 19 | CH$_3$ | Et | H | 3 |
| 20 | CH$_3$ | H | H | 3 |
| 21 | CH$_3$ | Et | C(CH$_3$)$_3$ | 0 |
| 22 | CH$_3$ | H | C(CH$_3$)$_3$ | 0 |
| 23 | CH$_3$ | Et | C(CH$_3$)$_3$ | 2 |
| 24 | CH$_3$ | H | C(CH$_3$)$_3$ | 2 |
| 25 | CH$_3$ | Et | C$_6$H$_5$ | 0 |
| 26 | CH$_3$ | H | C$_6$H$_5$ | 0 |
| 27 | CH$_3$ | Et | CH$_2$C$_6$H$_5$ | 0 |
| 28 | CH$_3$ | H | CH$_2$C$_6$H$_5$ | 0 |
| 29 | OCH$_3$ | Et | H | 0 |
| 30 | OCH$_3$ | H | H | 0 |
| 31 | OCH$_3$ | Et | H | 1 |
| 32 | OCH$_3$ | H | H | 1 |
| 33 | OCH$_3$ | Et | H | 3 |
| 34 | OCH$_3$ | H | H | 3 |
| 35 | OCH$_3$ | Et | C(CH$_3$)$_3$ | 0 |
| 36 | OCH$_3$ | H | C(CH$_3$)$_3$ | 0 |
| 37 | OCH$_3$ | Et | C(CH$_3$)$_3$ | 2 |
| 38 | OCH$_3$ | H | C(CH$_3$)$_3$ | 2 |
| 39 | OCH$_3$ | Et | C$_6$H$_5$ | 0 |
| 40 | OCH$_3$ | H | C$_6$H$_5$ | 0 |
| 41 | OCH$_3$ | Et | CH$_2$C$_6$H$_5$ | 0 |
| 42 | OCH$_3$ | H | CH$_2$C$_6$H$_5$ | 0 |
| 43 | CH(CH$_3$)$_2$ | Et | H | 0 |
| 44 | CH(CH$_3$)$_2$ | H | H | 0 |
| 45 | CH(CH$_3$)$_2$ | Et | H | 1 |
| 46 | CH(CH$_3$)$_2$ | H | H | 1 |
| 47 | CH(CH$_3$)$_2$ | Et | H | 3 |
| 48 | CH(CH$_3$)$_2$ | H | H | 3 |
| 49 | CH(CH$_3$)$_2$ | Et | C(CH$_3$)$_3$ | 0 |
| 50 | CH(CH$_3$)$_2$ | H | C(CH$_3$)$_3$ | 0 |
| 51 | CH(CH$_3$)$_2$ | Et | C(CH$_3$)$_3$ | 2 |
| 52 | CH(CH$_3$)$_2$ | H | C(CH$_3$)$_3$ | 2 |
| 53 | CH(CH$_3$)$_2$ | Et | C$_6$H$_5$ | 0 |
| 54 | CH(CH$_3$)$_2$ | H | C$_6$H$_5$ | 0 |
| 55 | CH(CH$_3$)$_2$ | Et | CH$_2$C$_6$H$_5$ | 0 |
| 56 | CH(CH$_3$)$_2$ | H | CH$_2$C$_6$H$_5$ | 0 |

TABLE 5e

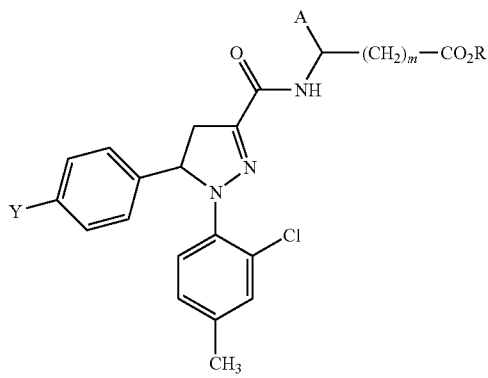

| Ex. # | Y | R | A | m |
|---|---|---|---|---|
| 1 | Cl | Et | H | 0 |
| 2 | Cl | H | H | 0 |
| 3 | Cl | Et | H | 1 |
| 4 | Cl | H | H | 1 |
| 5 | Cl | Et | H | 3 |
| 6 | Cl | H | H | 3 |
| 7 | Cl | Et | CH$_3$ | 0 |
| 8 | Cl | H | CH$_3$ | 0 |
| 9 | Cl | Et | CH$_3$ | 2 |
| 10 | Cl | H | CH$_3$ | 2 |
| 11 | Cl | Et | C$_6$H$_5$ | 0 |
| 12 | Cl | H | C$_6$H$_5$ | 0 |
| 13 | Cl | Et | CH$_2$C$_6$H$_5$ | 0 |
| 14 | Cl | H | CH$_2$C$_6$H$_5$ | 0 |
| 15 | CH$_3$ | Et | H | 0 |
| 16 | CH$_3$ | H | H | 0 |
| 17 | CH$_3$ | Et | H | 1 |
| 18 | CH$_3$ | H | H | 1 |
| 19 | CH$_3$ | Et | H | 3 |
| 20 | CH$_3$ | H | H | 3 |
| 21 | CH$_3$ | Et | CH$_3$ | 0 |
| 22 | CH$_3$ | H | CH$_3$ | 0 |
| 23 | CH$_3$ | Et | CH$_3$ | 2 |
| 24 | CH$_3$ | H | CH$_3$ | 2 |
| 25 | CH$_3$ | Et | C$_6$H$_5$ | 0 |
| 26 | CH$_3$ | H | C$_6$H$_5$ | 0 |
| 27 | CH$_3$ | Et | CH$_2$C$_6$H$_5$ | 0 |
| 28 | CH$_3$ | H | CH$_2$C$_6$H$_5$ | 0 |
| 29 | OCH$_3$ | Et | H | 0 |
| 30 | OCH$_3$ | H | H | 0 |
| 31 | OCH$_3$ | Et | H | 1 |
| 32 | OCH$_3$ | H | H | 1 |
| 33 | OCH$_3$ | Et | H | 3 |
| 34 | OCH$_3$ | H | H | 3 |
| 35 | OCH$_3$ | Et | CH$_3$ | 0 |
| 36 | OCH$_3$ | H | CH$_3$ | 0 |
| 37 | OCH$_3$ | Et | CH$_3$ | 2 |
| 38 | OCH$_3$ | H | CH$_3$ | 2 |
| 39 | OCH$_3$ | Et | C$_6$H$_5$ | 0 |
| 40 | OCH$_3$ | H | C$_6$H$_5$ | 0 |
| 41 | OCH$_3$ | Et | CH$_2$C$_6$H$_5$ | 0 |
| 42 | OCH$_3$ | H | CH$_2$C$_6$H$_5$ | 0 |
| 43 | CH(CH$_3$)$_2$ | Et | H | 0 |
| 44 | CH(CH$_3$)$_2$ | H | H | 0 |
| 45 | CH(CH$_3$)$_2$ | Et | H | 1 |
| 46 | CH(CH$_3$)$_2$ | H | H | 1 |
| 47 | CH(CH$_3$)$_2$ | Et | H | 3 |
| 48 | CH(CH$_3$)$_2$ | H | H | 3 |
| 49 | CH(CH$_3$)$_2$ | Et | CH$_3$ | 0 |
| 50 | CH(CH$_3$)$_2$ | H | CH$_3$ | 0 |
| 51 | CH(CH$_3$)$_2$ | Et | CH$_3$ | 2 |
| 52 | CH(CH$_3$)$_2$ | H | CH$_3$ | 2 |
| 53 | CH(CH$_3$)$_2$ | Et | C$_6$H$_5$ | 0 |
| 54 | CH(CH$_3$)$_2$ | H | C$_6$H$_5$ | 0 |
| 55 | CH(CH$_3$)$_2$ | Et | CH$_2$C$_6$H$_5$ | 0 |
| 56 | CH(CH$_3$)$_2$ | H | CH$_2$C$_6$H$_5$ | 0 |

TABLE 5f

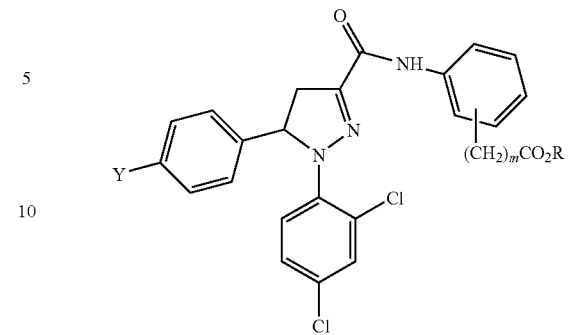

| Ex. # | Y | R | Substituent position | m |
|---|---|---|---|---|
| 1 | Cl | Et | 2 | 0 |
| 2 | Cl | H | 2 | 0 |
| 3 | Cl | Et | 2 | 0 |
| 4 | Cl | H | 2 | 0 |
| 5 | Cl | Et | 2 | 1 |
| 6 | Cl | H | 2 | 1 |
| 7 | Cl | Et | 2 | 1 |
| 8 | Cl | H | 2 | 1 |
| 9 | CH$_3$ | Et | 2 | 0 |
| 10 | CH$_3$ | H | 2 | 0 |
| 11 | CH$_3$ | Et | 2 | 0 |
| 12 | CH$_3$ | H | 2 | 0 |
| 13 | CH$_3$ | Et | 2 | 1 |
| 14 | CH$_3$ | H | 2 | 1 |
| 15 | CH$_3$ | Et | 2 | 1 |
| 16 | CH$_3$ | H | 2 | 1 |
| 17 | OCH$_3$ | Et | 2 | 0 |
| 18 | OCH$_3$ | H | 2 | 0 |
| 19 | OCH$_3$ | Et | 2 | 0 |
| 20 | OCH$_3$ | H | 2 | 0 |
| 21 | OCH$_3$ | Et | 2 | 1 |
| 22 | OCH$_3$ | H | 2 | 1 |
| 23 | OCH$_3$ | Et | 2 | 1 |
| 24 | OCH$_3$ | H | 2 | 1 |
| 25 | CH(CH$_3$)$_2$ | Et | 2 | 0 |
| 26 | CH(CH$_3$)$_2$ | H | 2 | 0 |
| 27 | CH(CH$_3$)$_2$ | Et | 2 | 0 |
| 28 | CH(CH$_3$)$_2$ | H | 2 | 0 |
| 29 | CH(CH$_3$)$_2$ | Et | 2 | 1 |
| 30 | CH(CH$_3$)$_2$ | H | 2 | 1 |
| 31 | CH(CH$_3$)$_2$ | Et | 2 | 1 |
| 32 | CH(CH$_3$)$_2$ | H | 2 | 1 |
| 33 | Cl | Et | 3 | 0 |
| 34 | Cl | H | 3 | 0 |
| 35 | Cl | Et | 3 | 0 |
| 36 | Cl | H | 3 | 0 |
| 37 | Cl | Et | 3 | 1 |
| 38 | Cl | H | 3 | 1 |
| 39 | Cl | Et | 3 | 1 |
| 40 | Cl | H | 3 | 1 |
| 41 | CH$_3$ | Et | 3 | 0 |
| 42 | CH$_3$ | H | 3 | 0 |
| 43 | CH$_3$ | Et | 3 | 0 |
| 44 | CH$_3$ | H | 3 | 0 |
| 45 | CH$_3$ | Et | 3 | 1 |
| 46 | CH$_3$ | H | 3 | 1 |
| 47 | CH$_3$ | Et | 3 | 1 |
| 48 | CH$_3$ | H | 3 | 1 |
| 49 | OCH$_3$ | Et | 3 | 0 |
| 50 | OCH$_3$ | H | 3 | 0 |
| 51 | OCH$_3$ | Et | 3 | 0 |
| 52 | OCH$_3$ | H | 3 | 0 |
| 53 | OCH$_3$ | Et | 3 | 1 |
| 54 | OCH$_3$ | H | 3 | 1 |
| 55 | OCH$_3$ | Et | 3 | 1 |
| 56 | OCH$_3$ | H | 3 | 1 |
| 57 | CH(CH$_3$)$_2$ | Et | 3 | 0 |
| 58 | CH(CH$_3$)$_2$ | H | 3 | 0 |
| 59 | CH(CH$_3$)$_2$ | Et | 3 | 0 |
| 60 | CH(CH$_3$)$_2$ | H | 3 | 0 |

TABLE 5f-continued

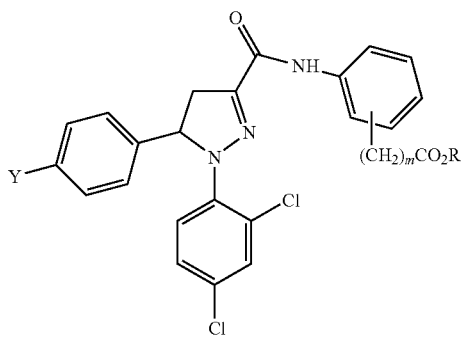

| Ex. # | Y | R | Substituent position | m |
|---|---|---|---|---|
| 61 | CH(CH$_3$)$_2$ | Et | 3 | 1 |
| 62 | CH(CH$_3$)$_2$ | H | 3 | 1 |
| 63 | CH(CH$_3$)$_2$ | Et | 3 | 1 |
| 64 | CH(CH$_3$)$_2$ | H | 3 | 1 |
| 65 | Cl | Et | 4 | 0 |
| 66 | Cl | H | 4 | 0 |
| 67 | Cl | Et | 4 | 0 |
| 68 | Cl | H | 4 | 0 |
| 69 | Cl | Et | 4 | 1 |
| 70 | Cl | H | 4 | 1 |
| 71 | Cl | Et | 4 | 1 |
| 72 | Cl | H | 4 | 1 |
| 73 | CH$_3$ | Et | 4 | 0 |
| 74 | CH$_3$ | H | 4 | 0 |
| 75 | CH$_3$ | Et | 4 | 0 |
| 76 | CH$_3$ | H | 4 | 0 |
| 77 | CH$_3$ | Et | 4 | 1 |
| 78 | CH$_3$ | H | 4 | 1 |
| 79 | CH$_3$ | Et | 4 | 1 |
| 80 | CH$_3$ | H | 4 | 1 |
| 81 | OCH$_3$ | Et | 4 | 0 |
| 82 | OCH$_3$ | H | 4 | 0 |
| 83 | OCH$_3$ | Et | 4 | 0 |
| 84 | OCH$_3$ | H | 4 | 0 |
| 85 | OCH$_3$ | Et | 4 | 1 |
| 86 | OCH$_3$ | H | 4 | 1 |
| 87 | OCH$_3$ | Et | 4 | 1 |
| 88 | OCH$_3$ | H | 4 | 1 |
| 89 | CH(CH$_3$)$_2$ | Et | 4 | 0 |
| 90 | CH(CH$_3$)$_2$ | H | 4 | 0 |
| 91 | CH(CH$_3$)$_2$ | Et | 4 | 0 |
| 92 | CH(CH$_3$)$_2$ | H | 4 | 0 |
| 93 | CH(CH$_3$)$_2$ | Et | 4 | 1 |
| 94 | CH(CH$_3$)$_2$ | H | 4 | 1 |
| 95 | CH(CH$_3$)$_2$ | Et | 4 | 1 |
| 96 | CH(CH$_3$)$_2$ | H | 4 | 1 |

TABLE 5g

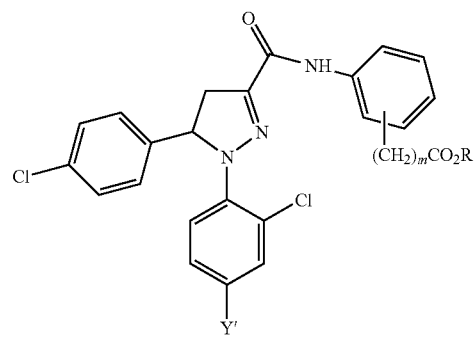

| Ex. # | Y' | R | Substituent position | m |
|---|---|---|---|---|
| 1 | CH$_3$ | Et | 2 | 0 |
| 2 | CH$_3$ | H | 2 | 0 |
| 3 | CH$_3$ | Et | 2 | 0 |
| 4 | CH$_3$ | H | 2 | 0 |
| 5 | CH$_3$ | Et | 2 | 1 |
| 6 | CH$_3$ | H | 2 | 1 |
| 7 | CH$_3$ | Et | 2 | 1 |
| 8 | CH$_3$ | H | 2 | 1 |
| 9 | OCH$_3$ | Et | 2 | 0 |
| 10 | OCH$_3$ | H | 2 | 0 |
| 11 | OCH$_3$ | Et | 2 | 0 |
| 12 | OCH$_3$ | H | 2 | 0 |
| 13 | OCH$_3$ | Et | 2 | 1 |
| 14 | OCH$_3$ | H | 2 | 1 |
| 15 | OCH$_3$ | Et | 2 | 1 |
| 16 | OCH$_3$ | H | 2 | 1 |
| 17 | CH(CH$_3$)$_2$ | Et | 2 | 0 |
| 18 | CH(CH$_3$)$_2$ | H | 2 | 0 |
| 19 | CH(CH$_3$)$_2$ | Et | 2 | 0 |
| 20 | CH(CH$_3$)$_2$ | H | 2 | 0 |
| 21 | CH(CH$_3$)$_2$ | Et | 2 | 1 |
| 22 | CH(CH$_3$)$_2$ | H | 2 | 1 |
| 23 | CH(CH$_3$)$_2$ | Et | 2 | 1 |
| 24 | CH(CH$_3$)$_2$ | H | 2 | 1 |
| 25 | CH$_3$ | Et | 3 | 0 |
| 26 | CH$_3$ | H | 3 | 0 |
| 27 | CH$_3$ | Et | 3 | 0 |
| 28 | CH$_3$ | H | 3 | 0 |
| 29 | CH$_3$ | Et | 3 | 1 |
| 30 | CH$_3$ | H | 3 | 1 |
| 31 | CH$_3$ | Et | 3 | 1 |
| 32 | CH$_3$ | H | 3 | 1 |
| 33 | OCH$_3$ | Et | 3 | 0 |
| 34 | OCH$_3$ | H | 3 | 0 |
| 35 | OCH$_3$ | Et | 3 | 0 |
| 36 | OCH$_3$ | H | 3 | 0 |
| 37 | OCH$_3$ | Et | 3 | 1 |
| 38 | OCH$_3$ | H | 3 | 1 |
| 39 | OCH$_3$ | Et | 3 | 1 |
| 40 | OCH$_3$ | H | 3 | 1 |
| 41 | CH(CH$_3$)$_2$ | Et | 3 | 0 |
| 42 | CH(CH$_3$)$_2$ | H | 3 | 0 |
| 43 | CH(CH$_3$)$_2$ | Et | 3 | 0 |
| 44 | CH(CH$_3$)$_2$ | H | 3 | 0 |
| 45 | CH(CH$_3$)$_2$ | Et | 3 | 1 |
| 46 | CH(CH$_3$)$_2$ | H | 3 | 1 |
| 47 | CH(CH$_3$)$_2$ | Et | 3 | 1 |
| 48 | CH(CH$_3$)$_2$ | H | 3 | 1 |
| 49 | CH$_3$ | Et | 4 | 0 |
| 50 | CH$_3$ | H | 4 | 0 |
| 51 | CH$_3$ | Et | 4 | 0 |
| 52 | CH$_3$ | H | 4 | 0 |
| 53 | CH$_3$ | Et | 4 | 1 |
| 54 | CH$_3$ | H | 4 | 1 |
| 55 | CH$_3$ | Et | 4 | 1 |
| 56 | CH$_3$ | H | 4 | 1 |
| 57 | OCH$_3$ | Et | 4 | 0 |
| 58 | OCH$_3$ | H | 4 | 0 |
| 59 | OCH$_3$ | Et | 4 | 0 |
| 60 | OCH$_3$ | H | 4 | 0 |

TABLE 5g-continued

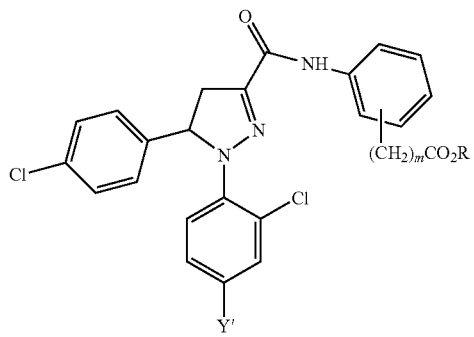

| Ex. # | Y' | R | Substituent position | m |
|---|---|---|---|---|
| 61 | OCH₃ | Et | 4 | 1 |
| 62 | OCH₃ | H | 4 | 1 |
| 63 | OCH₃ | Et | 4 | 1 |
| 64 | OCH₃ | H | 4 | 1 |
| 65 | CH(CH₃)₂ | Et | 4 | 0 |
| 66 | CH(CH₃)₂ | H | 4 | 0 |
| 67 | CH(CH₃)₂ | Et | 4 | 0 |
| 68 | CH(CH₃)₂ | H | 4 | 0 |
| 69 | CH(CH₃)₂ | Et | 4 | 1 |
| 70 | CH(CH₃)₂ | H | 4 | 1 |
| 71 | CH(CH₃)₂ | Et | 4 | 1 |
| 72 | CH(CH₃)₂ | H | 4 | 1 |

TABLE 6a

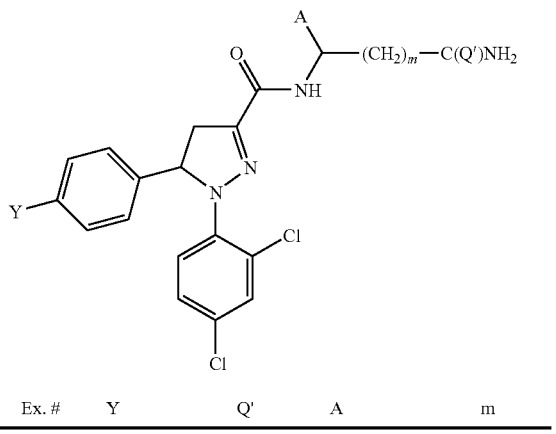

| Ex. # | Y | Q' | A | m |
|---|---|---|---|---|
| 1 | Cl | O | H | 0 |
| 2 | Cl | NH | H | 0 |
| 3 | Cl | O | H | 1 |
| 4 | Cl | NH | H | 1 |
| 5 | Cl | O | H | 3 |
| 6 | Cl | NH | H | 3 |
| 7 | Cl | O | CH₃ | 0 |
| 8 | Cl | NH | CH₃ | 0 |
| 9 | Cl | O | CH₃ | 2 |
| 10 | Cl | NH | CH₃ | 2 |
| 11 | Cl | O | C₆H₅ | 0 |
| 12 | Cl | NH | C₆H₅ | 0 |
| 13 | Cl | O | CH₂C₆H₅ | 0 |
| 14 | Cl | NH | CH₂C₆H₅ | 0 |
| 15 | CH₃ | O | H | 0 |
| 16 | CH₃ | NH | H | 0 |
| 17 | CH₃ | O | H | 1 |
| 18 | CH₃ | NH | H | 1 |
| 19 | CH₃ | O | H | 3 |
| 20 | CH₃ | NH | H | 3 |
| 21 | CH₃ | O | CH₃ | 0 |
| 22 | CH₃ | NH | CH₃ | 0 |

TABLE 6a-continued

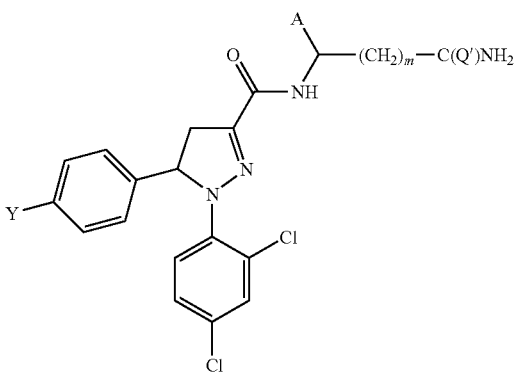

| Ex. # | Y | Q' | A | m |
|---|---|---|---|---|
| 23 | CH₃ | O | CH₃ | 2 |
| 24 | CH₃ | NH | CH₃ | 2 |
| 25 | CH₃ | O | C₆H₅ | 0 |
| 26 | CH₃ | NH | C₆H₅ | 0 |
| 27 | CH₃ | O | CH₂C₆H₅ | 0 |
| 28 | CH₃ | NH | CH₂C₆H₅ | 0 |
| 29 | OCH₃ | O | H | 0 |
| 30 | OCH₃ | NH | H | 0 |
| 31 | OCH₃ | O | H | 1 |
| 32 | OCH₃ | NH | H | 1 |
| 33 | OCH₃ | O | H | 3 |
| 34 | OCH₃ | NH | H | 3 |
| 35 | OCH₃ | O | CH₃ | 0 |
| 36 | OCH₃ | NH | CH₃ | 0 |
| 37 | OCH₃ | O | CH₃ | 2 |
| 38 | OCH₃ | NH | CH₃ | 2 |
| 39 | OCH₃ | O | C₆H₅ | 0 |
| 40 | OCH₃ | NH | C₆H₅ | 0 |
| 41 | OCH₃ | O | CH₂C₆H₅ | 0 |
| 42 | OCH₃ | NH | CH₂C₆H₅ | 0 |
| 43 | CH(CH₃)₂ | O | H | 0 |
| 44 | CH(CH₃)₂ | NH | H | 0 |
| 45 | CH(CH₃)₂ | O | H | 1 |
| 46 | CH(CH₃)₂ | NH | H | 1 |
| 47 | CH(CH₃)₂ | O | H | 3 |
| 48 | CH(CH₃)₂ | NH | H | 3 |
| 49 | CH(CH₃)₂ | O | CH₃ | 0 |
| 50 | CH(CH₃)₂ | NH | CH₃ | 0 |
| 51 | CH(CH₃)₂ | O | CH₃ | 2 |
| 52 | CH(CH₃)₂ | NH | CH₃ | 2 |
| 53 | CH(CH₃)₂ | O | C₆H₅ | 0 |
| 54 | CH(CH₃)₂ | NH | C₆H₅ | 0 |
| 55 | CH(CH₃)₂ | O | CH₂C₆H₅ | 0 |
| 56 | CH(CH₃)₂ | NH | CH₂C₆H₅ | 0 |
| 57 | Cl | O | C(CH₃)₃ | 0 |
| 58 | Cl | NH | C(CH₃)₃ | 0 |
| 59 | Cl | O | C(CH₃)₃ | 1 |
| 60 | Cl | NH | C(CH₃)₃ | 1 |
| 61 | Cl | O | C(CH₃)₃ | 2 |
| 62 | Cl | NH | C(CH₃)₃ | 2 |

TABLE 6b

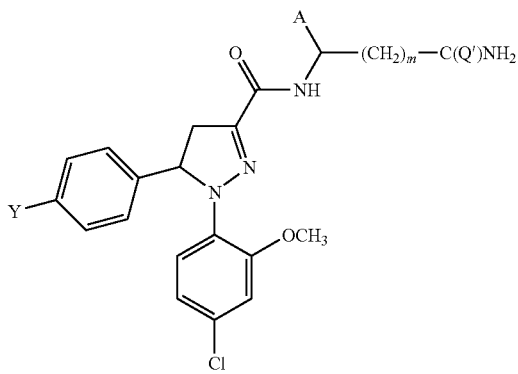

| Ex. # | Y | Q' | A | m |
|---|---|---|---|---|
| 1 | Cl | O | H | 0 |
| 2 | Cl | NH | H | 0 |
| 3 | Cl | O | H | 1 |
| 4 | Cl | NH | H | 1 |
| 5 | Cl | O | H | 3 |
| 6 | Cl | NH | H | 3 |
| 7 | Cl | O | $C(CH_3)_3$ | 0 |
| 8 | Cl | NH | $C(CH_3)_3$ | 0 |
| 9 | Cl | O | $C(CH_3)_3$ | 2 |
| 10 | Cl | NH | $C(CH_3)_3$ | 2 |
| 11 | Cl | O | $C_6H_5$ | 0 |
| 12 | Cl | NH | $C_6H_5$ | 0 |
| 13 | Cl | O | $CH_2C_6H_5$ | 0 |
| 14 | Cl | NH | $CH_2C_6H_5$ | 0 |
| 15 | $CH_3$ | O | H | 0 |
| 16 | $CH_3$ | NH | H | 0 |
| 17 | $CH_3$ | O | H | 1 |
| 18 | $CH_3$ | NH | H | 1 |
| 19 | $CH_3$ | O | H | 3 |
| 20 | $CH_3$ | NH | H | 3 |
| 21 | $CH_3$ | O | $C(CH_3)_3$ | 0 |
| 22 | $CH_3$ | NH | $C(CH_3)_3$ | 0 |
| 23 | $CH_3$ | O | $C(CH_3)_3$ | 2 |
| 24 | $CH_3$ | NH | $C(CH_3)_3$ | 2 |
| 25 | $CH_3$ | O | $C_6H_5$ | 0 |
| 26 | $CH_3$ | NH | $C_6H_5$ | 0 |
| 27 | $CH_3$ | O | $CH_2C_6H_5$ | 0 |
| 28 | $CH_3$ | NH | $CH_2C_6H_5$ | 0 |
| 29 | $OCH_3$ | O | H | 0 |
| 30 | $OCH_3$ | NH | H | 0 |
| 31 | $OCH_3$ | O | H | 1 |
| 32 | $OCH_3$ | NH | H | 1 |
| 33 | $OCH_3$ | O | H | 3 |
| 34 | $OCH_3$ | NH | H | 3 |
| 35 | $OCH_3$ | O | $C(CH_3)_3$ | 0 |
| 36 | $OCH_3$ | NH | $C(CH_3)_3$ | 0 |
| 37 | $OCH_3$ | O | $C(CH_3)_3$ | 2 |
| 38 | $OCH_3$ | NH | $C(CH_3)_3$ | 2 |
| 39 | $OCH_3$ | O | $C_6H_5$ | 0 |
| 40 | $OCH_3$ | NH | $C_6H_5$ | 0 |
| 41 | $OCH_3$ | O | $CH_2C_6H_5$ | 0 |
| 42 | $OCH_3$ | NH | $CH_2C_6H_5$ | 0 |
| 43 | $CH(CH_3)_2$ | O | H | 0 |
| 44 | $CH(CH_3)_2$ | NH | H | 0 |
| 45 | $CH(CH_3)_2$ | O | H | 1 |
| 46 | $CH(CH_3)_2$ | NH | H | 1 |
| 47 | $CH(CH_3)_2$ | O | H | 3 |
| 48 | $CH(CH_3)_2$ | NH | H | 3 |
| 49 | $CH(CH_3)_2$ | O | $C(CH_3)_3$ | 0 |
| 50 | $CH(CH_3)_2$ | NH | $C(CH_3)_3$ | 0 |
| 51 | $CH(CH_3)_2$ | O | $C(CH_3)_3$ | 2 |
| 52 | $CH(CH_3)_2$ | NH | $C(CH_3)_3$ | 2 |
| 53 | $CH(CH_3)_2$ | O | $C_6H_5$ | 0 |
| 54 | $CH(CH_3)_2$ | NH | $C_6H_5$ | 0 |
| 55 | $CH(CH_3)_2$ | O | $CH_2C_6H_5$ | 0 |
| 56 | $CH(CH_3)_2$ | NH | $CH_2C_6H_5$ | 0 |

TABLE 6c

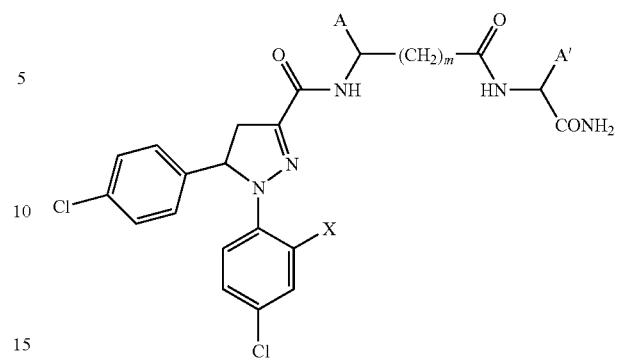

| Ex. # | X | A' | A | m |
|---|---|---|---|---|
| 1 | Cl | $CH_3$ | H | 0 |
| 2 | Cl | $CH_3$ | H | 1 |
| 3 | Cl | $CH_3$ | H | 3 |
| 4 | Cl | $CH_2C_6H_5$ | H | 0 |
| 5 | Cl | $CH_2C_6H_5$ | H | 1 |
| 6 | Cl | $CH_2C_6H_5$ | H | 3 |
| 7 | Cl | $C_6H_5$ | H | 0 |
| 8 | Cl | $C_6H_5$ | H | 1 |
| 9 | Cl | $C_6H_5$ | H | 3 |
| 10 | Cl | $CH(CH_3)_2$ | H | 0 |
| 11 | Cl | $CH(CH_3)_2$ | H | 1 |
| 12 | Cl | $CH(CH_3)_2$ | H | 3 |
| 13 | Cl | $CH_3$ | $CH_3$ | 0 |
| 14 | Cl | $CH_2C_6H_5$ | $CH_3$ | 0 |
| 15 | Cl | $C_6H_5$ | $CH_3$ | 0 |
| 16 | Cl | $CH(CH_3)_2$ | $CH_3$ | 0 |
| 17 | Cl | $CH_3$ | $CH_2C_6H_5$ | 0 |
| 18 | Cl | $CH_2C_6H_5$ | $CH_2C_6H_5$ | 0 |
| 19 | Cl | $C_6H_5$ | $CH_2C_6H_5$ | 0 |
| 20 | Cl | $CH(CH_3)_2$ | $CH_2C_6H_5$ | 0 |
| 21 | Cl | $CH_3$ | $CH_2OH$ | 0 |
| 22 | Cl | $CH_2C_6H_5$ | $CH_2OH$ | 0 |
| 23 | Cl | $C_6H_5$ | $CH_2OH$ | 0 |
| 24 | Cl | $CH(CH_3)_2$ | $CH_2OH$ | 0 |
| 25 | OMe | $CH_3$ | H | 0 |
| 26 | OMe | $CH_3$ | H | 1 |
| 27 | OMe | $CH_3$ | H | 3 |
| 28 | OMe | $CH_2C_6H_5$ | H | 0 |
| 29 | OMe | $CH_2C_6H_5$ | H | 1 |
| 30 | OMe | $CH_2C_6H_5$ | H | 3 |
| 31 | OMe | $C_6H_5$ | H | 0 |
| 32 | OMe | $C_6H_5$ | H | 1 |
| 33 | OMe | $C_6H_5$ | H | 3 |
| 34 | OMe | $CH(CH_3)_2$ | H | 0 |
| 35 | OMe | $CH(CH_3)_2$ | H | 1 |
| 36 | OMe | $CH(CH_3)_2$ | H | 3 |
| 37 | OMe | $CH_3$ | $CH_3$ | 0 |
| 38 | OMe | $CH_2C_6H_5$ | $CH_3$ | 0 |
| 39 | OMe | $C_6H_5$ | $CH_3$ | 0 |
| 40 | OMe | $CH(CH_3)_2$ | $CH_3$ | 0 |
| 41 | OMe | $CH_3$ | $CH_2C_6H_5$ | 0 |
| 42 | OMe | $CH_2C_6H_5$ | $CH_2C_6H_5$ | 0 |
| 43 | OMe | $C_6H_5$ | $CH_2C_6H_5$ | 0 |
| 44 | OMe | $CH(CH_3)_2$ | $CH_2C_6H_5$ | 0 |
| 45 | OMe | $CH_3$ | $CH_2OH$ | 0 |
| 46 | OMe | $CH_2C_6H_5$ | $CH_2OH$ | 0 |
| 47 | OMe | $C_6H_5$ | $CH_2OH$ | 0 |
| 48 | OMe | $CH(CH_3)_2$ | $CH_2OH$ | 0 |

Numerous modifications and variations of the present invention are possible in light of the above teachings. It is therefore to be understood that within the scope of the appended claims, the invention may be practiced otherwise that as specifically described herein.

What is claimed is:

1. A compound of formula I or a stereoisomer or pharmaceutically acceptable salt thereof:

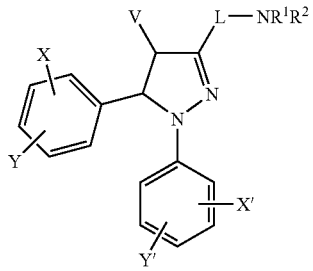

wherein:

L is C(=O) or SO$_2$;

X, X', Y, and Y' are independently selected from H, halogen, C$_{1-6}$ alkyl, NO$_2$, CF$_3$, NR$_2$, OR, —CN, (CH$_2$)$_m$CO$_2$R, O(CH$_2$)$_n$CO$_2$R, OCH$_2$CH=CHCO$_2$R, CH$_2$O(CH$_2$)$_n$CO$_2$R, CH$_2$OCH$_2$CH=CHCO$_2$R, O(CH$_2$)$_n$PO(OR)$_2$, CH$_2$O(CH$_2$)$_n$PO(OR)$_2$, NR$^a$(CH$_2$)$_m$CO$_2$R, NR$^a$(CH$_2$)$_n$PO(OR)$_2$, NR$^a$CH$_2$CH=CHCO$_2$R, NR$^a$SO$_2$CH$_3$, NR$^a$CO(CH$_2$)$_n$CO$_2$R, O(CH$_2$)$_n$C$_6$H$_4$CO$_2$R, O(CH$_2$)$_n$C$_6$H$_4$(CH$_2$)$_n$CO$_2$R, CH$_2$O(CH$_2$)$_n$C$_6$H$_4$CO$_2$R, O(CH$_2$)$_n$C$_6$H$_4$CONR$^c$$_2$, O(CH$_2$)$_n$C$_6$H$_4$(CH$_2$)$_n$CONR$^c$$_2$, O(CH$_2$)$_n$C$_6$H$_4$-tetrazole, CH$_2$O(CH$_2$)$_n$C$_6$H$_4$CONR$^c$$_2$, CH$_2$O(CH$_2$)$_n$C$_6$H$_4$-tetrazole, O(CH$_2$)$_n$C$_6$H$_4$(CH$_2$)$_n$-tetrazole, NR$^a$(CH$_2$)$_n$C$_6$H$_4$CO$_2$R, CH$_2$NR$^a$(CH$_2$)$_n$C$_6$H$_4$CO$_2$R, NR$^a$(CH$_2$)$_n$C$_6$H$_4$CONR$^c$$_2$, CH$_2$NR$^a$(CH$_2$)$_n$C$_6$H$_4$CONR$^c$$_2$, CH$_2$NR$^a$(CH$_2$)$_n$C$_6$H$_4$-tetrazole, (CH$_2$)$_m$C(=NH)NH$_2$, (CH$_2$)$_m$NHC(=NH)NH$_2$, (CH$_2$)$_m$NHC(=CHNO$_2$)NH$_2$, (CH$_2$)$_m$NHC(=NCN)NH$_2$, CONR$^c$$_2$, (CH$_2$)$_n$CONR$^c$$_2$, NR$^c$CONR$^c$$_2$, NR$^c$CO$_2$R, O(CH$_2$)$_n$CONR$^c$$_2$, CH$_2$O(CH$_2$)$_n$CONR$^c$$_2$, NR$^a$(CH$_2$)$_m$CONHR$^a$, OCH$_2$CH=CHCONR$^c$$_2$, CH$_2$OCH$_2$CH=CHCONR$^c$$_2$, NR$^a$CH$_2$CH=CHCONR$^c$$_2$, tetrazole, O(CH$_2$CH$_2$O)$_p$R, NR$^a$(CH$_2$CH$_2$O)$_p$R, SONH$_2$, SO$_2$NR$^a$CH$_3$, CH$_2$N$^+$R$^b$$_3$V$^1$, O(CH$_2$)$_n$-aryl, NR(CH$_2$)$_n$-aryl, O(CH$_2$)$_n$-5-12 membered heteroaryl consisting of carbon atoms and from 1-4 heteroatoms selected from N, O, and S, NR(CH$_2$)$_n$-5-12 membered heteroaryl consisting of carbon atoms and from 1-4 heteroatoms selected from N, O, and S, and

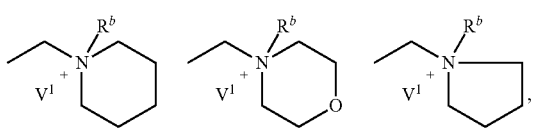

wherein the aryl and heteroaryl groups are independently substituted with 0-2 groups selected from OH, OC$_{1-4}$ alkyl, OC$_{2-4}$ alkenyl, OC$_{2-4}$ alkynyl, halogen, nitro, N(R)$_2$, NRSO$_2$CH$_3$, SO$_2$NRCH$_3$, (CH$_2$)$_r$CO$_2$R$^3$, (CH$_2$)$_r$SO$_3$H, (CH$_2$)$_r$PO$_3$H$_2$, (CH$_2$)$_r$PO$_3$RH, O(CH$_2$)$_r$CO$_2$R$^3$, O(CH$_2$)$_r$SO$_3$H, O(CH$_2$)$_r$PO$_3$H$_2$, O(CH$_2$)$_r$PO$_3$RH, S(CH$_2$)$_r$CO$_2$R$^3$, S(CH$_2$)$_r$SO$_3$H, S(CH$_2$)$_r$PO$_3$H$_2$, NHR$^3$CONHR$^3$, NHCO$_2$R$^3$, S(CH$_2$)$_r$PO$_3$RH, (CH$_2$)$_r$CON(R$^3$)$_2$, S(CH$_2$)$_n$CON(R$^3$)$_2$, O(CH$_2$)$_n$CON(R$^3$)$_2$, (CH$_2$)$_n$NR$^3$SO$_2$R, (CH$_2$)$_r$C(=NR$^3$)N(R$^3$)$_2$, (CH$_2$)$_r$NR$^3$C(=NR$^3$)N(R$^3$)$_2$, (CH$_2$)$_r$NR$^3$(C=NR$^3$CN)N(R$^3$)$_2$, (CH$_2$)$_r$NR$^3$(C=CHNO$_2$)N(R$^3$)$_2$, (CH$_2$)$_r$NR$^3$C(=NR$^5$)NR$^3$R$^{5a}$, (CH$_2$)$_r$tetrazol-5-yl, and O(CH$_2$CH$_2$O)$_q$R$^4$;

R$^1$ is

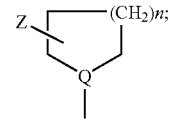

A is selected from H, C$_{1-6}$ alkyl, OH, C$_{1-6}$ alkylene-OH, (CH$_2$)$_m$NR$^c$$_2$, (CH$_2$)$_1$CONR$^c$$_2$, (CH$_2$)$_n$NHCONR$^c$$_2$, (CH$_2$)$_n$NHCO$_2$R, (CH$_2$)$_m$C(=NH)NH$_2$, (CH$_2$)$_m$—C$_{3-6}$-cycloalkyl, (CH$_2$)$_m$-heteroaryl, and (CH$_2$)$_m$-aryl, wherein each aryl and heteroaryl is substituted with 0-2 groups selected from CF$_3$, halogen, C$_{1-4}$ alkyl, —CN, CONR$^c$$_2$, NO$_2$, NR$_2$, OR, NR$^c$CONR$^c$$_2$, NR$^c$CO$_2$R, NHSO$_2$CH$_3$, and SONHR;

R$^2$ is selected from H, C$_{1-6}$ alkyl, (CH$_2$)$_{0-6}$ aryl, and (CH$_2$)$_{0-6}$ heteroaryl, wherein the heteroaryl is attached via a carbon atom;

Z is selected from NRZ', CH$_2$O(CH$_2$)$_n$CO$_2$R, (CH$_2$)$_m$C(=NH)NH$_2$, (CH$_2$)$_m$NHC(=NH)NH$_2$, (CH$_2$)$_m$NHC(=CHNO$_2$)NH$_2$, (CH$_2$)$_m$NHC(=NCN)NH$_2$, NR$^c$CONR$^c$$_2$, NR$^c$CO$_2$R, OCH$_2$CH=CHCO$_2$R, CH$_2$OCH$_2$CH=CHCO$_2$R, O(CH$_2$)$_n$PO(OR)$_2$, CH$_2$O(CH$_2$)$_n$PO(OR)$_2$, CONR$^c$$_2$, (CH$_2$)$_n$CONR$^c$$_2$, O(CH$_2$)$_n$CONR$^c$$_2$, CH$_2$O(CH$_2$)$_m$CONR$^c$$_2$, OCH$_2$CH=CHCONR$^c$$_2$, CH$_2$OCH$_2$CH=CHCONR$^c$$_2$, and (CH$_2$)$_m$SO$_3$R;

Z' is selected from (CH)$_m$CH(A)(CH$_2$)$_m$CO$_2$R, (CH)$_m$CH(A)(CH$_2$)$_m$CONH(CH)$_m$CH(A)(CH$_2$)$_m$CO$_2$R, (CH)$_m$CH(A)(CH$_2$)$_m$CONH(CH)$_m$CH(A)(CH$_2$)$_m$CONH(CH)$_m$CH(A)(CH$_2$)$_m$CO$_2$R, (CH)$_m$CH(A)(CH$_2$)$_m$CONR$^c$$_2$, (CH)$_m$CH(A)(CH$_2$)$_m$CONH(CH)$_m$CH(A)(CH$_2$)$_m$CONR$^c$$_2$, (CH)$_m$CH(A)(CH$_2$)$_m$CONH(CH)$_m$CH(A)(CH$_2$)$_m$CONH(CH)$_m$CH(A)(CH$_2$)$_m$CONR$^c$$_2$, (CH$_2$)$_m$-phenyl-(CH$_2$)$_m$CO$_2$R, (CH$_2$)$_m$-pyridyl-(CH$_2$)$_m$CO$_2$R, (CH$_2$)$_m$-phenyl-(CH$_2$)$_m$CONR$^c$$_2$, and (CH$_2$)$_m$-pyridyl-(CH$_2$)$_m$CONR$^c$$_2$;

Q is selected from N, CH, and CQ';

Q' is selected from H, CO$_2$R, (CH$_2$)$_n$CO$_2$R, CH$_2$O(CH$_2$)$_n$CO$_2$R, CH$_2$OCH$_2$CH=CHCO$_2$R, CH$_2$O(CH$_2$)$_n$PO(OR)$_2$, CONR$^c$$_2$, (CH$_2$)$_n$CONR$^c$$_2$, CH$_2$O(CH$_2$)$_n$CONR$^c$$_2$, CH$_2$OCH$_2$CH=CHCONR$^c$$_2$, and (CH$_2$)$_m$tetrazole;

V is selected from H, C$_{1-6}$ alkyl, C$_{2-6}$ alkenyl, C$_{2-6}$ alkynyl, CF$_3$, aryl, CH$_2$OH, CH$_2$O(CH$_2$CH$_2$O)$_p$R, (CH$_2$)$_m$CN, (CH$_2$)$_m$C(=NH)NH$_2$, (CH$_2$)$_n$NHC(=NH)NH$_2$, (CH$_2$)$_n$NHC(=CHNO$_2$)NH$_2$, (CH$_2$)$_n$NHC(=NCN)NH$_2$, (CH$_2$)$_m$CONR$^c$$_2$, (CH$_2$)$_m$CONR$^a$(CH$_2$)$_m$CH(A)(CH$_2$)$_m$CO$_2$R, (CH$_2$)$_m$CONR$^a$(CH$_2$)$_m$-phenyl-(CH$_2$)$_m$CO$_2$R, (CH$_2$)$_m$CONR$^a$(CH$_2$)$_m$-phenyl-(CH$_2$)$_m$-tetrazole, CH$_2$O(CH$_2$)$_n$CONR$^c$$_2$, CH$_2$NR$^a$(CH$_2$)$_n$CONR$^c$$_2$, CH$_2$N$^+$R$^b$$_3$V$^1$, tetrazole, and

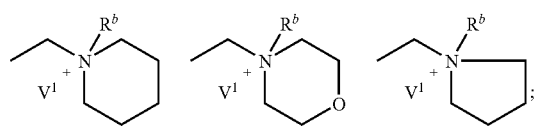

R is independently selected from H and $C_{1-6}$ alkyl;

$R^a$ is independently selected from H, $C_{1-6}$ alkyl, $C_{2-6}$ alkenyl, and $C_{2-6}$ alkynyl;

$R^b$ is independently selected from $O^-$, $C_{1-6}$ alkyl, $C_{3-6}$ alkenyl, and $C_{3-6}$ alkynyl;

$R^c$ is independently selected from H, OH, $C_{1-4}$ alkyl, $C_{3-6}$ alkenyl, CHRCHROH, CR(CHROH)$_2$, C(CHROH)$_3$, CHRCH(aryl)OH, and CH(aryl)CHROH;

$V^1$ is a counter ion, provided that $V^1$ is absent when $R^b$ is $O^-$;

m is selected from 0, 1, 2, 3, and 4;

n is selected from 1, 2, 3, and 4; and, p is selected from 1, 2, 3, 4, 5, 6, 7, 8, 9, 10, 11, and 12.

2. A compound of claim 1, wherein the compound is of formula II or a stereoisomer or pharmaceutically acceptable salt thereof:

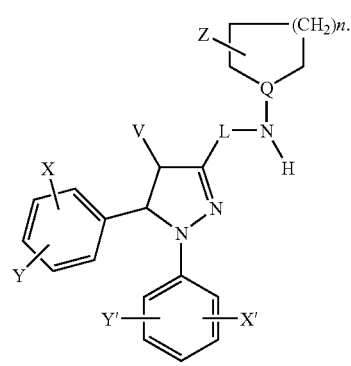

II

3. A compound of claim 1, wherein the compound is of formula IIa or a stereoisomer or pharmaceutically acceptable salt thereof:

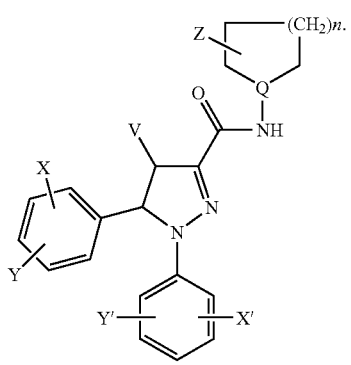

IIa

4. A compound of claim 2, wherein:

X, X', Y, and Y' are independently selected from H, Cl, F, $C_{1-4}$ alkyl, $CF_3$, —CN, $NO_2$, $NR_2$, and OR;

Z is selected from $CH_2O(CH_2)_nCO_2R$, $(CH_2)_mC(=NH)NH_2$, $(CH_2)_mNHC(=NH)NH_2$, $NR^cCONR^c{}_2$, $NR^cCO_2R$, $(CH_2)_mNHC(=CHNO_2)NH_2$, $(CH_2)_mNHC(=NCN)NH_2$, $OCH_2CH=CHCO_2R$, $CH_2OCH_2CH=CHCO_2R$, $O(CH_2)_nPO(OR)_2$, $CH_2O(CH_2)_nPO(OR)_2$, $CONR^c{}_2$, $(CH_2)_nCONR^c{}_2$, $O(CH_2)_nCONR^c{}_2$, $CH_2O(CH_2)_nCONR^c{}_2$, $OCH_2CH=CHCONR^c{}_2$, and $CH_2OCH_2CH=CHCONR^c{}_2$;

Q is selected from N and CH;

V is selected from H, $C_{1-6}$ alkyl, $C_{2-6}$ alkenyl, $CF_3$, aryl, and $(CH_2)_mCN$;

R is selected from H, $C_{1-4}$ alkyl, and $C_{2-4}$ alkenyl; and, n is selected from 1 and 2.

5. A compound of claim 1, wherein the compound is selected from the compounds of Table 1b or a stereoisomer or a pharmaceutically acceptable salt thereof:

TABLE 1b

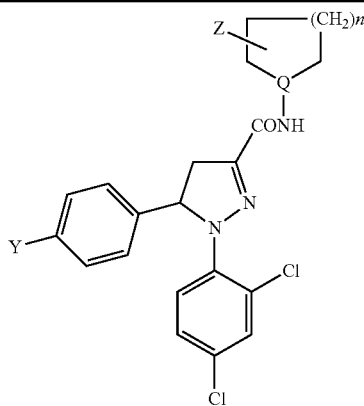

| Ex. # | Y | Z (position on ring) | Q | n |
|---|---|---|---|---|
| 1 | Cl | 2-$CH_2OCH_2CO_2Et$ | N | 1 |
| 2 | Cl | 2-$CH_2OCH_2CO_2H$ | N | 1 |
| 3 | Cl | 2-$CH_2O(CH_2)_3PO(OEt)_2$ | N | 1 |
| 4 | Cl | 2-$CH_2O(CH_2)_3PO(OH)_2$ | N | 1 |
| 5 | $CH_3$ | 2-$CH_2OCH_2CO_2Et$ | N | 1 |
| 6 | $CH_3$ | 2-$CH_2OCH_2CO_2H$ | N | 1 |
| 7 | $CH_3$ | 2-$CH_2O(CH_2)_3PO(OEt)_2$ | N | 1 |
| 8 | $CH_3$ | 2-$CH_2O(CH_2)_3PO(OH)_2$ | N | 1 |
| 9 | $OCH_3$ | 2-$CH_2OCH_2CO_2Et$ | N | 1 |
| 10 | $OCH_3$ | 2-$CH_2OCH_2CO_2H$ | N | 1 |
| 11 | $OCH_3$ | 2-$CH_2O(CH_2)_3PO(OEt)_2$ | N | 1 |
| 12 | $OCH_3$ | 2-$CH_2O(CH_2)_3PO(OH)_2$ | N | 1 |
| 13 | $CH(CH_3)_2$ | 2-$CH_2OCH_2CO_2Et$ | N | 1 |
| 14 | $CH(CH_3)_2$ | 2-$CH_2OCH_2CO_2H$ | N | 1 |
| 15 | $CH(CH_3)_2$ | 2-$CH_2O(CH_2)_3PO(OEt)_2$ | N | 1 |
| 16 | $CH(CH_3)_2$ | 2-$CH_2O(CH_2)_3PO(OH)_2$ | N | 1 |
| 17 | Cl | 2-$CH_2OCH_2CO_2Et$ | N | 2 |
| 18 | Cl | 2-$CH_2OCH_2CO_2H$ | N | 2 |
| 19 | Cl | 2-$CH_2O(CH_2)_3PO(OEt)_2$ | N | 2 |
| 20 | Cl | 2-$CH_2O(CH_2)_3PO(OH)_2$ | N | 2 |
| 21 | $CH_3$ | 2-$CH_2OCH_2CO_2Et$ | N | 2 |
| 22 | $CH_3$ | 2-$CH_2OCH_2CO_2H$ | N | 2 |
| 23 | $CH_3$ | 2-$CH_2O(CH_2)_3PO(OEt)_2$ | N | 2 |
| 24 | $CH_3$ | 2-$CH_2O(CH_2)_3PO(OH)_2$ | N | 2 |
| 25 | $OCH_3$ | 2-$CH_2OCH_2CO_2Et$ | N | 2 |
| 26 | $OCH_3$ | 2-$CH_2OCH_2CO_2H$ | N | 2 |
| 27 | $OCH_3$ | 2-$CH_2O(CH_2)_3PO(OEt)_2$ | N | 2 |
| 28 | $OCH_3$ | 2-$CH_2O(CH_2)_3PO(OH)_2$ | N | 2 |
| 29 | $CH(CH_3)_2$ | 2-$CH_2OCH_2CO_2Et$ | N | 2 |
| 30 | $CH(CH_3)_2$ | 2-$CH_2OCH_2CO_2H$ | N | 2 |
| 31 | $CH(CH_3)_2$ | 2-$CH_2O(CH_2)_3PO(OEt)_2$ | N | 2 |
| 32 | $CH(CH_3)_2$ | 2-$CH_2O(CH_2)_3PO(OH)_2$ | N | 2 |
| 33 | Cl | 3-$CH_2OCH_2CO_2Et$ | N | 1 |
| 34 | Cl | 3-$CH_2OCH_2CO_2H$ | N | 1 |
| 35 | Cl | 3-$CH_2O(CH_2)_3PO(OEt)_2$ | N | 1 |
| 36 | Cl | 3-$CH_2O(CH_2)_3PO(OH)_2$ | N | 1 |
| 37 | $CH_3$ | 3-$CH_2OCH_2CO_2Et$ | N | 1 |
| 38 | $CH_3$ | 3-$CH_2OCH_2CO_2H$ | N | 1 |
| 39 | $CH_3$ | 3-$CH_2O(CH_2)_3PO(OEt)_2$ | N | 1 |
| 40 | $CH_3$ | 3-$CH_2O(CH_2)_3PO(OH)_2$ | N | 1 |
| 41 | $OCH_3$ | 3-$CH_2OCH_2CO_2Et$ | N | 1 |
| 42 | $OCH_3$ | 3-$CH_2OCH_2CO_2H$ | N | 1 |
| 43 | $OCH_3$ | 3-$CH_2O(CH_2)_3PO(OEt)_2$ | N | 1 |
| 44 | $OCH_3$ | 3-$CH_2O(CH_2)_3PO(OH)_2$ | N | 1 |
| 45 | $CH(CH_3)_2$ | 3-$CH_2OCH_2CO_2Et$ | N | 1 |
| 46 | $CH(CH_3)_2$ | 3-$CH_2OCH_2CO_2H$ | N | 1 |
| 47 | $CH(CH_3)_2$ | 3-$CH_2O(CH_2)_3PO(OEt)_2$ | N | 1 |

TABLE 1b-continued

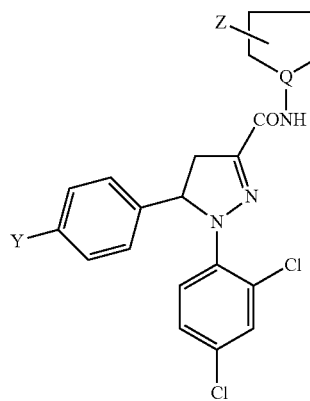

| Ex. # | Y | Z (position on ring) | Q | n |
|---|---|---|---|---|
| 48 | $CH(CH_3)_2$ | 3-$CH_2O(CH_2)_3PO(OH)_2$ | N | 1 |
| 49 | Cl | 3-$CH_2OCH_2CO_2Et$ | N | 2 |
| 50 | Cl | 3-$CH_2OCH_2CO_2H$ | N | 2 |
| 51 | Cl | 3-$CH_2O(CH_2)_3PO(OEt)_2$ | N | 2 |
| 52 | Cl | 3-$CH_2O(CH_2)_3PO(OH)_2$ | N | 2 |
| 53 | $CH_3$ | 3-$CH_2OCH_2CO_2Et$ | N | 2 |
| 54 | $CH_3$ | 3-$CH_2OCH_2CO_2H$ | N | 2 |
| 55 | $CH_3$ | 3-$CH_2O(CH_2)_3PO(OEt)_2$ | N | 2 |
| 56 | $CH_3$ | 3-$CH_2O(CH_2)_3PO(OH)_2$ | N | 2 |
| 57 | $OCH_3$ | 3-$CH_2OCH_2CO_2Et$ | N | 2 |
| 58 | $OCH_3$ | 3-$CH_2OCH_2CO_2H$ | N | 2 |
| 59 | $OCH_3$ | 3-$CH_2O(CH_2)_3PO(OEt)_2$ | N | 2 |
| 60 | $OCH_3$ | 3-$CH_2O(CH_2)_3PO(OH)_2$ | N | 2 |
| 61 | $CH(CH_3)_2$ | 3-$CH_2OCH_2CO_2Et$ | N | 2 |
| 62 | $CH(CH_3)_2$ | 3-$CH_2OCH_2CO_2H$ | N | 2 |
| 63 | $CH(CH_3)_2$ | 3-$CH_2O(CH_2)_3PO(OEt)_2$ | N | 2 |
| 64 | $CH(CH_3)_2$ | 3-$CH_2O(CH_2)_3PO(OH)_2$ | N | 2 |
| 65 | Cl | 4-$CH_2OCH_2CO_2Et$ | N | 2 |
| 66 | Cl | 4-$CH_2OCH_2CO_2H$ | N | 2 |
| 67 | Cl | 4-$CH_2O(CH_2)_3PO(OEt)_2$ | N | 2 |
| 68 | Cl | 4-$CH_2O(CH_2)_3PO(OH)_2$ | N | 2 |
| 69 | $CH_3$ | 4-$CH_2OCH_2CO_2Et$ | N | 2 |
| 70 | $CH_3$ | 4-$CH_2OCH_2CO_2H$ | N | 2 |
| 71 | $CH_3$ | 4-$CH_2O(CH_2)_3PO(OEt)_2$ | N | 2 |
| 72 | $CH_3$ | 4-$CH_2O(CH_2)_3PO(OH)_2$ | N | 2 |
| 73 | $OCH_3$ | 4-$CH_2OCH_2CO_2Et$ | N | 2 |
| 74 | $OCH_3$ | 4-$CH_2OCH_2CO_2H$ | N | 2 |
| 75 | $OCH_3$ | 4-$CH_2O(CH_2)_3PO(OEt)_2$ | N | 2 |
| 76 | $OCH_3$ | 4-$CH_2O(CH_2)_3PO(OH)_2$ | N | 2 |
| 77 | $CH(CH_3)_2$ | 4-$CH_2OCH_2CO_2Et$ | N | 2 |
| 78 | $CH(CH_3)_2$ | 4-$CH_2OCH_2CO_2H$ | N | 2 |
| 79 | $CH(CH_3)_2$ | 4-$CH_2O(CH_2)_3PO(OEt)_2$ | N | 2 |
| 80 | $CH(CH_3)_2$ | 4-$CH_2O(CH_2)_3PO(OH)_2$ | N | 2 |
| 81 | Cl | 2-$CH_2OCH_2CO_2Et$ | CH | 1 |
| 82 | Cl | 2-$CH_2OCH_2CO_2H$ | CH | 1 |
| 83 | Cl | 2-$CH_2O(CH_2)_3PO(OEt)_2$ | CH | 1 |
| 84 | Cl | 2-$CH_2O(CH_2)_3PO(OH)_2$ | CH | 1 |
| 85 | $CH_3$ | 2-$CH_2OCH_2CO_2Et$ | CH | 1 |
| 86 | $CH_3$ | 2-$CH_2OCH_2CO_2H$ | CH | 1 |
| 87 | $CH_3$ | 2-$CH_2O(CH_2)_3PO(OEt)_2$ | CH | 1 |
| 88 | $CH_3$ | 2-$CH_2O(CH_2)_3PO(OH)_2$ | CH | 1 |
| 89 | $OCH_3$ | 2-$CH_2OCH_2CO_2Et$ | CH | 1 |
| 90 | $OCH_3$ | 2-$CH_2OCH_2CO_2H$ | CH | 1 |
| 91 | $OCH_3$ | 2-$CH_2O(CH_2)_3PO(OEt)_2$ | CH | 1 |
| 92 | $OCH_3$ | 2-$CH_2O(CH_2)_3PO(OH)_2$ | CH | 1 |
| 93 | $CH(CH_3)_2$ | 2-$CH_2OCH_2CO_2Et$ | CH | 1 |
| 94 | $CH(CH_3)_2$ | 2-$CH_2OCH_2CO_2H$ | CH | 1 |
| 95 | $CH(CH_3)_2$ | 2-$CH_2O(CH_2)_3PO(OEt)_2$ | CH | 1 |
| 96 | $CH(CH_3)_2$ | 2-$CH_2O(CH_2)_3PO(OH)_2$ | CH | 1 |
| 97 | Cl | 2-$CH_2OCH_2CO_2Et$ | CH | 2 |
| 98 | Cl | 2-$CH_2OCH_2CO_2H$ | CH | 2 |
| 99 | Cl | 2-$CH_2O(CH_2)_3PO(OEt)_2$ | CH | 2 |
| 100 | Cl | 2-$CH_2O(CH_2)_3PO(OH)_2$ | CH | 2 |
| 101 | $CH_3$ | 2-$CH_2OCH_2CO_2Et$ | CH | 2 |
| 102 | $CH_3$ | 2-$CH_2OCH_2CO_2H$ | CH | 2 |
| 103 | $CH_3$ | 2-$CH_2O(CH_2)_3PO(OEt)_2$ | CH | 2 |
| 104 | $CH_3$ | 2-$CH_2O(CH_2)_3PO(OH)_2$ | CH | 2 |
| 105 | $OCH_3$ | 2-$CH_2OCH_2CO_2Et$ | CH | 2 |

TABLE 1b-continued

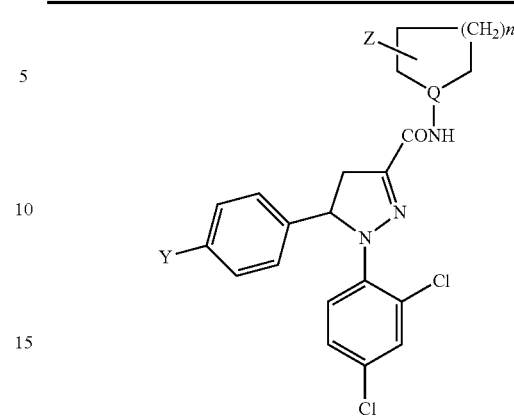

| Ex. # | Y | Z (position on ring) | Q | n |
|---|---|---|---|---|
| 105 | $OCH_3$ | 2-$CH_2OCH_2CO_2H$ | CH | 2 |
| 107 | $OCH_3$ | 2-$CH_2O(CH_2)_3PO(OEt)_2$ | CH | 2 |
| 108 | $OCH_3$ | 2-$CH_2O(CH_2)_3PO(OH)_2$ | CH | 2 |
| 109 | $CH(CH_3)_2$ | 2-$CH_2OCH_2CO_2Et$ | CH | 2 |
| 110 | $CH(CH_3)_2$ | 2-$CH_2OCH_2CO_2H$ | CH | 2 |
| 111 | $CH(CH_3)_2$ | 2-$CH_2O(CH_2)_3PO(OEt)_2$ | CH | 2 |
| 112 | $CH(CH_3)_2$ | 2-$CH_2O(CH_2)_3PO(OH)_2$ | CH | 2 |
| 113 | Cl | 1-$CH_2OCH_2CO_2Et$ | C | 1 |
| 114 | Cl | 1-$CH_2OCH_2CO_2H$ | C | 1 |
| 115 | Cl | 1-$CH_2O(CH_2)_3PO(OEt)_2$ | C | 1 |
| 116 | Cl | 1-$CH_2O(CH_2)_3PO(OH)_2$ | C | 1 |
| 117 | $CH_3$ | 1-$CH_2OCH_2CO_2Et$ | C | 1 |
| 118 | $CH_3$ | 1-$CH_2OCH_2CO_2H$ | C | 1 |
| 119 | $CH_3$ | 1-$CH_2O(CH_2)_3PO(OEt)_2$ | C | 1 |
| 120 | $CH_3$ | 1-$CH_2O(CH_2)_3PO(OH)_2$ | C | 1 |
| 121 | $OCH_3$ | 1-$CH_2OCH_2CO_2Et$ | C | 1 |
| 122 | $OCH_3$ | 1-$CH_2OCH_2CO_2H$ | C | 1 |
| 123 | $OCH_3$ | 1-$CH_2O(CH_2)_3PO(OEt)_2$ | C | 1 |
| 124 | $OCH_3$ | 1-$CH_2O(CH_2)_3PO(OH)_2$ | C | 1 |
| 125 | $CH(CH_3)_2$ | 1-$CH_2OCH_2CO_2Et$ | C | 1 |
| 126 | $CH(CH_3)_2$ | 1-$CH_2OCH_2CO_2H$ | C | 1 |
| 127 | $CH(CH_3)_2$ | 1-$CH_2O(CH_2)_3PO(OEt)_2$ | C | 1 |
| 128 | $CH(CH_3)_2$ | 1-$CH_2O(CH_2)_3PO(OH)_2$ | C | 1 |
| 129 | Cl | 3-$CH_2OCH_2CO_2Et$ | CH | 2 |
| 130 | Cl | 3-$CH_2OCH_2CO_2H$ | CH | 2 |
| 131 | Cl | 3-$CH_2O(CH_2)_3PO(OEt)_2$ | CH | 2 |
| 132 | Cl | 3-$CH_2O(CH_2)_3PO(OH)_2$ | CH | 2 |
| 133 | $CH_3$ | 3-$CH_2OCH_2CO_2Et$ | CH | 2 |
| 134 | $CH_3$ | 3-$CH_2OCH_2CO_2H$ | CH | 2 |
| 135 | $CH_3$ | 3-$CH_2O(CH_2)_3PO(OEt)_2$ | CH | 2 |
| 136 | $CH_3$ | 3-$CH_2O(CH_2)_3PO(OH)_2$ | CH | 2 |
| 137 | $OCH_3$ | 3-$CH_2OCH_2CO_2Et$ | CH | 2 |
| 138 | $OCH_3$ | 3-$CH_2OCH_2CO_2H$ | CH | 2 |
| 139 | $OCH_3$ | 3-$CH_2O(CH_2)_3PO(OEt)_2$ | CH | 2 |
| 140 | $OCH_3$ | 3-$CH_2O(CH_2)_3PO(OH)_2$ | CH | 2 |
| 141 | $CH(CH_3)_2$ | 3-$CH_2OCH_2CO_2Et$ | CH | 2 |
| 142 | $CH(CH_3)_2$ | 3-$CH_2OCH_2CO_2H$ | CH | 2 |
| 143 | $CH(CH_3)_2$ | 3-$CH_2O(CH_2)_3PO(OEt)_2$ | CH | 2 |
| 144 | $CH(CH_3)_2$ | 3-$CH_2O(CH_2)_3PO(OH)_2$ | CH | 2. |

6. A compound of claim 1, wherein the compound is selected from the compounds of Table 1c or a stereoisomer or a pharmaceutically acceptable salt thereof:

TABLE 1c

| Ex. # | Y | Z (position on ring) | Q | n |
|---|---|---|---|---|
| 1 | Cl | 2-CONH$_2$ | N | 1 |
| 2 | Cl | 2-CH$_2$OCH$_2$CONH$_2$ | N | 1 |
| 3 | Cl | 2-CH$_2$CONH$_2$ | N | 1 |
| 4 | Cl | 2-CH$_2$OCH$_2$CH=CHCONH$_2$ | N | 1 |
| 5 | CH$_3$ | 2-CONH$_2$ | N | 1 |
| 6 | CH$_3$ | 2-CH$_2$OCH$_2$CONH$_2$ | N | 1 |
| 7 | CH$_3$ | 2-CH$_2$CONH$_2$ | N | 1 |
| 8 | CH$_3$ | 2-CH$_2$OCH$_2$CH=CHCONH$_2$ | N | 1 |
| 9 | OCH$_3$ | 2-CONH$_2$ | N | 1 |
| 10 | OCH$_3$ | 2-CH$_2$OCH$_2$CONH$_2$ | N | 1 |
| 11 | OCH$_3$ | 2-CH$_2$CONH$_2$ | N | 1 |
| 12 | OCH$_3$ | 2-CH$_2$OCH$_2$CH=CHCONH$_2$ | N | 1 |
| 13 | CH(CH$_3$)$_2$ | 2-CONH$_2$ | N | 1 |
| 14 | CH(CH$_3$)$_2$ | 2-CH$_2$OCH$_2$CONH$_2$ | N | 1 |
| 15 | CH(CH$_3$)$_2$ | 2-CH$_2$CONH$_2$ | N | 1 |
| 16 | CH(CH$_3$)$_2$ | 2-CH$_2$OCH$_2$CH=CHCONH$_2$ | N | 1 |
| 17 | Cl | 2-CONH$_2$ | N | 2 |
| 18 | Cl | 2-CH$_2$OCH$_2$CONH$_2$ | N | 2 |
| 19 | Cl | 2-CH$_2$CONH$_2$ | N | 2 |
| 20 | Cl | 2-CH$_2$OCH$_2$CH=CHCONH$_2$ | N | 2 |
| 21 | CH$_3$ | 2-CONH$_2$ | N | 2 |
| 22 | CH$_3$ | 2-CH$_2$OCH$_2$CONH$_2$ | N | 2 |
| 23 | CH$_3$ | 2-CH$_2$CONH$_2$ | N | 2 |
| 24 | CH$_3$ | 2-CH$_2$OCH$_2$CH=CHCONH$_2$ | N | 2 |
| 25 | OCH$_3$ | 2-CONH$_2$ | N | 2 |
| 26 | OCH$_3$ | 2-CH$_2$OCH$_2$CONH$_2$ | N | 2 |
| 27 | OCH$_3$ | 2-CH$_2$CONH$_2$ | N | 2 |
| 28 | OCH$_3$ | 2-CH$_2$OCH$_2$CH=CHCONH$_2$ | N | 2 |
| 29 | CH(CH$_3$)$_2$ | 2-CONH$_2$ | N | 2 |
| 30 | CH(CH$_3$)$_2$ | 2-CH$_2$OCH$_2$CONH$_2$ | N | 2 |
| 31 | CH(CH$_3$)$_2$ | 2-CH$_2$CONH$_2$ | N | 2 |
| 32 | CH(CH$_3$)$_2$ | 2-CH$_2$OCH$_2$CH=CHCONH$_2$ | N | 2 |
| 33 | Cl | 3-CONH$_2$ | N | 1 |
| 34 | Cl | 3-CH$_2$OCH$_2$CONH$_2$ | N | 1 |
| 35 | Cl | 3-CH$_2$CONH$_2$ | N | 1 |
| 36 | Cl | 3-CH$_2$OCH$_2$CH=CHCONH$_2$ | N | 1 |
| 37 | CH$_3$ | 3-CONH$_2$ | N | 1 |
| 38 | CH$_3$ | 3-CH$_2$OCH$_2$CONH$_2$ | N | 1 |
| 39 | CH$_3$ | 3-CH$_2$CONH$_2$ | N | 1 |
| 40 | CH$_3$ | 3-CH$_2$OCH$_2$CH=CHCONH$_2$ | N | 1 |
| 41 | OCH$_3$ | 3-CONH$_2$ | N | 1 |
| 42 | OCH$_3$ | 3-CH$_2$OCH$_2$CONH$_2$ | N | 1 |
| 43 | OCH$_3$ | 3-CH$_2$CONH$_2$ | N | 1 |
| 44 | OCH$_3$ | 3-CH$_2$OCH$_2$CH=CHCONH$_2$ | N | 1 |
| 45 | CH(CH$_3$)$_2$ | 3-CONH$_2$ | N | 1 |
| 4 | CH(CH$_3$)$_2$ | 3-CH$_2$OCH$_2$CONH$_2$ | N | 1 |
| 47 | CH(CH$_3$)$_2$ | 3-CH$_2$CONH$_2$ | N | 1 |
| 48 | CH(CH$_3$)$_2$ | 3-CH$_2$OCH$_2$CH=CHCONH$_2$ | N | 1 |
| 49 | Cl | 3-CONH$_2$ | N | 2 |
| 50 | Cl | 3-CH$_2$OCH$_2$CONH$_2$ | N | 2 |
| 51 | Cl | 3-CH$_2$CONH$_2$ | N | 2 |
| 52 | Cl | 3-CH$_2$OCH$_2$CH=CHCONH$_2$ | N | 2 |
| 53 | CH$_3$ | 3-CONH$_2$ | N | 2 |
| 54 | CH$_3$ | 3-CH$_2$OCH$_2$CONH$_2$ | N | 2 |
| 55 | CH$_3$ | 3-CH$_2$CONH$_2$ | N | 2 |
| 56 | CH$_3$ | 3-CH$_2$OCH$_2$CH=CHCONH$_2$ | N | 2 |
| 57 | OCH$_3$ | 3-CONH$_2$ | N | 2 |
| 58 | OCH$_3$ | 3-CH$_2$OCH$_2$CONH$_2$ | N | 2 |
| 59 | OCH$_3$ | 3-CH$_2$CONH$_2$ | N | 2 |
| 60 | OCH$_3$ | 3-CH$_2$OCH$_2$CH=CHCONH$_2$ | N | 2 |
| 61 | CH(CH$_3$)$_2$ | 3-CONH$_2$ | N | 2 |
| 62 | CH(CH$_3$)$_2$ | 3-CH$_2$OCH$_2$CONH$_2$ | N | 2 |
| 63 | CH(CH$_3$)$_2$ | 3-CH$_2$CONH$_2$ | N | 2 |
| 64 | CH(CH$_3$)$_2$ | 3-CH$_2$OCH$_2$CH=CHCONH$_2$ | N | 2 |
| 65 | Cl | 4-CONH$_2$ | N | 2 |
| 66 | Cl | 4-CH$_2$OCH$_2$CONH$_2$ | N | 2 |
| 67 | Cl | 4-CH$_2$CONH$_2$ | N | 2 |
| 68 | Cl | 4-CH$_2$OCH$_2$CH=CHCONH$_2$ | N | 2 |
| 69 | CH$_3$ | 4-CONH$_2$ | N | 2 |
| 70 | CH$_3$ | 4-CH$_2$OCH$_2$CONH$_2$ | N | 2 |
| 71 | CH$_3$ | 4-CH$_2$CONH$_2$ | N | 2 |
| 72 | CH$_3$ | 4-CH$_2$OCH$_2$CH=CHCONH$_2$ | N | 2 |
| 73 | OCH$_3$ | 4-CONH$_2$ | N | 2 |
| 74 | OCH$_3$ | 4-CH$_2$OCH$_2$CONH$_2$ | N | 2 |
| 75 | OCH$_3$ | 4-CH$_2$CONH$_2$ | N | 2 |
| 76 | OCH$_3$ | 4-CH$_2$OCH$_2$CH=CHCONH$_2$ | N | 2 |
| 77 | CH(CH$_3$)$_2$ | 4-CONH$_2$ | N | 2 |
| 78 | CH(CH$_3$)$_2$ | 4-CH$_2$OCH$_2$CONH$_2$ | N | 2 |
| 79 | CH(CH$_3$)$_2$ | 4-CH$_2$CONH$_2$ | N | 2 |
| 80 | CH(CH$_3$)$_2$ | 4-CH$_2$OCH$_2$CH=CHCONH$_2$ | N | 2 |
| 81 | Cl | 1-CONH$_2$ | C | 1 |
| 82 | Cl | 1-CH$_2$OCH$_2$CONH$_2$ | C | 1 |
| 83 | Cl | 1-CH$_2$CONH$_2$ | C | 1 |
| 84 | CH$_3$ | 1-CONH$_2$ | C | 1 |
| 85 | CH$_3$ | 1-CH$_2$OCH$_2$CONH$_2$ | C | 1 |
| 86 | CH$_3$ | 1-CH$_2$CONH$_2$ | C | 1 |
| 87 | OCH$_3$ | 1-CONH$_2$ | C | 1 |
| 88 | OCH$_3$ | 1-CH$_2$OCH$_2$CONH$_2$ | C | 1 |
| 89 | OCH$_3$ | 1-CH$_2$CONH$_2$ | C | 1 |
| 90 | CH(CH$_3$)$_2$ | 1-CONH$_2$ | C | 1 |
| 91 | CH(CH$_3$)$_2$ | 1-CH$_2$OCH$_2$CONH$_2$ | C | 1 |
| 92 | CH(CH$_3$)$_2$ | 1-CH$_2$CONH$_2$ | C | 1 |
| 93 | Cl | 1-CONH$_2$ | C | 2 |
| 94 | Cl | 1-CH$_2$OCH$_2$CONH$_2$ | C | 2 |
| 95 | Cl | 1-CH$_2$CONH$_2$ | C | 2 |
| 96 | CH$_3$ | 1-CONH$_2$ | C | 2 |
| 97 | CH$_3$ | 1-CH$_2$OCH$_2$CONH$_2$ | C | 2 |
| 98 | CH$_3$ | 1-CH$_2$CONH$_2$ | C | 2 |
| 99 | OCH$_3$ | 1-CONH$_2$ | C | 2 |
| 100 | OCH$_3$ | 1-CH$_2$OCH$_2$CONH$_2$ | C | 2 |
| 101 | OCH$_3$ | 1-CH$_2$CONH$_2$ | C | 2 |
| 102 | CH(CH$_3$)$_2$ | 1-CONH$_2$ | C | 2 |
| 103 | CH(CH$_3$)$_2$ | 1-CH$_2$OCH$_2$CONH$_2$ | C | 2 |
| 104 | CH(CH$_3$)$_2$ | 1-CH$_2$CONH$_2$ | C | 2 |
| 105 | Cl | 2-CONH$_2$ | CH | 1 |
| 105 | Cl | 2-CH$_2$OCH$_2$CONH$_2$ | CH | 1 |
| 107 | Cl | 2-CH$_2$CONH$_2$ | CH | 1 |
| 108 | Cl | 2-CH$_2$OCH$_2$CH=CHCONH$_2$ | CH | 1 |
| 109 | CH$_3$ | 2-CONH$_2$ | CH | 1 |
| 110 | CH$_3$ | 2-CH$_2$OCH$_2$CONH$_2$ | CH | 1 |
| 111 | CH$_3$ | 2-CH$_2$CONH$_2$ | CH | 1 |

TABLE 1c-continued

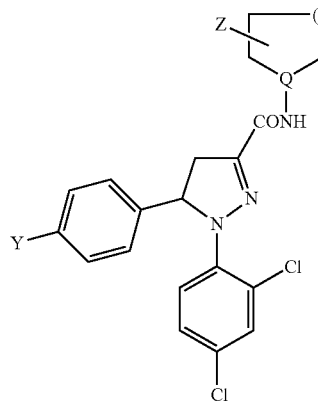

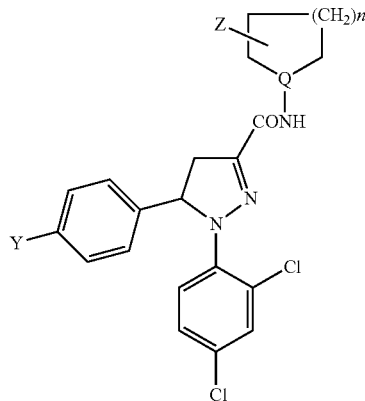

| Ex. # | Y | Z (position on ring) | Q | n |
|---|---|---|---|---|
| 112 | CH$_3$ | 2-CH$_2$OCH$_2$CH=CHCONH$_2$ | CH | 1 |
| 113 | OCH$_3$ | 2-CONH$_2$ | CH | 1 |
| 114 | OCH$_3$ | 2-CH$_2$OCH$_2$CONH$_2$ | CH | 1 |
| 115 | OCH$_3$ | 2-CH$_2$CONH$_2$ | CH | 1 |
| 116 | OCH$_3$ | 2-CH$_2$OCH$_2$CH=CHCONH$_2$ | CH | 1 |
| 117 | CH(CH$_3$)$_2$ | 2-CONH$_2$ | CH | 1 |
| 118 | CH(CH$_3$)$_2$ | 2-CH$_2$OCH$_2$CONH$_2$ | CH | 1 |
| 119 | CH(CH$_3$)$_2$ | 2-CH$_2$CONH$_2$ | CH | 1 |
| 120 | CH(CH$_3$)$_2$ | 2-CH$_2$OCH$_2$CH=CHCONH$_2$ | CH | 1 |
| 121 | Cl | 2-CONH$_2$ | CH | 2 |
| 122 | Cl | 2-CH$_2$OCH$_2$CONH$_2$ | CH | 2 |
| 123 | Cl | 2-CH$_2$CONH$_2$ | CH | 2 |
| 124 | Cl | 2-CH$_2$OCH$_2$CH=CHCONH$_2$ | CH | 2 |
| 125 | CH$_3$ | 2-CONH$_2$ | CH | 2 |
| 126 | CH$_3$ | 2-CH$_2$OCH$_2$CONH$_2$ | CH | 2 |
| 127 | CH$_3$ | 2-CH$_2$CONH$_2$ | CH | 2 |
| 128 | CH$_3$ | 2-CH$_2$OCH$_2$CH=CHCONH$_2$ | CH | 2 |
| 129 | OCH$_3$ | 2-CONH$_2$ | CH | 2 |
| 130 | OCH$_3$ | 2-CH$_2$OCH$_2$CONH$_2$ | CH | 2 |
| 131 | OCH$_3$ | 2-CH$_2$CONH$_2$ | CH | 2 |
| 132 | OCH$_3$ | 2-CH$_2$OCH$_2$CH=CHCONH$_2$ | CH | 2 |
| 133 | CH(CH$_3$)$_2$ | 2-CONH$_2$ | CH | 2 |
| 134 | CH(CH$_3$)$_2$ | 2-CH$_2$OCH$_2$CONH$_2$ | CH | 2 |
| 135 | CH(CH$_3$)$_2$ | 2-CH$_2$CONH$_2$ | CH | 2 |
| 136 | CH(CH$_3$)$_2$ | 2-CH$_2$OCH$_2$CH=CHCONH$_2$ | CH | 2 |
| 137 | Cl | 3-CONH$_2$ | CH | 1 |
| 138 | Cl | 3-CH$_2$OCH$_2$CONH$_2$ | CH | 1 |
| 139 | Cl | 3-CH$_2$CONH$_2$ | CH | 1 |
| 140 | Cl | 3-CH$_2$OCH$_2$CH=CHCONH$_2$ | CH | 1 |
| 141 | CH$_3$ | 3-CONH$_2$ | CH | 1 |
| 142 | CH$_3$ | 3-CH$_2$OCH$_2$CONH$_2$ | CH | 1 |
| 143 | CH$_3$ | 3-CH$_2$CONH$_2$ | CH | 1 |
| 144 | CH$_3$ | 3-CH$_2$OCH$_2$CH=CHCONH$_2$ | CH | 1 |
| 145 | OCH$_3$ | 3-CONH$_2$ | CH | 1 |
| 146 | OCH$_3$ | 3-CH$_2$OCH$_2$CONH$_2$ | CH | 1 |
| 147 | OCH$_3$ | 3-CH$_2$CONH$_2$ | CH | 1 |
| 148 | OCH$_3$ | 3-CH$_2$OCH$_2$CH=CHCONH$_2$ | CH | 1 |
| 149 | CH(CH$_3$)$_2$ | 3-CONH$_2$ | CH | 1 |
| 150 | CH(CH$_3$)$_2$ | 3-CH$_2$OCH$_2$CONH$_2$ | CH | 1 |
| 151 | CH(CH$_3$)$_2$ | 3-CH$_2$CONH$_2$ | CH | 1 |
| 153 | CH(CH$_3$)$_2$ | 3-CH$_2$OCH$_2$CH=CHCONH$_2$ | CH | 1 |
| 154 | Cl | 4-CONH$_2$ | CH | 2 |
| 155 | Cl | 4-CH$_2$OCH$_2$CONH$_2$ | CH | 2 |
| 156 | Cl | 4-CH$_2$CONH$_2$ | CH | 2 |
| 157 | Cl | 4-CH$_2$OCH$_2$CH=CHCONH$_2$ | CH | 2 |
| 158 | CH$_3$ | 4-CONH$_2$ | CH | 2 |
| 159 | CH$_3$ | 4-CH$_2$OCH$_2$CONH$_2$ | CH | 2 |
| 160 | CH$_3$ | 4-CH$_2$CONH$_2$ | CH | 2 |
| 161 | CH$_3$ | 4-CH$_2$OCH$_2$CH=CHCONH$_2$ | CH | 2 |
| 162 | OCH$_3$ | 4-CONH$_2$ | CH | 2 |
| 163 | OCH$_3$ | 4-CH$_2$OCH$_2$CONH$_2$ | CH | 2 |
| 164 | OCH$_3$ | 4-CH$_2$CONH$_2$ | CH | 2 |
| 165 | OCH$_3$ | 4-CH$_2$OCH$_2$CH=CHCONH$_2$ | CH | 2 |
| 166 | CH(CH$_3$)$_2$ | 4-CONH$_2$ | CH | 2 |
| 176 | CH(CH$_3$)$_2$ | 4-CH$_2$OCH$_2$CONH$_2$ | CH | 2 |
| 168 | CH(CH$_3$)$_2$ | 4-CH$_2$CONH$_2$ | CH | 2 |
| 169 | CH(CH$_3$)$_2$ | 4-CH$_2$OCH$_2$CH=CHCONH$_2$ | CH | 2 |
| 170 | Cl | 4-C(NH)NH$_2$ | N | 2 |
| 171 | Cl | 3-C(NH)NH$_2$ | N | 2 |
| 172 | Cl | 2-C(NH)NH$_2$ | N | 1 |
| 173 | Cl | 3-C(NH)NH$_2$ | N | 1 |
| 174 | OCH$_3$ | 4-C(NH)NH$_2$ | N | 2 |
| 175 | OCH$_3$ | 3-C(NH)NH$_2$ | N | 2 |
| 176 | OCH$_3$ | 2-C(NH)NH$_2$ | N | 1 |
| 177 | OCH$_3$ | 3-C(NH)NH$_2$ | N | 1 |
| 178 | CH$_3$ | 4-C(NH)NH$_2$ | N | 2 |
| 179 | CH$_3$ | 3-C(NH)NH$_2$ | N | 2 |
| 180 | CH$_3$ | 2-C(NH)NH$_2$ | N | 1 |
| 181 | CH$_3$ | 3-C(NH)NH$_2$ | N | 1 |
| 182 | CH(CH$_3$)$_2$ | 4-C(NH)NH$_2$ | N | 2 |
| 183 | CH(CH$_3$)$_2$ | 3-C(NH)NH$_2$ | N | 2 |
| 184 | CH(CH$_3$)$_2$ | 2-C(NH)NH$_2$ | N | 1 |
| 185 | CH(CH$_3$)$_2$ | 3-C(NH)NH$_2$ | N | 1. |

7. A pharmaceutical composition, comprising: a compound according to claim 1 and a pharmaceutically acceptable carrier.

8. A pharmaceutical composition, comprising: a compound according to claim 2 and a pharmaceutically acceptable carrier.

9. A pharmaceutical composition, comprising: a compound according to claim 3 and a pharmaceutically acceptable carrier.

10. A pharmaceutical composition, comprising: a compound according to claim 4 and a pharmaceutically acceptable carrier.

11. A pharmaceutical composition, comprising: a compound according to claim 5 and a pharmaceutically acceptable carrier.

12. A pharmaceutical composition, comprising: a compound according to claim 6 and a pharmaceutically acceptable carrier.

\* \* \* \* \*